United States Patent
Maisano et al.

(10) Patent No.: US 9,545,265 B2
(45) Date of Patent: Jan. 17, 2017

(54) FOSSA OVALIS PENETRATION USING BALLOONS

(71) Applicant: TRANSSEPTAL SOLUTIONS LTD., Kefar Monash (IL)

(72) Inventors: Francesco Maisano, Zurich (CH); Elad Sapir, Kefar Yona (IL); Eyal Teichman, Hod-Hasharon (IL); Yuval Zipory, Modiin (IL)

(73) Assignee: TRANSSEPTAL SOLUTIONS LTD., Kefar Monash (IL)

( * ) Notice: Subject to any disclaimer, the term of this patent is extended or adjusted under 35 U.S.C. 154(b) by 42 days.

(21) Appl. No.: 14/287,470

(22) Filed: May 27, 2014

(65) Prior Publication Data

US 2014/0309678 A1    Oct. 16, 2014

Related U.S. Application Data

(63) Continuation-in-part of application No. 14/245,135, filed on Apr. 4, 2014.
(Continued)

(51) Int. Cl.
   *A61B 17/34*   (2006.01)
   *A61B 18/12*   (2006.01)
   (Continued)

(52) U.S. Cl.
   CPC .............. *A61B 17/3478* (2013.01); *A61B 6/12* (2013.01); *A61B 8/0841* (2013.01);
   (Continued)

(58) Field of Classification Search
   CPC ............. A61M 2025/1043; A61M 2025/1068; A61M 2025/1086; A61M 2025/1084; A61M 25/10; A61M 25/1002; A61M 25/1018; A61M 29/00; A61M 29/02; A61M 2029/025; A61B 2017/3484; A61B 2017/3488; A61B 2017/348; A61B 2017/3482; A61B 2017/3486; A61B 2017/22068; A61B 2017/22071; A61B 2017/22069; A61B 2017/00247; A61B 2017/301; A61B 2017/303; A61B 2017/306; A61B 17/320016; A61B 17/3205; A61B 17/3478; A61B 17/30; A61B 18/12; A61B 18/18; A61B 2018/00392; A61B 2018/00369
   See application file for complete search history.

(56) References Cited

U.S. PATENT DOCUMENTS 5,497,774 A    3/1996 Swartz
5,507,743 A    4/1996 Edwards
(Continued)

FOREIGN PATENT DOCUMENTS

DE    102005023414    11/2006
EP    0808607    11/1997
(Continued)

OTHER PUBLICATIONS

Restriction Requirement dated Sep. 9, 2015 in counterpart U.S. Appl. No. 14/245,135.
(Continued)

*Primary Examiner* — Jonathan Miles
*Assistant Examiner* — Kendra Obu
(74) *Attorney, Agent, or Firm* — Sughrue Mion, PLLC

(57) ABSTRACT

Apparatus and methods are described, including apparatus for puncturing a fossa ovalis of a heart. The apparatus comprises a catheter shaped to define a catheter lumen. A puncturing element is slidably disposed within the catheter lumen and configured to (a) be deployed from a distal portion of the catheter, and (b) puncture the fossa ovalis. A
(Continued)

balloon is configured to be deployed from the distal portion of the catheter, be radially expanded, and upon being deployed and expanded, facilitate positioning of the puncturing element, by contacting at least a portion of the fossa ovalis. Other applications are also described.

13 Claims, 31 Drawing Sheets

Related U.S. Application Data

(60) Provisional application No. 61/811,947, filed on Apr. 15, 2013.

(51) Int. Cl.

| | | |
|---|---|---|
| A61B 17/32 | (2006.01) | |
| A61B 17/3205 | (2006.01) | |
| A61B 18/00 | (2006.01) | |
| A61M 25/10 | (2013.01) | |
| A61B 18/18 | (2006.01) | |
| A61B 6/12 | (2006.01) | |
| A61B 8/08 | (2006.01) | |
| A61B 17/00 | (2006.01) | |
| A61B 17/22 | (2006.01) | |

(52) U.S. Cl.
CPC ... *A61B 17/3205* (2013.01); *A61B 17/320016* (2013.01); *A61B 18/12* (2013.01); *A61B 18/18* (2013.01); *A61B 2017/00247* (2013.01); *A61B 2017/22071* (2013.01); *A61B 2017/348* (2013.01); *A61B 2017/3486* (2013.01); *A61B 2017/3488* (2013.01); *A61B 2018/00369* (2013.01); *A61B 2090/065* (2016.02); *A61B 2090/0807* (2016.02); *A61M 25/1018* (2013.01); *A61M 2025/1086* (2013.01)

(56) References Cited

U.S. PATENT DOCUMENTS

| | | |
|---|---|---|
| 5,605,543 A | 2/1997 | Swanson |
| 5,807,395 A | 9/1998 | Mulier et al. |
| 5,910,150 A | 6/1999 | Saadat |
| 6,102,926 A | 8/2000 | Tartaglia |
| 6,623,449 B2 | 9/2003 | Paskar |
| 6,629,534 B1 | 10/2003 | St. Goar et al. |
| 6,641,564 B1 | 11/2003 | Kraus |
| 6,650,923 B1 | 11/2003 | Lesh |
| 6,761,708 B1* | 7/2004 | Chiu ............ A61M 25/0009 604/103.1 |
| 7,048,733 B2 | 5/2006 | Hartley |
| 7,344,543 B2 | 3/2008 | Sra |
| 7,581,328 B2 | 9/2009 | Greenhalgh et al. |
| 7,635,353 B2 | 12/2009 | Gurusamy |
| 7,654,970 B2 | 2/2010 | Dubey et al. |
| 7,666,203 B2 | 2/2010 | Chanduszko |
| 7,815,577 B2 | 10/2010 | Krishnan |
| 7,824,341 B2 | 11/2010 | Krishnan |
| 7,850,644 B2 | 12/2010 | Gonzalez |
| 7,976,551 B1 | 7/2011 | Gutfinger |
| 8,000,809 B2 | 8/2011 | Elencwajg |
| 8,019,404 B2 | 9/2011 | Kapadia |
| 8,029,470 B2 | 10/2011 | Whiting et al. |
| 8,114,110 B2 | 2/2012 | Bednarek |
| 8,172,757 B2 | 5/2012 | Jaffe |
| 8,235,986 B2 | 8/2012 | Kulesa |
| 8,317,810 B2 | 11/2012 | Stangenes |
| 8,694,077 B2 | 4/2014 | Kapadia |
| 8,771,297 B2 | 7/2014 | Miller et al. |
| 9,005,139 B2 | 4/2015 | Klaiman et al. |
| 9,339,230 B2 | 5/2016 | Kassab |
| 2002/0026175 A1 | 2/2002 | Paskar |
| 2002/0038129 A1 | 3/2002 | Peters et al. |
| 2002/0058960 A1* | 5/2002 | Hudson ............ A61B 17/0057 606/192 |
| 2002/0143291 A1 | 10/2002 | Slater |
| 2002/0169377 A1 | 11/2002 | Khairkhahan |
| 2003/0125709 A1 | 7/2003 | Eidenschink |
| 2003/0144657 A1 | 7/2003 | Bowe |
| 2004/0220471 A1 | 11/2004 | Schwartz |
| 2004/0225304 A1 | 11/2004 | Vidlund et al. |
| 2005/0101984 A1 | 5/2005 | Chanduszko et al. |
| 2005/0149097 A1 | 7/2005 | Regnell |
| 2005/0197623 A1* | 9/2005 | Leeflang .......... A61M 25/0144 604/95.04 |
| 2006/0064062 A1 | 3/2006 | Gurusamy et al. |
| 2006/0074398 A1 | 4/2006 | Whiting et al. |
| 2006/0276710 A1 | 12/2006 | Krishnan |
| 2007/0270741 A1 | 11/2007 | Hassett |
| 2008/0097398 A1 | 4/2008 | Mitelberg et al. |
| 2008/0140173 A1* | 6/2008 | Eskaros ................ A61M 25/10 623/1.11 |
| 2008/0161840 A1 | 7/2008 | Osiroff |
| 2009/0171276 A1 | 7/2009 | Bednarek et al. |
| 2009/0312755 A1 | 12/2009 | Thapliyal et al. |
| 2010/0022948 A1 | 1/2010 | Wilson |
| 2010/0168777 A1 | 7/2010 | Stangenes |
| 2011/0054487 A1 | 3/2011 | Farnan |
| 2011/0082538 A1 | 4/2011 | Dahlgren et al. |
| 2011/0251594 A1 | 10/2011 | Godin |
| 2011/0270239 A1 | 11/2011 | Werneth |
| 2011/0295107 A1 | 12/2011 | Kargar et al. |
| 2011/0313283 A1 | 12/2011 | Kapadia |
| 2012/0010503 A1* | 1/2012 | Mangiardi ............ A61M 25/10 600/435 |
| 2012/0065597 A1 | 3/2012 | Cohen |
| 2012/0179188 A1 | 7/2012 | Chanduszko |
| 2013/0123620 A1 | 5/2013 | Tekulve |
| 2013/0274784 A1 | 10/2013 | Lenker |
| 2014/0081302 A1 | 3/2014 | Thapliyal et al. |
| 2014/0309675 A1 | 10/2014 | Maisano et al. |
| 2014/0309679 A1 | 10/2014 | Maisano et al. |
| 2016/0100859 A1 | 4/2016 | Sapir et al. |

FOREIGN PATENT DOCUMENTS

| | | |
|---|---|---|
| WO | 2011/130456 | 10/2011 |
| WO | 2013/128461 | 9/2013 |
| WO | 2014/064694 A2 | 5/2014 |
| WO | 2014/170890 A1 | 10/2014 |

OTHER PUBLICATIONS

Written Opinion dated Sep. 30, 2014 in counterpart International Application No. PCT/IL2014/050338.
An International Search Report and Invitation to pay additional fees, dated Jan. 15, 2016, in PCT/IL2015/051026.
A Restriction Requirement, dated Jan. 21, 2016, in U.S. Appl. No. 14/287,523.
A non-final Office Action, dated Feb. 9, 2016, in U.S. Appl. No. 14/245,135.
An International Search Report and Written Opinion, dated Mar. 30, 2016, in PCT/IL2015/051026.
Communication dated Aug. 23, 2016 from the U.S. Patent and Trademark Office in counterpart U.S. Appl. No. 14/513,435.
Communication dated Jul. 21, 2016 from the U.S. Patent and Trademark Office in counterpart U.S. Appl. No. 14/287,523.
An International Search Report dated Jul. 21, 2014, which issued during the prosecution of Applicant's PCT/IL2014/050338.

* cited by examiner

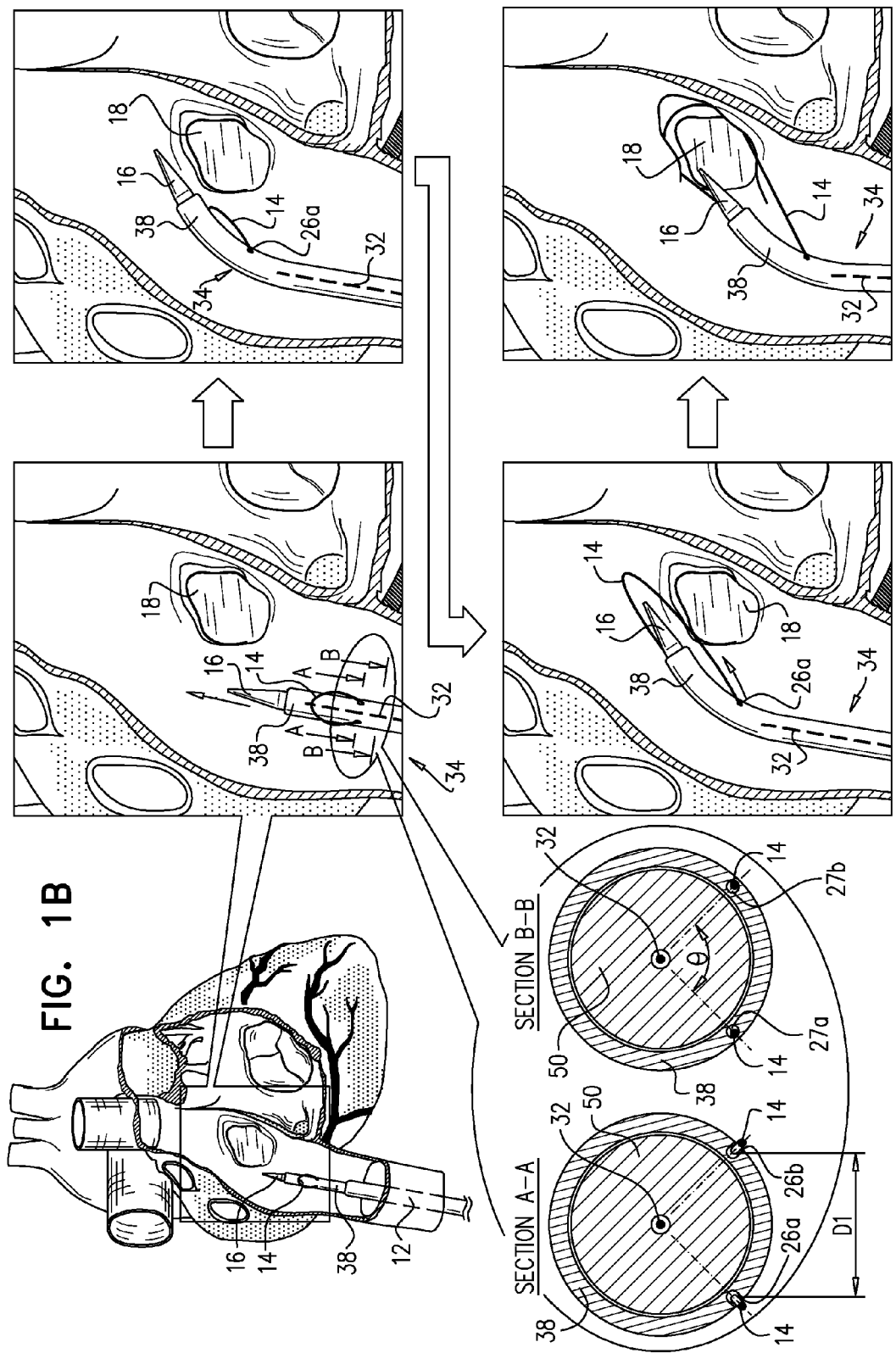

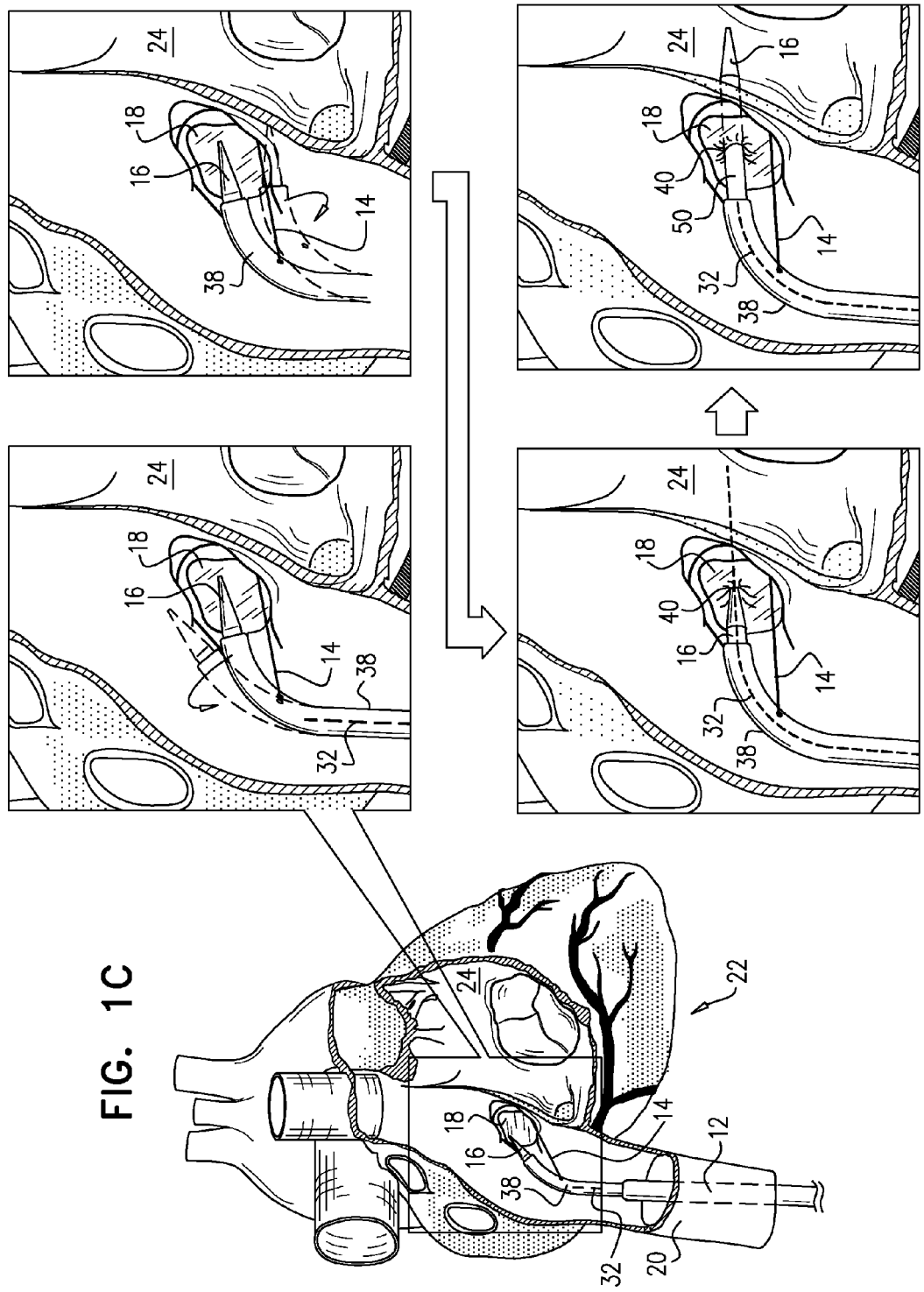

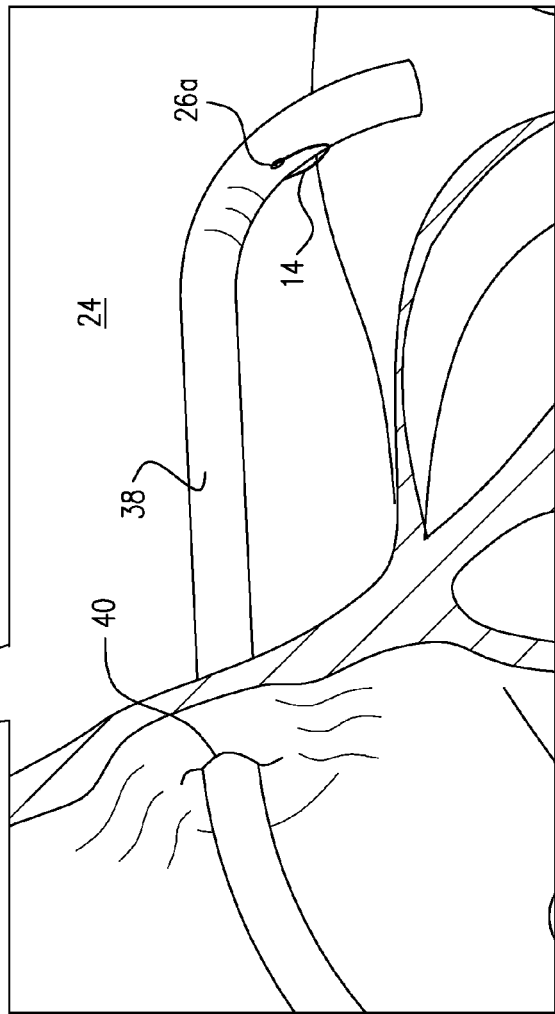
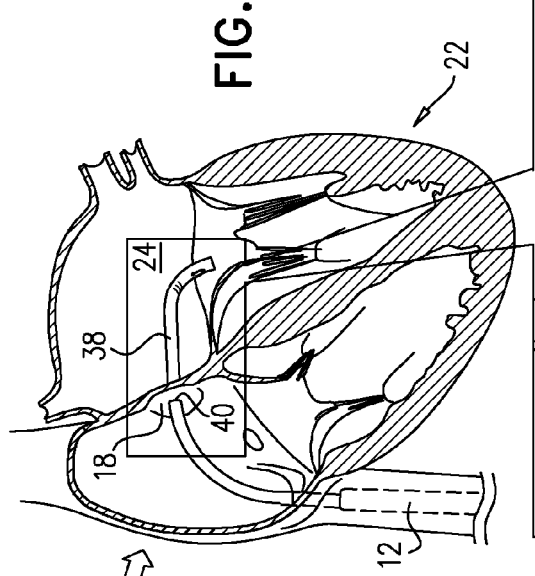
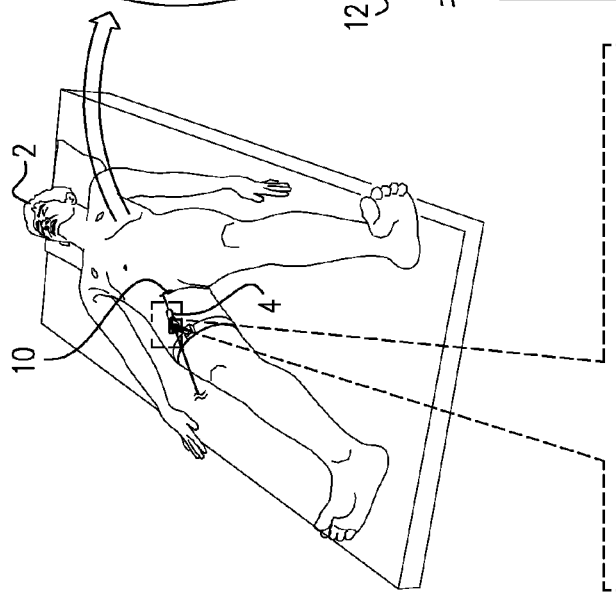
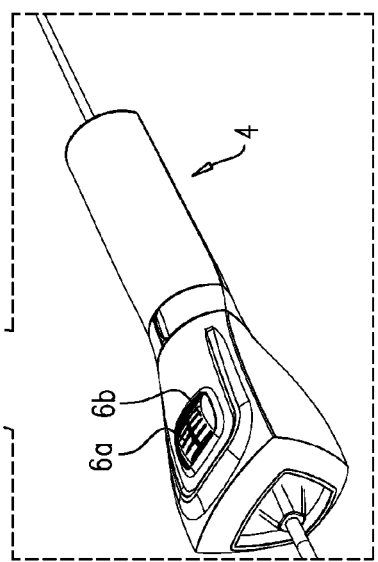
FIG. 1E

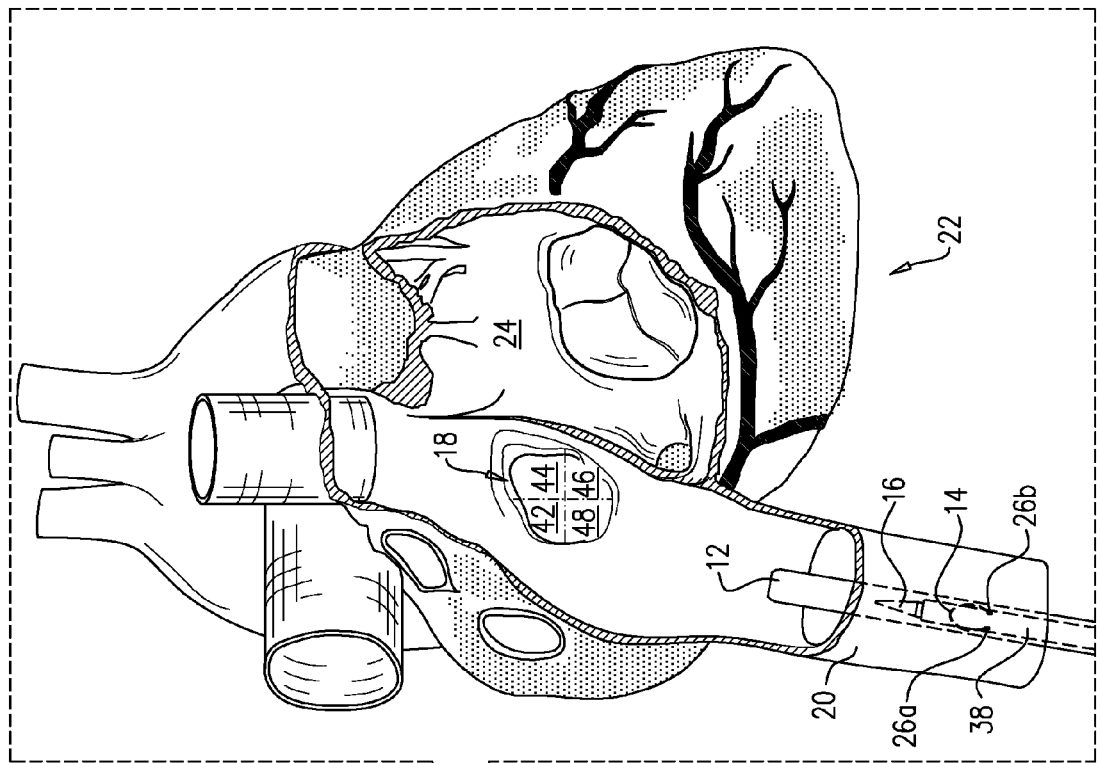
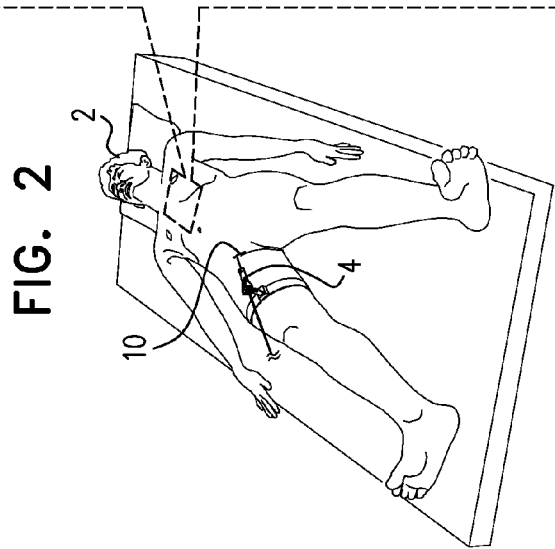
FIG. 2

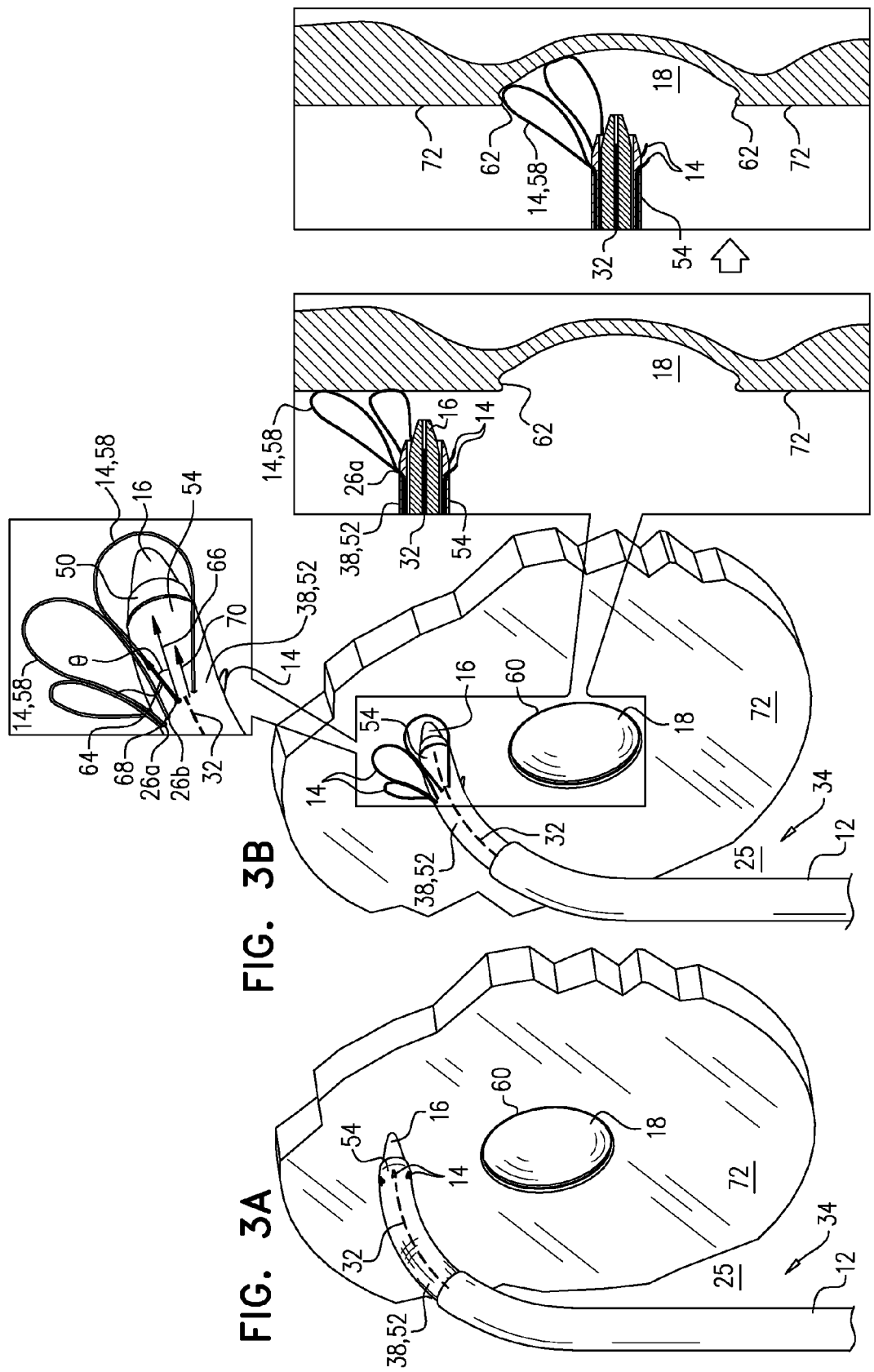

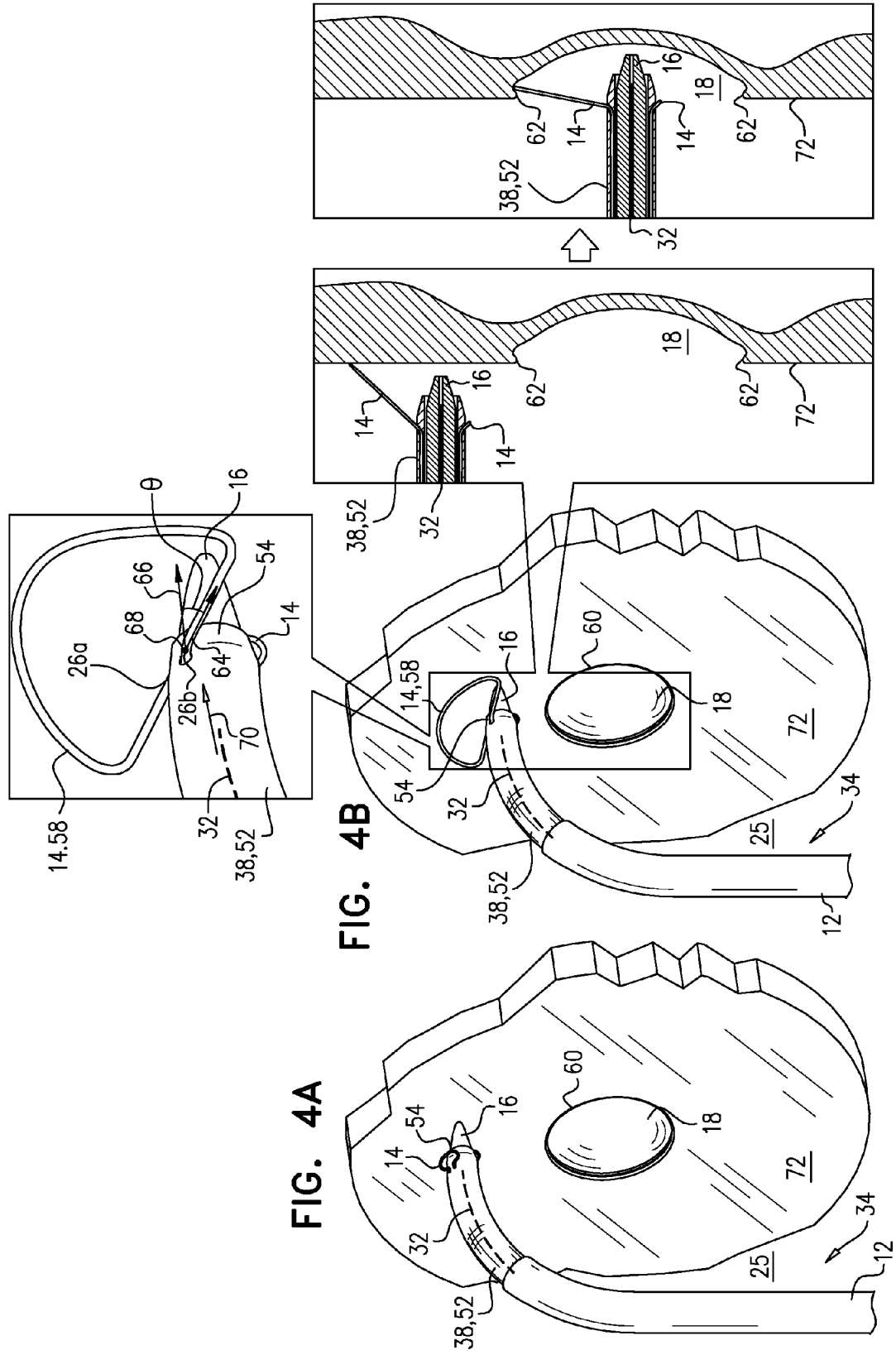

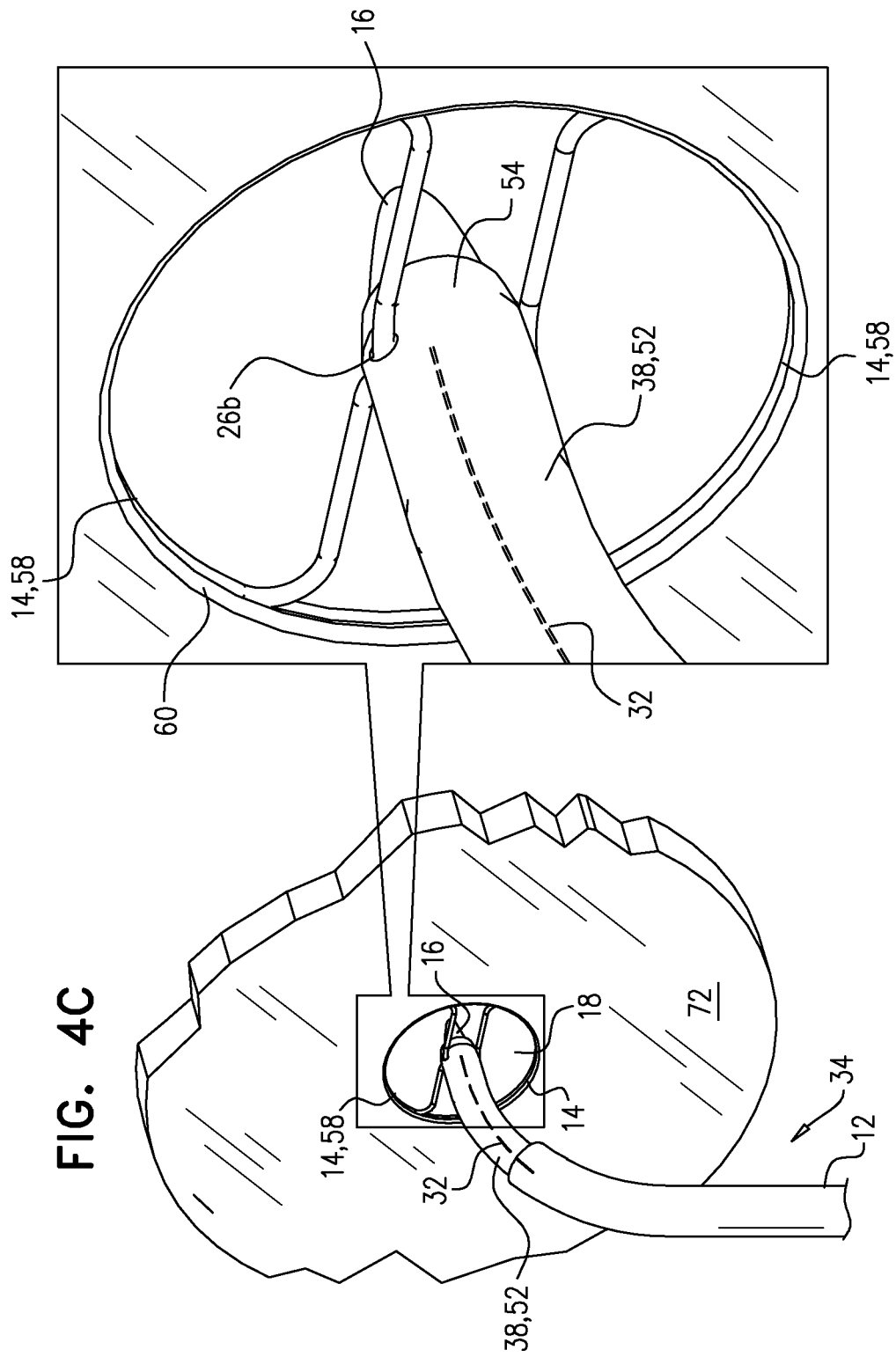

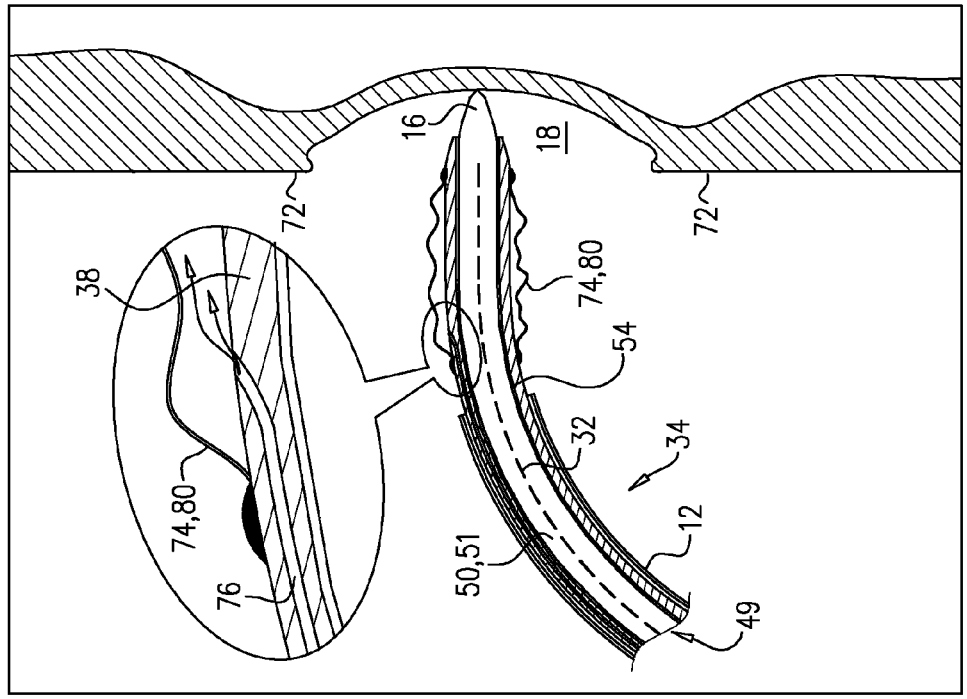
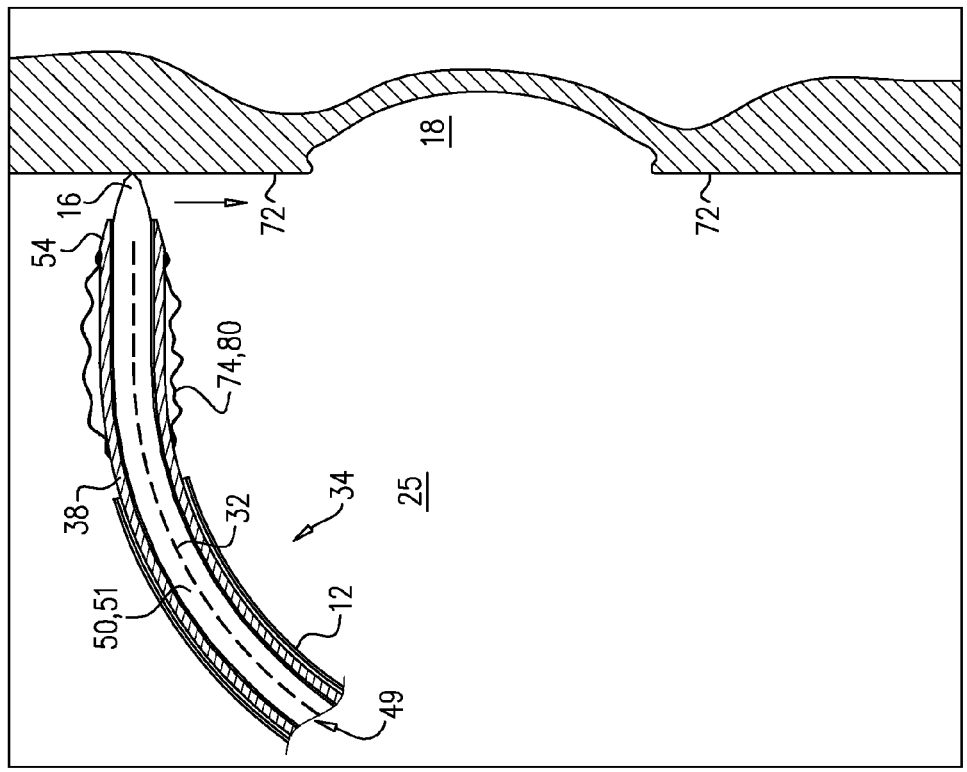

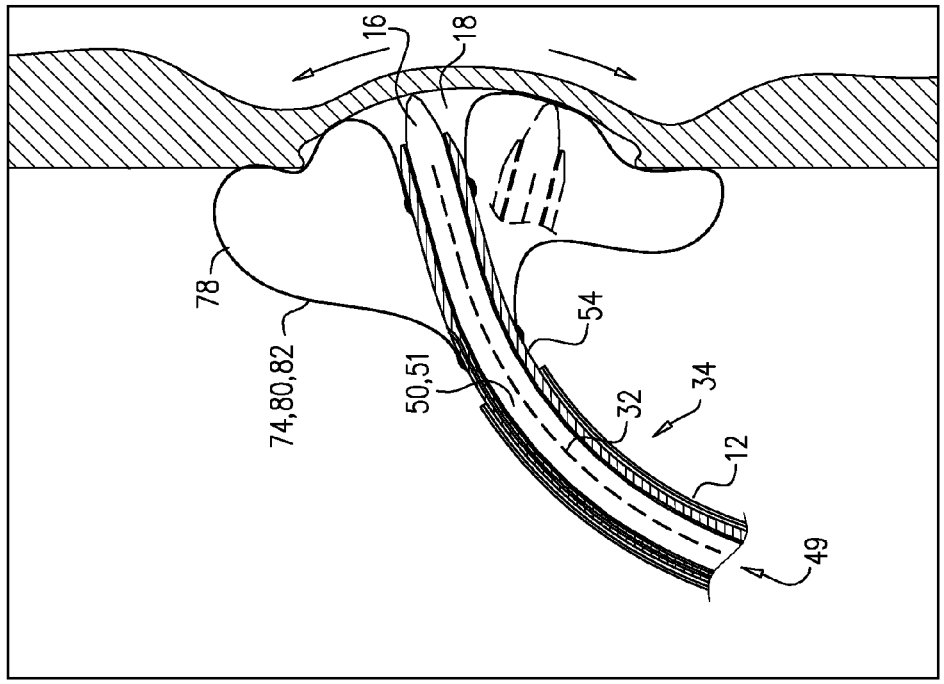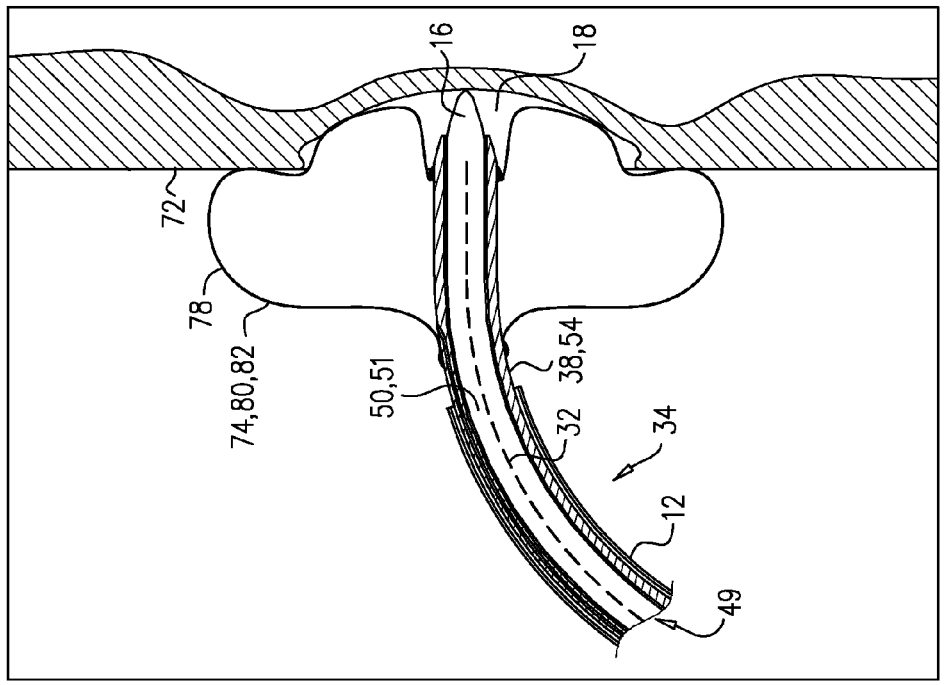

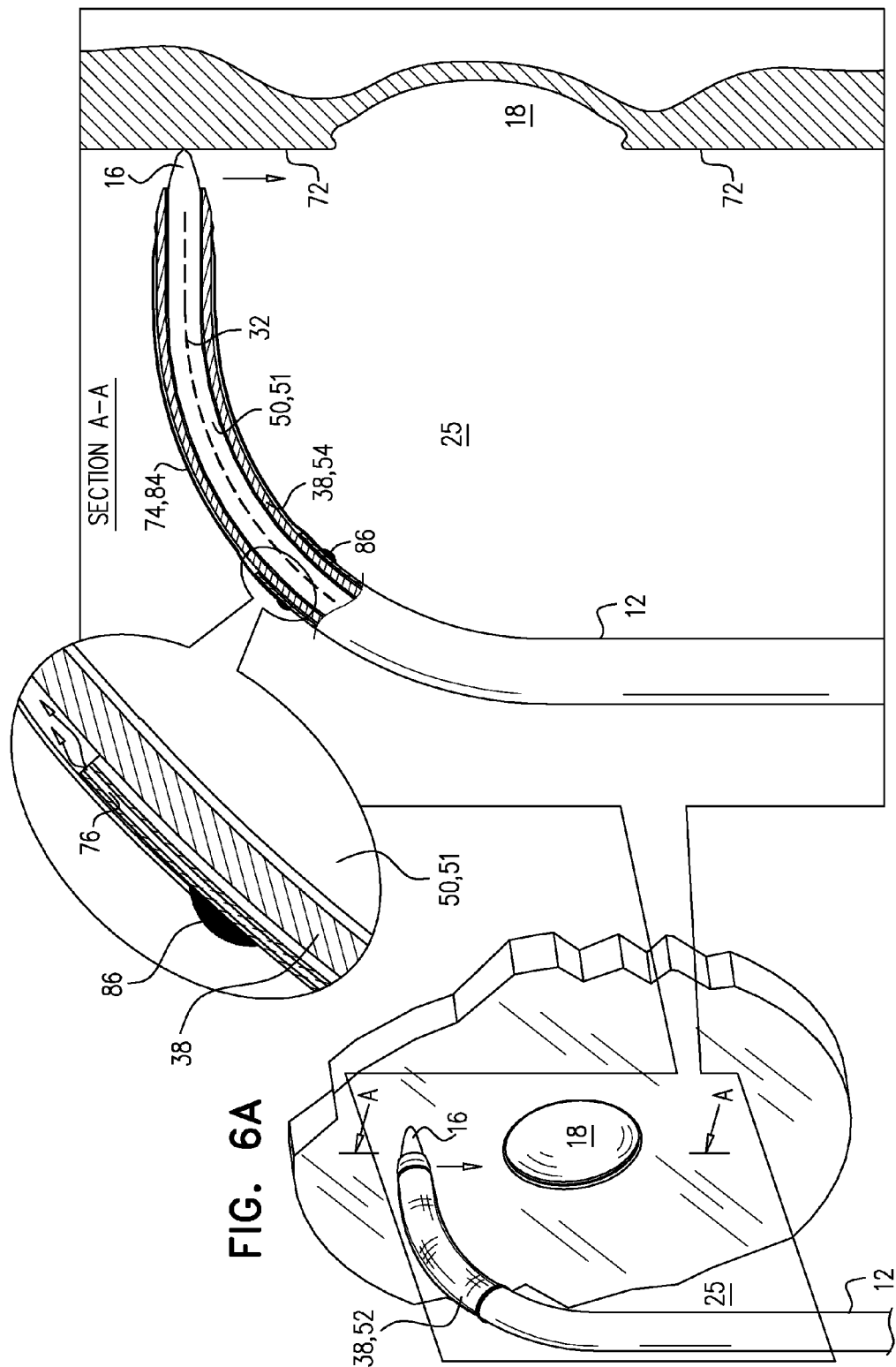

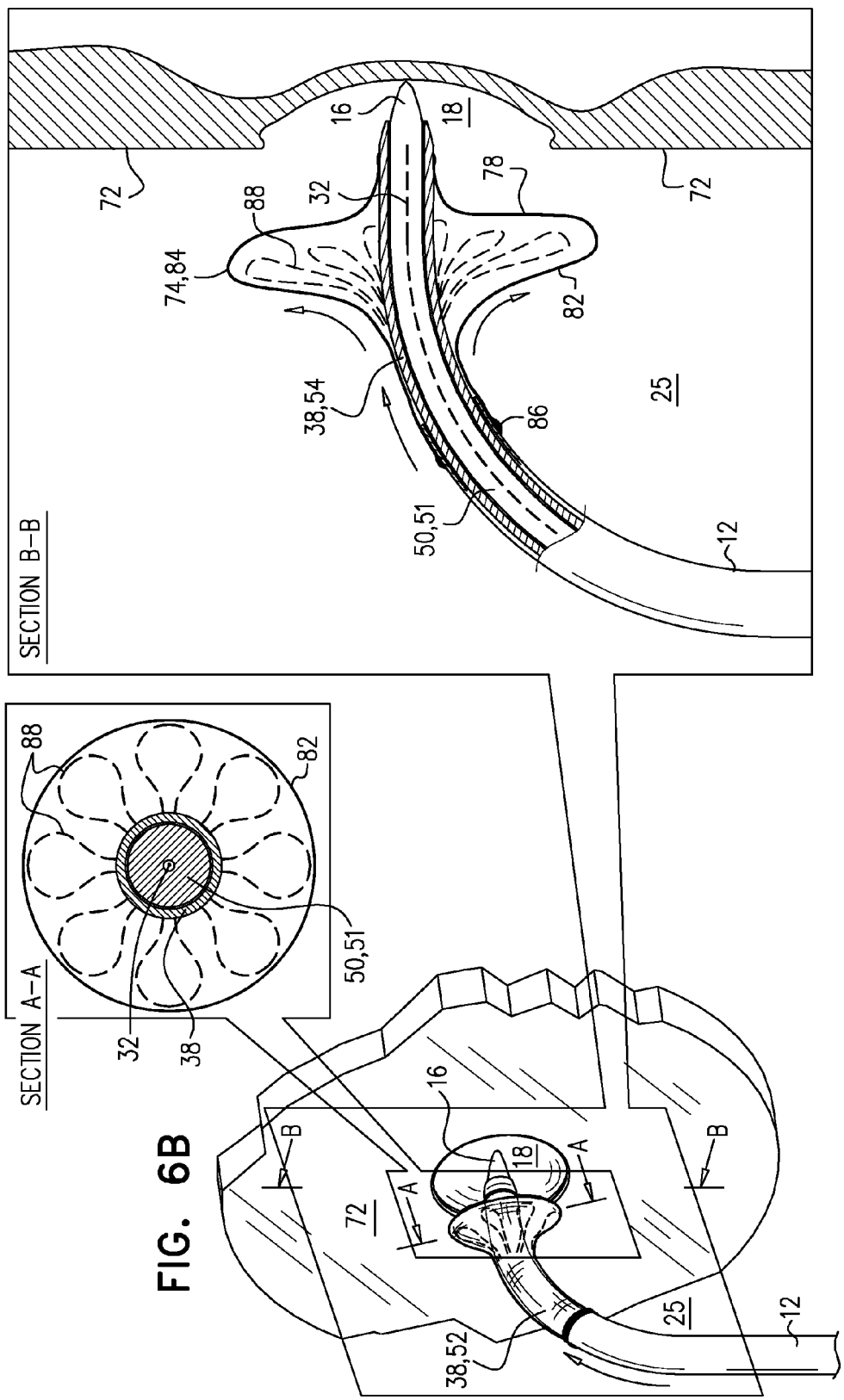

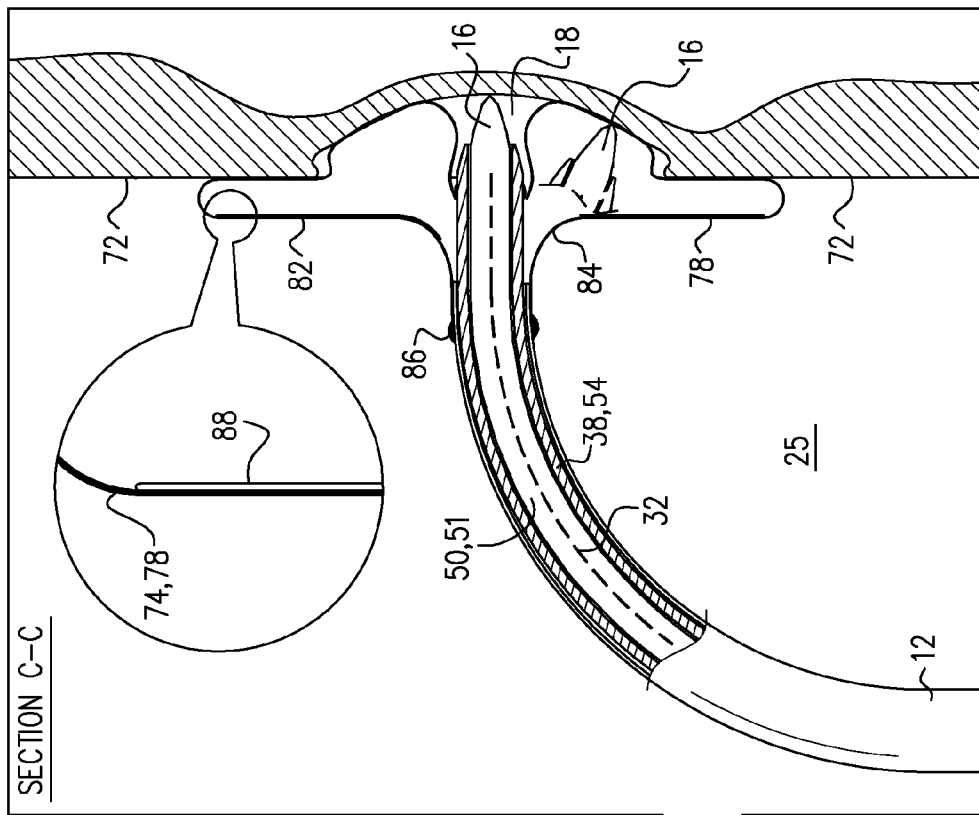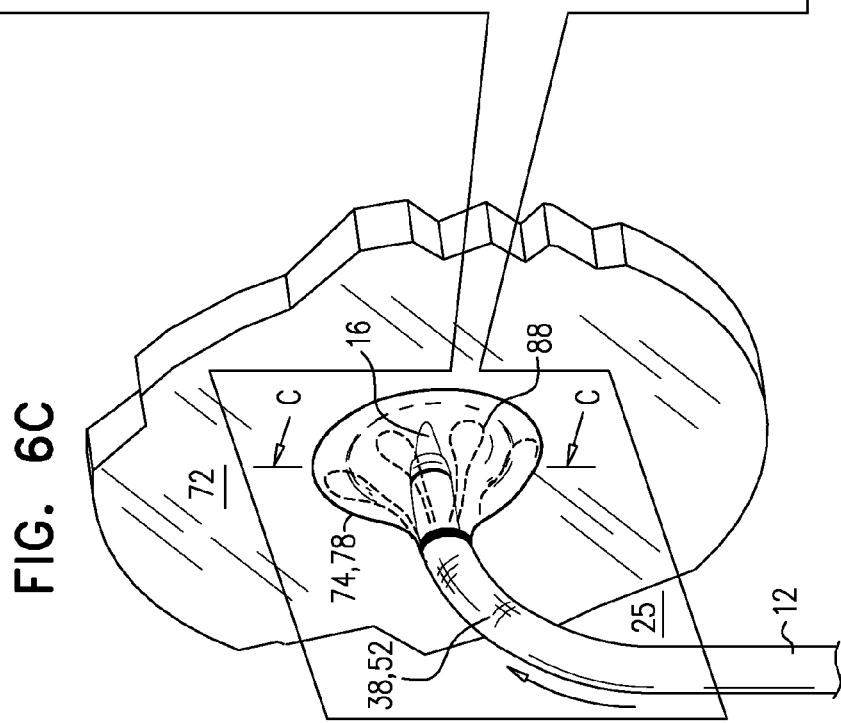
FIG. 6C

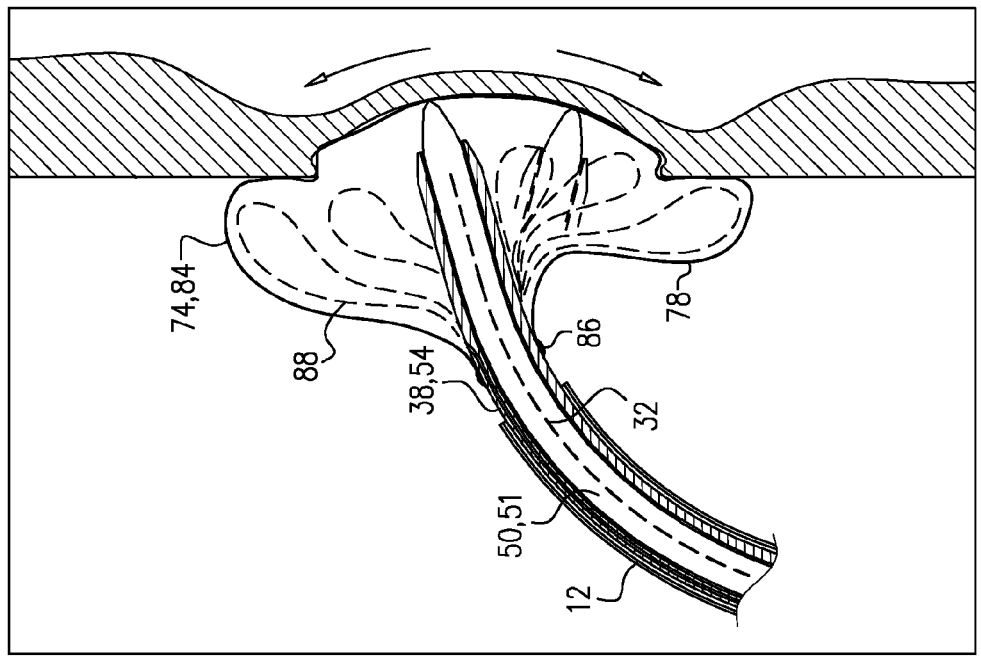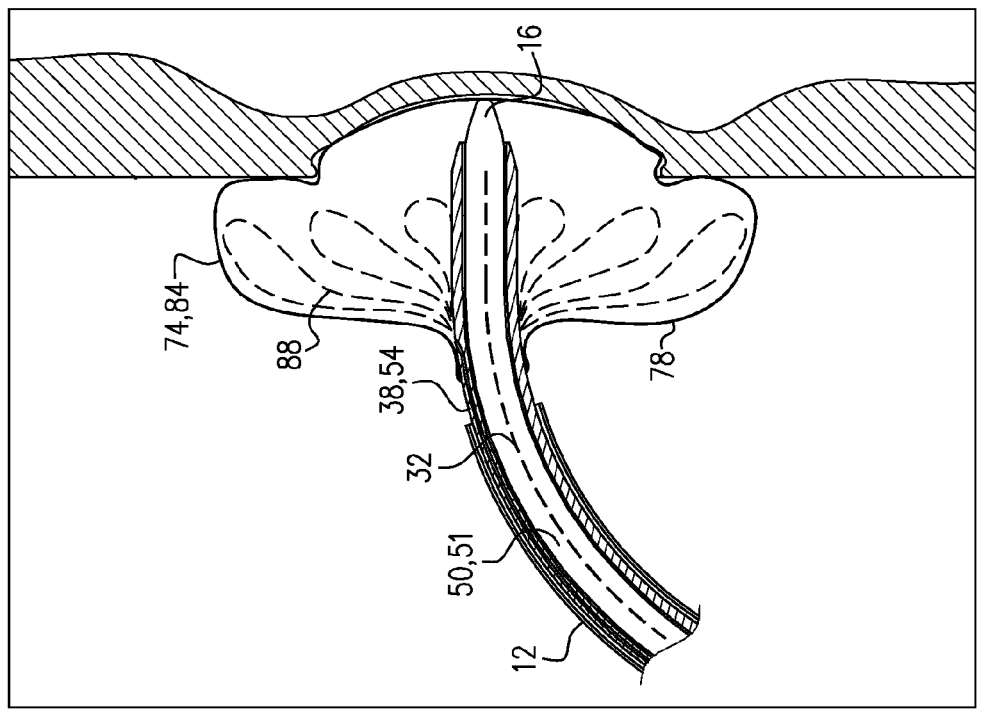

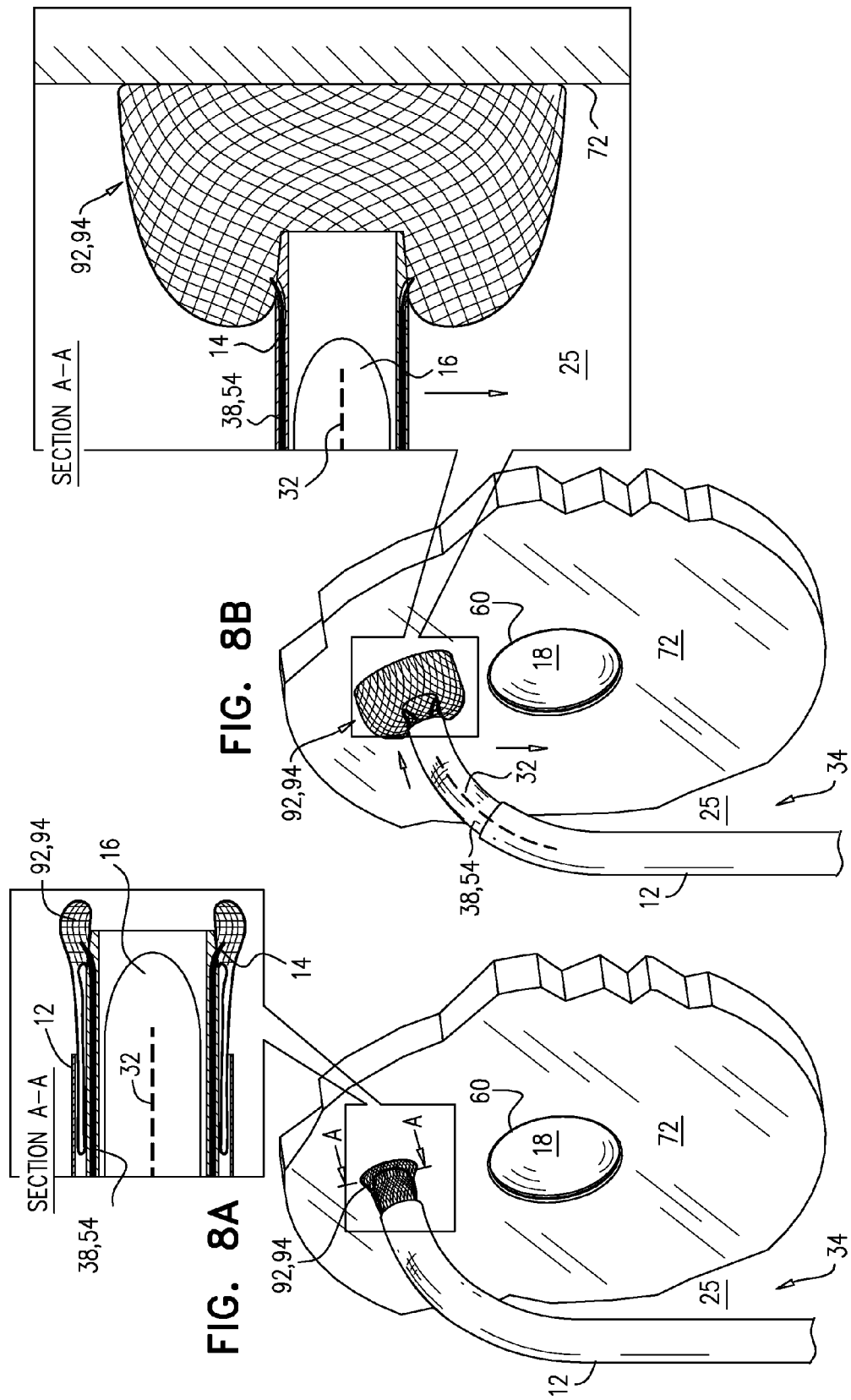

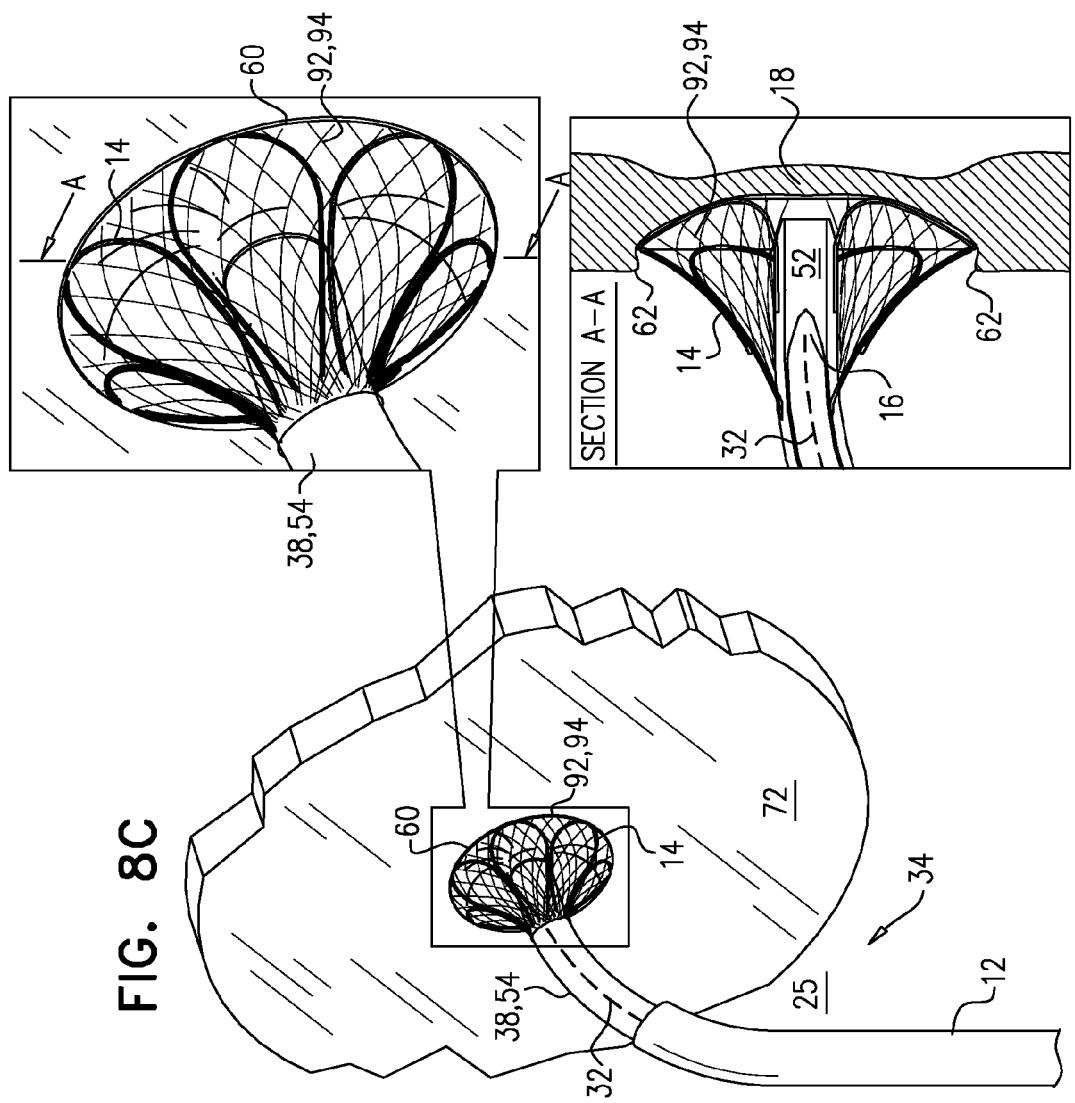

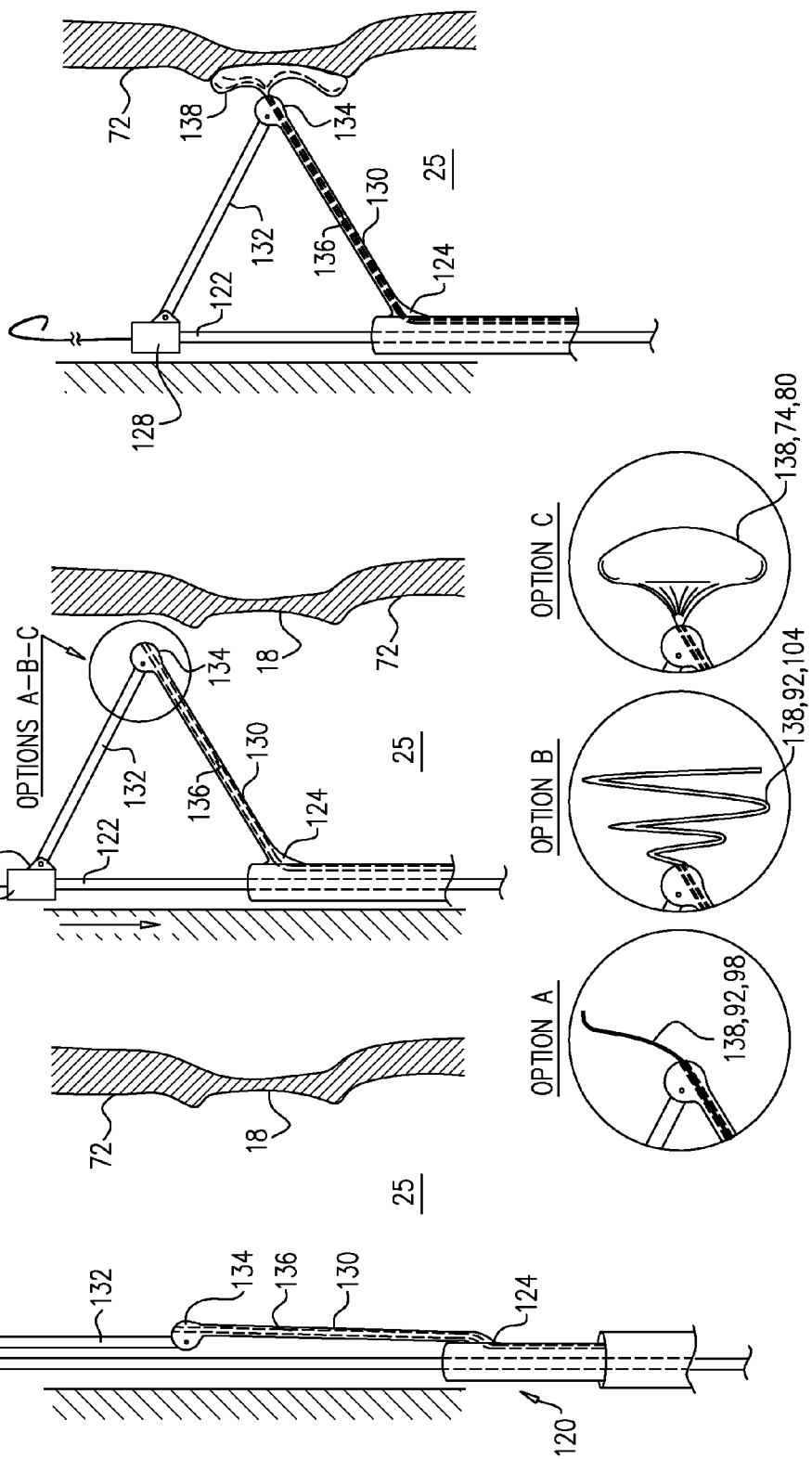

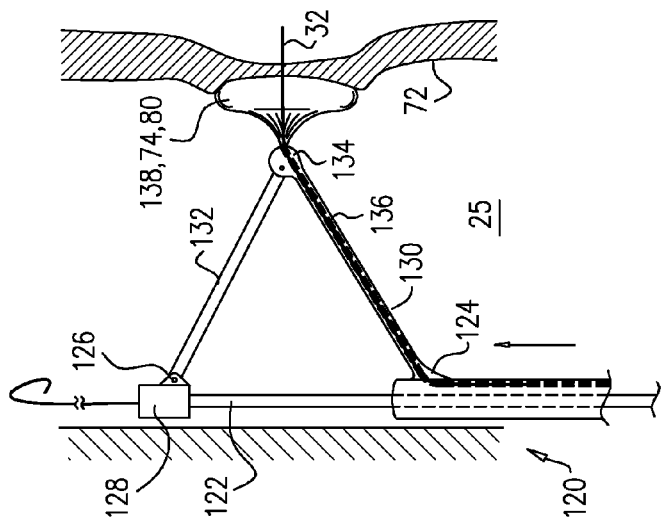
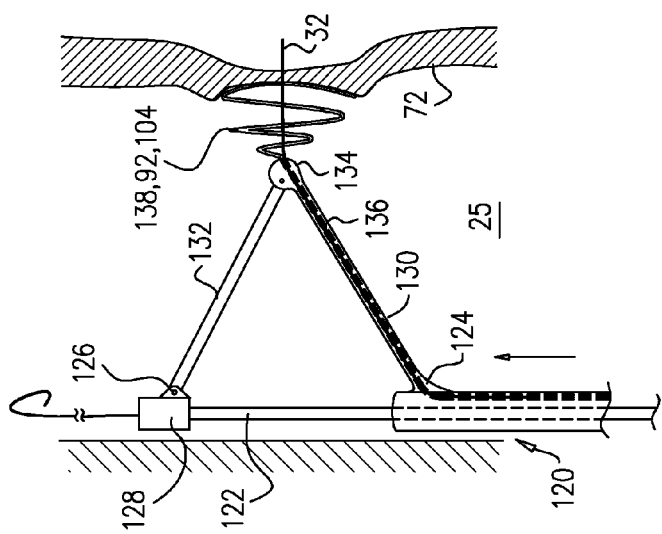
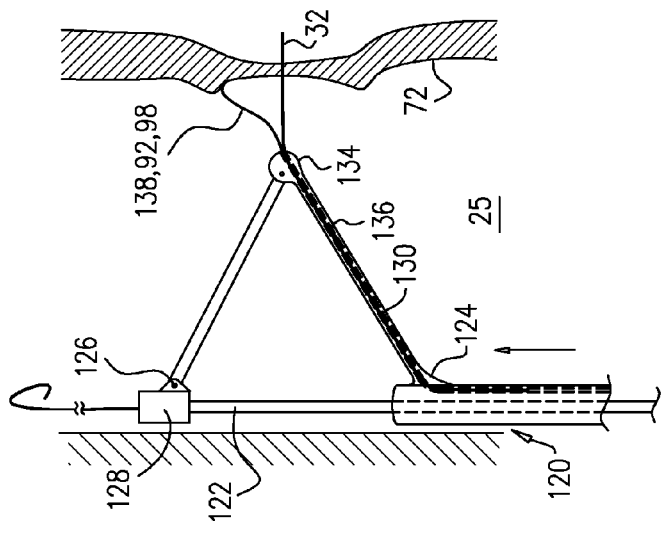

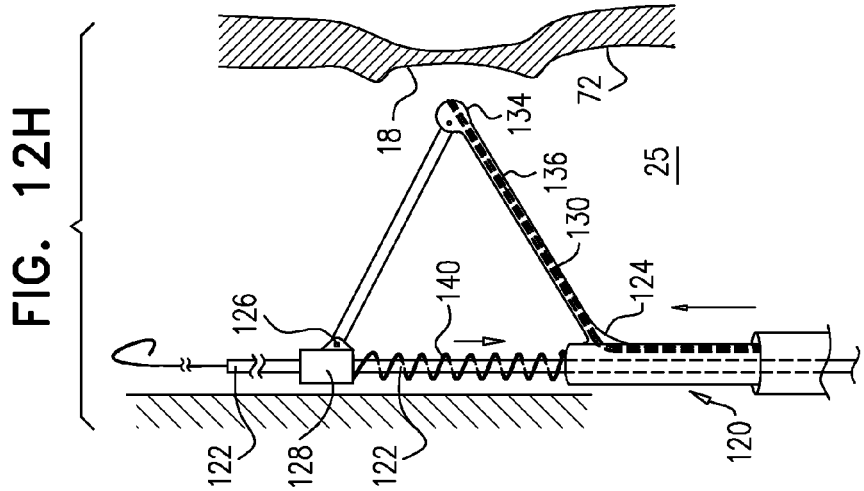
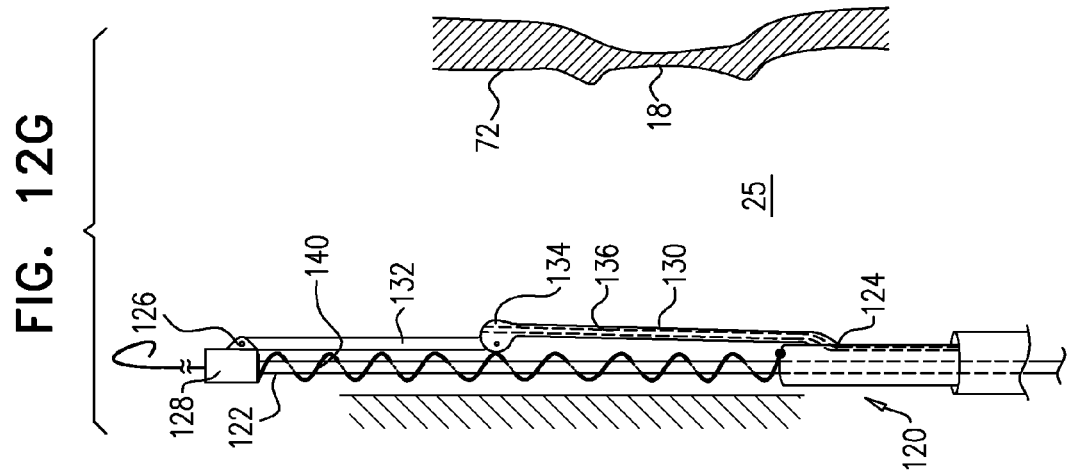

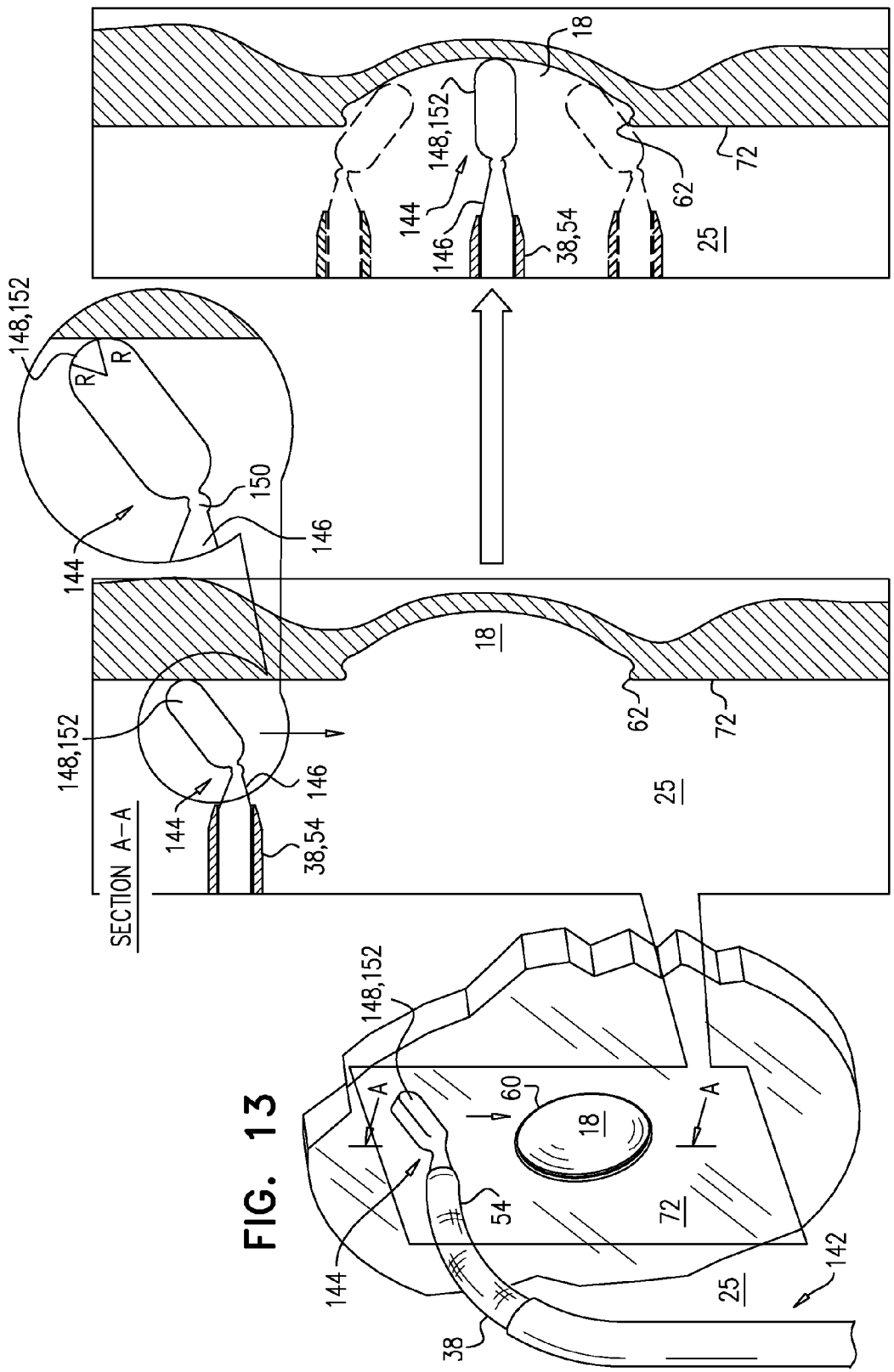

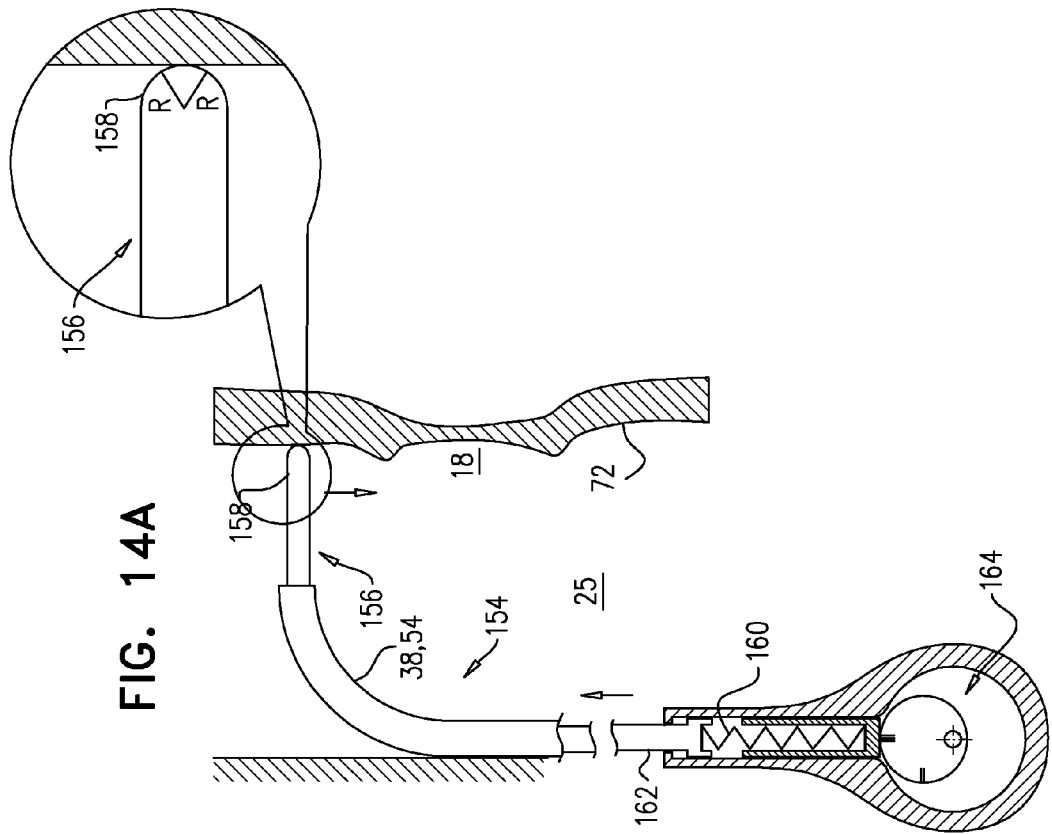

FOSSA OVALIS PENETRATION USING BALLOONS

CROSS-REFERENCE TO RELATED APPLICATIONS

The present application is a continuation-in-part of U.S. application Ser. No. 14/245,135, filed Apr. 4, 2014, entitled "Fossa Ovalis Penetration," which claims the benefit of U.S. Provisional Patent Application 61/811,947, filed Apr. 15, 2013.

The present application is also related to a US Regular Application entitled "Fossa Ovalis Penetration Using Probing Elements," filed on even date herewith.

Each of the above-referenced applications is assigned to the assignee of the present application and is incorporated herein by reference.

FIELD OF THE INVENTION

The present invention relates in general to apparatus and methods for delivering therapeutic devices to the left ventricle of the heart. More specifically, the present invention relates to apparatus and methods for penetrating the fossa ovalis for the purpose of delivering therapeutic devices.

BACKGROUND

Various pathologies call for the delivery of therapeutic devices, e.g., valve repair or valve replacement devices, to the left atrium or left ventricle of the heart (i.e., the left side of the heart). In many applications, therapeutic devices are delivered to the left side of the heart by being passed through the vena cava, into the right atrium, and through the interatrial septum. Such delivery calls for apparatus and methods for puncturing the interatrial septum. In many applications, the desired site for puncture lies in the fossa ovalis, a region of the septum containing tissue of lesser thickness than is typical of the rest of the septum.

SUMMARY OF THE INVENTION

Some applications of the present invention provide apparatus for puncturing the fossa ovalis of a heart. The apparatus comprises a catheter, and a puncturing element slidably disposed within the catheter lumen. The apparatus further comprises one or more flexible longitudinal members (e.g., wires), which, when deployed from the distal portion of the catheter, are typically loop-shaped. By contacting tissue at the perimeter of the fossa ovalis, the flexible longitudinal members facilitate the puncturing of the fossa ovalis by the puncturing element, e.g., by stabilizing the catheter prior to the puncturing.

There is therefore provided, in accordance with some applications of the present invention, apparatus for penetration of the fossa ovalis of a heart, the apparatus including:

a catheter shaped to define a catheter lumen, and at a distal portion of the catheter first and second openings;

a puncturing element slidably disposed within the catheter; and a flexible longitudinal member slidably passing through the first opening and slidably passing through the second opening.

In some applications, the apparatus further includes a dilator element slidably disposed within the catheter, the dilator element including a dilator body shaped to define a dilator lumen.

In some applications, the dilator element further includes a dilator tip disposed at the distal end of the dilator element.

In some applications, the puncturing element is slidably disposed within the dilator lumen.

There is further provided, in accordance with some applications of the present invention, apparatus for puncturing a fossa ovalis of a heart, the apparatus including:

a catheter shaped to define a catheter lumen;

a puncturing element slidably disposed within the catheter lumen, the puncturing element configured to be deployed from a distal portion of the catheter and to puncture the fossa ovalis; and one or more flexible longitudinal members slidably disposed within the catheter lumen and configured to:

be deployed from the distal portion of the catheter, and upon being deployed, facilitate the puncturing of the fossa ovalis by the puncturing element, by contacting tissue at a perimeter of the fossa ovalis.

In some applications, the one or more flexible longitudinal members are mechanically resilient.

In some applications, respective diameters of the one or more flexible longitudinal members are between 0.1 and 0.5 mm.

In some applications, the one or more flexible longitudinal members include one or more wires.

In some applications, the one or more flexible longitudinal members include a material selected from the group consisting of: nitinol, stainless steel, and chromium cobalt.

In some applications, the catheter is further shaped to define one or more openings at the distal portion thereof, the one or more flexible longitudinal members being configured to be deployed by being slidably passed through the one or more openings.

In some applications, the one or more flexible longitudinal members are configured to be deployed such that respective deployed portions of the flexible longitudinal members are shaped as loops.

In some applications, the one or more flexible longitudinal members are configured to contact the tissue at the perimeter of the fossa ovalis such that the puncturing element passes through at least one of the loops, before puncturing the fossa ovalis.

In some applications, the one or more flexible longitudinal members consist of a single flexible longitudinal member.

In some applications, each of the one or more flexible longitudinal members is configured to be deployed such that, in an absence of any force applied to the deployed portion of the flexible longitudinal member by an element that is not part of the apparatus, a deployment angle of the flexible longitudinal member is between 10 and 100 degrees, the deployment angle being an angle between (a) a vector that is (i) tangent to the flexible longitudinal member at an exit point of the flexible longitudinal member from the catheter, and (ii) directed away from the catheter, and (b) a distally-directed vector that is parallel to a longitudinal axis of the catheter at the exit point.

In some applications, each of the one or more flexible longitudinal members is configured to be deployed such that, in the absence of any force applied to the deployed portion of the flexible longitudinal member by an element that is not part of the apparatus, the deployment angle is between 10 and 80 degrees.

In some applications, each of the one or more flexible longitudinal members is configured to be deployed such that, in the absence of any force applied to the deployed portion of the flexible longitudinal member by an element that is not part of the apparatus, the deployment angle is between 30 and 60 degrees.

In some applications, the one or more flexible longitudinal members consist of one flexible longitudinal member.

In some applications, the one or more flexible longitudinal members consist of two flexible longitudinal members.

In some applications, the one or more flexible longitudinal members consist of three flexible longitudinal members.

In some applications, the one or more flexible longitudinal members consist of 4-6 flexible longitudinal members.

In some applications, each of the one or more flexible longitudinal members is configured to be deployed such that, in the absence of any force applied to the deployed portion of the flexible longitudinal member by an element that is not part of the apparatus, the deployment angle is between 85 and 95 degrees.

In some applications, the one or more flexible longitudinal members consist of two flexible longitudinal members.

In some applications, the one or more flexible longitudinal members are radiopaque.

In some applications, the apparatus further includes a plurality of radiopaque markers coupled to the one or more flexible longitudinal members.

In some applications, the apparatus further includes a dilator element slidably disposed within the catheter lumen, the dilator element including:
 a dilator body shaped to define a dilator lumen; and
 a dilator tip disposed at a distal end of the dilator element, the dilator tip being configured to dilate an opening created by the puncture of the fossa ovalis.

In some applications, the puncturing element is slidably disposed within the dilator lumen.

There is further provided, in accordance with some applications of the present invention, apparatus for puncturing a fossa ovalis of a heart, the apparatus including:
 a catheter shaped to define a catheter lumen; and
 a puncturing element slidably disposed within the catheter lumen, the puncturing element configured to be deployed from a distal portion of the catheter and to puncture the fossa ovalis,
 the apparatus being shaped to define one or more orifices configured to facilitate positioning of the puncturing element by directing a flow from the apparatus of one or more streams of a contrast agent at an angle of at least 10 degrees with respect to a distally-pointing vector that is parallel to a longitudinal axis of the catheter at the one or more orifices.

In some applications, the apparatus further includes a dilator element slidably disposed within the catheter lumen, the dilator element including:
 a dilator body shaped to define a dilator lumen; and
 a dilator tip disposed at a distal end of the dilator element, the dilator tip being configured to dilate an opening created by the puncture of the fossa ovalis.

In some applications, the puncturing element is slidably disposed within the dilator lumen.

There is further provided, in accordance with some applications of the present invention, apparatus for puncturing a fossa ovalis of a heart, the apparatus including:
 a catheter shaped to define a catheter lumen;
 a puncturing element slidably disposed within the catheter lumen and configured to (a) be deployed from a distal portion of the catheter, and (b) puncture the fossa ovalis; and
 a balloon configured to:
  be deployed from the distal portion of the catheter,
  be radially expanded, and
  upon being deployed and expanded, facilitate positioning of the puncturing element, by contacting at least a portion of the fossa ovalis.

In some applications, the apparatus further includes a dilator element slidably disposed within the catheter lumen, the dilator element including:
 a dilator body shaped to define a dilator lumen; and
 a dilator tip disposed at a distal end of the dilator element, the dilator tip being configured to dilate an opening created by the puncture of the fossa ovalis.

In some applications, the puncturing element is slidably disposed within the dilator lumen.

In some applications, the balloon includes an at least partially radiopaque surface.

In some applications, the balloon is a compliant balloon.

In some applications, the balloon is configured to not undergo plastic deformation when an internal pressure of the balloon is raised to 30 mmHg.

In some applications, the balloon is configured to not undergo plastic deformation when an internal pressure of the balloon is raised to 50 mmHg.

In some applications, at an internal pressure of the balloon of 30 mmHg, a volume of the balloon is less than 75% of a volume of the balloon at which the balloon begins to undergo plastic deformation.

In some applications, the balloon has a wall thickness of 25-100 microns.

In some applications, the apparatus further includes a contrast agent, and the balloon is configured to contain the contrast agent, upon being deployed and expanded.

In some applications, the balloon is an annular balloon, shaped to define a hole, the distal portion of the catheter passing through the hole.

In some applications, the balloon is configured to be generally shaped as a torus, upon being deployed and expanded.

In some applications, a maximum volume of the balloon is between 1 and 8 mL.

In some applications, a maximum volume of the balloon is between 1 and 5 mL.

In some applications, a maximum surface area of the balloon not in contact with any other element of the apparatus is between 450 and 2000 mm2.

In some applications, a maximum surface area of the balloon not in contact with any other element of the apparatus is between 500 and 1000 mm2.

In some applications, the balloon is a non-compliant balloon.

In some applications, the apparatus further includes:
 at least one slider disposed along an outer surface of the catheter; and
 a plurality of ribs coupled to the slider and to a surface of the balloon,
 the at least one slider and the plurality of ribs being configured to (a) facilitate expansion of the balloon, by the slider sliding from an initial position to a second position more distal than the initial position, and (b) maintain the expansion of the balloon, by the slider remaining in the second position.

In some applications, the balloon covers a distal tip of the catheter.

In some applications, the distal tip of the catheter is attached to an inner surface of the balloon.

In some applications, the puncturing element is configured to puncture the balloon immediately before puncturing the fossa ovalis.

In some applications, a maximum volume of the balloon is between 1 and 5 mL.

In some applications, a maximum surface area of the balloon not in contact with any other element of the apparatus is between 450 and 1400 mm2.

In some applications, a maximum surface area of the balloon not in contact with any other element of the apparatus is between 500 and 1000 mm2.

In some applications, upon being deployed and expanded, the balloon is configured to facilitate the positioning of the puncturing element, by filling a majority of the fossa ovalis.

There is further provided, in accordance with some applications of the present invention, apparatus for puncturing a fossa ovalis of a heart, the apparatus including:

a catheter shaped to define a catheter lumen;

a puncturing element slidably disposed within the catheter lumen, the puncturing element configured to be deployed from a distal portion of the catheter and to puncture the fossa ovalis; and a probing element configured to:

be deployed from the distal portion of the catheter, upon being deployed, probe (a) tissue near the fossa ovalis, the probing element being configured to have a first configuration thereof upon probing the tissue near the fossa ovalis, and (b) tissue of the fossa ovalis, and upon probing the tissue of the fossa ovalis, facilitate positioning of the puncturing element, by automatically adopting a second configuration thereof that is different from the first configuration.

In some applications, the apparatus further includes a dilator element slidably disposed within the catheter lumen, the dilator element including:

a dilator body shaped to define a dilator lumen; and a dilator tip disposed at a distal end of the dilator element, the dilator tip being configured to dilate an opening created by the puncture of the fossa ovalis.

In some applications, the puncturing element is slidably disposed within the dilator lumen.

In some applications, the probing element includes a flexible sheet.

In some applications, the flexible sheet includes a radiopaque pattern.

In some applications, the probing element includes a mesh.

In some applications, the mesh includes (a) a first group of longitudinal elements, respective diameters of each of which being between 0.05 and 0.125 mm, and (b) a second group of longitudinal elements, respective diameters of each of which being between 0.1 and 0.5 mm.

In some applications, an average distance of the second group of longitudinal elements from a center of mass of the mesh is at least 20% greater than an average distance of the first group of longitudinal elements from the center of mass, the center of mass being determined when the mesh is maximally flattened.

In some applications, the probing element includes a plurality of flexible longitudinal members configured to probe the tissue near the fossa ovalis by contacting the tissue with distal tips of the flexible longitudinal members.

In some applications, at least one of the flexible longitudinal members is configured to oppose movement of the probing element from the fossa ovalis, by pressing against a perimeter of the fossa ovalis.

In some applications, the distal tip of the at least one of the flexible longitudinal members is curved, in the absence of any force applied thereto.

In some applications, the probing element includes a spring configured to elongate upon probing the tissue of the fossa ovalis.

In some applications, the probing element includes a shape-memory material configured to facilitate the deployment of the probing element.

In some applications, the apparatus further includes one or more flexible longitudinal members slidably disposed within the catheter lumen and configured to:

be deployed from the distal portion of the catheter, and upon being deployed, facilitate the puncturing of the fossa ovalis by the puncturing element, by contacting tissue at a perimeter of the fossa ovalis.

In some applications, the one or more flexible longitudinal members are mechanically resilient.

In some applications, respective diameters of the one or more flexible longitudinal members are between 0.1 and 0.5 mm.

In some applications, the one or more flexible longitudinal members include one or more wires.

In some applications, the one or more flexible longitudinal members include a material selected from the group consisting of: nitinol, stainless steel, and chromium cobalt.

In some applications, the catheter is further shaped to define one or more openings at the distal portion thereof, the one or more flexible longitudinal members being configured to be deployed by being slidably passed through the one or more openings.

In some applications, each of the one or more flexible longitudinal members is configured to be deployed such that a deployed portion of the flexible longitudinal member is shaped as a loop.

In some applications, each of the one or more flexible longitudinal members is configured to be deployed such that, in an absence of any force applied to the deployed portion of the flexible longitudinal member by an element that is not part of the apparatus, a deployment angle of the flexible longitudinal member is between 10 and 80 degrees, the deployment angle being an angle between (a) a vector that is (i) tangent to the flexible longitudinal member at an exit point of the flexible longitudinal member from the catheter, and (ii) directed away from the catheter, and (b) a distally-directed vector that is parallel to a longitudinal axis of the catheter at the exit point.

In some applications, each of the one or more flexible longitudinal members is configured to be deployed such that, in the absence of any force applied to the deployed portion of the flexible longitudinal member by an element that is not part of the apparatus, the deployment angle is between 30 and 60 degrees.

In some applications, the one or more flexible longitudinal members consist of three flexible longitudinal members.

In some applications, the one or more flexible longitudinal members consist of six flexible longitudinal members.

In some applications, the probing element is radiopaque.

In some applications, the apparatus further includes a plurality of radiopaque markers coupled to the probing element.

There is further provided, in accordance with some applications of the present invention, apparatus for puncturing a fossa ovalis of a heart, the apparatus including:

a catheter shaped to define a catheter lumen;

a puncturing element slidably disposed within the catheter lumen, the puncturing element configured to be deployed from a distal portion of the catheter and to puncture the fossa ovalis; and a sensor including a probing element, the probing element being slidably disposed within the catheter lumen and configured to:
be deployed from the distal portion of the catheter, and
upon being deployed, probe tissue by applying a pushing force to the tissue,
the sensor being configured to facilitate positioning of the puncturing element by measuring the pushing force.

In some applications, the apparatus further includes a dilator element slidably disposed within the catheter lumen, the dilator element including:
a dilator body shaped to define a dilator lumen; and
a dilator tip disposed at a distal end of the dilator element, the dilator tip being configured to dilate an opening created by the puncture of the fossa ovalis.

In some applications, the puncturing element is slidably disposed within the dilator lumen.

In some applications, the sensor includes a load-cell sensor.

In some applications, the apparatus further includes an alert-generating mechanism configured to generate an alert when the pushing force measured by the sensor at a given region of tissue is indicative of the probing element probing tissue of the fossa ovalis.

In some applications, the sensor is further configured to facilitate positioning of the puncturing element by measuring a displacement of the probing element.

In some applications, the apparatus further includes an alert-generating mechanism configured to generate an alert when the pushing force and the displacement measured by the sensor at a given region of tissue are indicative of the probing element probing tissue of the fossa ovalis.

In some applications, the alert-generating mechanism is configured to generate the alert in response to a ratio of the displacement to the pushing force being higher at the given region of tissue, relative to a second region of tissue.

In some applications, the probing element includes a spring, the sensor being configured to measure the pushing force by measuring a compression of the spring.

There is further provided, in accordance with some applications of the present invention, apparatus for identifying a puncture site for puncturing a fossa ovalis of a heart, the apparatus including:
a shaft;
a first joint;
a second joint coupled to a distal portion of the shaft, the second joint being slidably disposed with respect to the first joint;
a first arm pivotably coupled, at a proximal portion thereof, to the first joint;
a second arm pivotably coupled:
at a proximal portion thereof, to the second joint, and
at a distal portion thereof, to a distal portion of the first arm,
an arm selected from the group consisting of: the first arm, and the second arm, being shaped to define a lumen thereof; and
a positioning-facilitating element configured to:
be deployed from the lumen of the selected arm, and
facilitate identifying the puncture site by:
contacting tissue near the fossa ovalis and tissue of the fossa ovalis, and
being repositionable, the slidable disposition of the second joint facilitating repositioning of the positioning-facilitating element.

In some applications, the positioning-facilitating element is radiopaque.

In some applications, the apparatus further includes a plurality of radiopaque markers coupled to the positioning-facilitating element.

In some applications, the positioning-facilitating element includes a probing element, the probing element being configured to:
probe (a) tissue near the fossa ovalis, the probing element having a first configuration thereof, upon probing tissue near the fossa ovalis, and (b) tissue of the fossa ovalis, and
facilitate positioning of the puncturing element, by automatically adopting a second configuration thereof that is different from the first configuration, upon probing the tissue of the fossa ovalis.

In some applications, the probing element includes a plurality of flexible longitudinal members.

In some applications, the probing element includes a spring configured to elongate upon probing the tissue of the fossa ovalis.

In some applications, the positioning-facilitating element includes a balloon.

In some applications, the balloon is a compliant balloon.

In some applications, the apparatus further includes a puncturing element configured to:
be deployed from the lumen of the selected arm, and
puncture the fossa ovalis at the identified puncture site.

In some applications, the apparatus further includes a spring, and the second joint is configured to be slid with respect to the first joint by means of a change in a length of the spring.

There is further provided, in accordance with some applications of the present invention, apparatus for identifying a puncture site for puncturing a fossa ovalis of a heart, the apparatus including:
a catheter shaped to define a catheter lumen; and
a probing element slidably disposed within the catheter lumen, the probing element including:
a body; and
a blunt head pivotably coupled to the body, a radius of curvature of a distal portion of the blunt head being between 1 and 3 mm.

In some applications, the radius of curvature of the distal portion of the blunt head is between 1.3 and 1.6 mm.

In some applications, the apparatus further includes a hinge, and the blunt head is pivotably coupled to the body via the hinge.

In some applications, the blunt head includes a radiopaque blunt head.

In some applications, the apparatus further includes one or more radiopaque markers coupled to the blunt head.

There is further provided, in accordance with some applications of the present invention, apparatus for identifying a puncture site for puncturing a fossa ovalis of a heart, the apparatus including:
a catheter shaped to define a catheter lumen;
a pushing element including a blunt head, a radius of curvature of a distal portion of the blunt head being between 1 and 3 mm, the pushing element being slidably disposed within the catheter lumen and configured to:
be deployed from a distal portion of the catheter,
upon being deployed, facilitate identifying the puncture site by pushing against tissue at a plurality of sites; and
a spring coupled to a proximal portion of the pushing element, the spring being configured to facilitate:
the pushing by the pushing element, by the spring being compressed to a compressed position, and
retracting of the pushing element, by the spring being released from the compressed position.

In some applications, the radius of curvature of the distal portion of the blunt head is between 1.3 and 1.6 mm.

There is further provided, in accordance with some applications of the present invention, a method for puncturing a fossa ovalis of a heart, the method including:
  inserting a catheter into a right atrium of the heart;
  advancing the catheter toward an interatrial septum of the heart;
  sliding a flexible longitudinal member through openings disposed at a distal portion of the catheter, such that the flexible longitudinal member is made to loop around an inside perimeter of the fossa ovalis; and
  while the flexible longitudinal member is looped around the inside perimeter of the fossa ovalis, puncturing a hole in the fossa ovalis at a puncturing point, by sliding a puncturing element through the fossa ovalis.

There is further provided, in accordance with some applications of the present invention, a method for puncturing a fossa ovalis of a heart, the method including:
  inserting a catheter into a right atrium of the heart;
  advancing a distal portion of the catheter toward an interatrial septum of the heart;
  deploying a set of one or more flexible longitudinal members from the distal portion of the catheter, such that respective deployed portions of the one or more flexible longitudinal members of the set are shaped as loops;
  moving at least one of the flexible longitudinal members of the set along a surface of the interatrial septum, until the at least one of the flexible longitudinal members of the set contacts the fossa ovalis; and
  while the at least one of the flexible longitudinal members of the set is contacting the fossa ovalis, using a puncturing element to puncture the fossa ovalis.

In some applications, moving the at least one of the flexible longitudinal members of the set along a surface of the interatrial septum includes moving the at least one of the flexible longitudinal members of the set toward the fossa ovalis from below the fossa ovalis.

In some applications, using the puncturing element to puncture the fossa ovalis includes:
  passing the puncturing element through at least one of the loops; and
  subsequently to passing the puncturing element through the at least one of the loops, puncturing the fossa ovalis.

In some applications, the method further includes, while the at least one of the flexible longitudinal members of the set is contacting the fossa ovalis, and before the puncturing of the fossa ovalis:
  by pushing against the fossa ovalis with at least one of the at least one of the flexible longitudinal members of the set, steering the distal portion of the catheter toward a desired puncture site,
  and puncturing the fossa ovalis includes sliding the puncturing element (a) from the distal portion of the catheter, and (b) through the fossa ovalis, at the desired puncture site.

In some applications, steering the distal portion of the catheter includes adjusting a length of the deployed portion of the at least one of the at least one of the flexible longitudinal members of the set.

In some applications, the method further includes, while the at least one of the flexible longitudinal members of the set is contacting the fossa ovalis, and before the puncturing of the fossa ovalis, adjusting an orientation of the distal portion of the catheter, by using at least one of the at least one of the flexible longitudinal members of the set as a pivot, and puncturing the fossa ovalis includes sliding the puncturing element:
  from the distal portion of the catheter, and
  through the fossa ovalis, at an angle with respect to the fossa ovalis that is determined by the orientation of the distal portion of the catheter.

In some applications, using the at least one of the at least one of the flexible longitudinal members of the set as a pivot includes adjusting a length of the deployed portion of the at least one of the at least one of the flexible longitudinal members of the set.

In some applications, using the puncturing element to puncture the fossa ovalis includes using the puncturing element to puncture the fossa ovalis while at least two flexible longitudinal members of the set are contacting the fossa ovalis.

In some applications, using the puncturing element to puncture the fossa ovalis includes using the puncturing element to puncture the fossa ovalis while at least three flexible longitudinal members of the set are contacting the fossa ovalis.

In some applications, deploying the set of one or more flexible longitudinal members from the distal portion of the catheter includes slidably passing each of the one or more flexible longitudinal members of the set through one or more openings at the distal portion of the catheter.

In some applications, the method further includes stabilizing the catheter by pressing the at least one of the flexible longitudinal members of the set against a perimeter of the fossa ovalis, before puncturing the fossa ovalis.

In some applications, deploying the set of one or more flexible longitudinal members includes deploying exactly one flexible longitudinal member.

In some applications, deploying the set of one or more flexible longitudinal members includes deploying exactly two flexible longitudinal members.

In some applications, deploying the set of one or more flexible longitudinal members includes deploying exactly three flexible longitudinal members.

In some applications, deploying the set of one or more flexible longitudinal members includes deploying each of the flexible longitudinal members of the set such that a deployment angle of the flexible longitudinal member is between 10 and 100 degrees,
  the deployment angle being an angle between (a) a vector that is (i) tangent to the flexible longitudinal member at an exit point of the flexible longitudinal member from the catheter, and (ii) directed away from the catheter, and (b) a distally-directed vector that is parallel to a longitudinal axis of the catheter at the exit point.

In some applications, deploying the set of one or more flexible longitudinal members includes deploying each of the flexible longitudinal members of the set such that the deployment angle is between 10 and 80 degrees.

In some applications, deploying the set of one or more flexible longitudinal members includes deploying each of the flexible longitudinal members of the set such that the deployment angle is between 30 and 60 degrees.

In some applications, the set is a first set, and the method further includes:
  while the at least one of the flexible longitudinal members of the first set is contacting the fossa ovalis, and before the puncturing of the fossa ovalis:
    deploying a second set of one or more flexible longitudinal members from the distal portion of the catheter such that a deployed portion of each of the one or more flexible longitudinal members of the second set is shaped as a loop; and contacting the fossa ovalis with at least one of the flexible longitudinal members of the second set, the second set not including any flexible longitudinal members of the first set.

In some applications, the method further includes, while the at least one of the flexible longitudinal members of the second set is contacting the fossa ovalis, and before the puncturing of the fossa ovalis:

by pushing against the fossa ovalis with at least one of the at least one of the flexible longitudinal members of the second set, steering the distal portion of the catheter toward a desired puncture site, and puncturing the fossa ovalis includes sliding the puncturing element (a) from the distal portion of the catheter, and (b) through the fossa ovalis, at the desired puncture site.

In some applications, steering the distal portion of the catheter includes adjusting a length of the deployed portion of the at least one of the at least one of the flexible longitudinal members of the second set.

In some applications, the method further includes, while the at least one of the flexible longitudinal members of the second set is contacting the fossa ovalis, and before the puncturing of the fossa ovalis, adjusting an orientation of the distal portion of the catheter, by using at least one of the at least one of the flexible longitudinal members of the second set as a pivot, and puncturing the fossa ovalis includes sliding the puncturing element:

from the distal portion of the catheter, and through the fossa ovalis, at an angle with respect to the fossa ovalis that is determined by the orientation of the distal portion of the catheter.

In some applications, using the at least one of the at least one of the flexible longitudinal members of the second set as a pivot includes adjusting a length of the deployed portion of the at least one of the at least one of the flexible longitudinal members of the second set.

In some applications, contacting the fossa ovalis with the at least one of the flexible longitudinal members of the second set includes contacting the fossa ovalis with at least two flexible longitudinal members of the second set.

In some applications, contacting the fossa ovalis with the at least two of the flexible longitudinal members of the second set includes contacting the fossa ovalis with at least three flexible longitudinal members of the second set.

In some applications, deploying the second set of one or more flexible longitudinal members from the distal portion of the catheter includes slidably passing each of the one or more flexible longitudinal members of the second set through one or more openings at the distal portion of the catheter.

In some applications, the method further includes stabilizing the catheter by pressing the at least one of the flexible longitudinal members of the second set against a perimeter of the fossa ovalis, before puncturing the fossa ovalis.

In some applications, deploying the second set of one or more flexible longitudinal members includes deploying exactly one flexible longitudinal member.

In some applications, deploying the second set of one or more flexible longitudinal members includes deploying exactly two flexible longitudinal members.

In some applications, deploying the second set of one or more flexible longitudinal members includes deploying exactly three flexible longitudinal members.

In some applications, deploying the second set of one or more flexible longitudinal members includes deploying each of the flexible longitudinal members of the second set such that a deployment angle of the flexible longitudinal member is between 10 and 100 degrees, the deployment angle being an angle between (a) a vector that is (i) tangent to the flexible longitudinal member at an exit point of the flexible longitudinal member from the catheter, and (ii) directed away from the catheter, and (b) a distally-directed vector that is parallel to a longitudinal axis of the catheter at the exit point.

In some applications, deploying the second set of one or more flexible longitudinal members includes deploying each of the flexible longitudinal members of the second set such that the deployment angle is between 10 and 80 degrees.

In some applications, deploying the second set of one or more flexible longitudinal members includes deploying each of the flexible longitudinal members of the second set such that the deployment angle is between 30 and 60 degrees.

In some applications, deploying the set of one or more flexible longitudinal members includes deploying each of the flexible longitudinal members of the set such that a deployment angle of the flexible longitudinal member is between 85 and 95 degrees, the deployment angle being an angle between (a) a vector that is (i) tangent to the flexible longitudinal member at an exit point of the flexible longitudinal member from the catheter, and (ii) directed away from the catheter, and (b) a distally-directed vector that is parallel to a longitudinal axis of the catheter at the exit point.

In some applications, deploying the set of one or more flexible longitudinal members includes deploying exactly two flexible longitudinal members.

In some applications, deploying the set of one or more flexible longitudinal members includes deploying one or more radiopaque flexible longitudinal members, and the method further includes using fluoroscopic imaging to view the radiopaque flexible longitudinal members during and after deployment thereof.

In some applications, deploying the set of one or more flexible longitudinal members includes deploying one or more flexible longitudinal members coupled to one or more radiopaque markers, and the method further includes using fluoroscopic imaging to view the radiopaque markers during and after deployment of the flexible longitudinal members.

There is further provided, in accordance with some applications of the present invention, a method for puncturing a fossa ovalis of a heart, the method including:

inserting a catheter into a right atrium of the heart;

advancing a distal portion of the catheter toward an interatrial septum of the heart;

identifying a desired puncture site for puncturing the fossa ovalis, by:

positioning the distal portion of the catheter near a potential puncture site, releasing one or more streams of a contrast agent from the distal portion of the catheter at an angle of at least 10 degrees with respect to a distally-pointing vector that is parallel to a longitudinal axis of the catheter at a point of the release of the one or more streams, using imaging, viewing a pattern of flow of the contrast agent, and identifying that the potential puncture site is the desired puncture site, in response to the viewing; and using a puncturing element, puncturing the fossa ovalis at the desired puncture site.

There is further provided, in accordance with some applications of the present invention, a method for puncturing a fossa ovalis of a heart, the method including:

inserting a catheter into a right atrium of the heart;

advancing a distal portion of the catheter toward an interatrial septum of the heart;

deploying a balloon from the distal portion of the catheter;

identifying a puncture site for puncturing the fossa ovalis, in response to a manner in which the balloon contacts the septum; and using a puncturing element, puncturing the fossa ovalis at the puncture site.

In some applications, the method further includes, while the balloon is in contact with the septum, and before the puncturing of the fossa ovalis, using a stabilization of the catheter provided by the balloon being in contact with the septum to steer the distal portion of the catheter toward the puncture site, and puncturing the fossa ovalis includes sliding the puncturing element from the distal portion of the catheter.

In some applications, the method further includes, while the balloon is in contact with the septum, and before the puncturing of the fossa ovalis, using a stabilization of the catheter provided by the balloon being in contact with the septum to adjust an orientation of the distal portion of the catheter, and puncturing the fossa ovalis includes sliding the puncturing element:

from the distal portion of the catheter, and through the fossa ovalis, at an angle with respect to the fossa ovalis that is determined by the orientation of the distal portion of the catheter.

In some applications, the balloon includes an at least partially radiopaque surface thereof, and the method further includes using fluoroscopic imaging to view the at least partially radiopaque surface during and following the deployment of the balloon.

In some applications, deploying the balloon includes deploying a compliant balloon.

In some applications, deploying the balloon includes deploying the balloon at an internal pressure of 10-70 mmHg.

In some applications, deploying the balloon includes deploying the balloon at an internal pressure of 30-50 mmHg.

In some applications, deploying the balloon includes deploying a balloon that contains a contrast agent, and the method further includes using imaging to view the contrast agent during and following the deployment of the balloon.

In some applications, deploying the balloon includes deploying an annular balloon, shaped to define a hole, the distal portion of the catheter passing through the hole.

In some applications, deploying the annular balloon includes deploying a torus-shaped balloon.

In some applications, deploying the balloon includes deploying the balloon such that a volume thereof is between 0.5 and 4 mL.

In some applications, deploying the balloon includes deploying the balloon such that a volume thereof is between 2 and 8 mL.

In some applications, deploying the balloon includes deploying the balloon such that a surface area thereof that is not in contact with the catheter is between 300 and 1250 mm2.

In some applications, deploying the balloon includes deploying the balloon such that a surface area thereof that is not in contact with the catheter is between 1500 and 3000 mm2.

In some applications, deploying the balloon includes deploying a non-compliant balloon.

In some applications, deploying the balloon includes expanding the balloon by:

distally sliding at least one slider disposed along an outer surface of the catheter, the slider being coupled to a plurality of ribs coupled to a surface of the balloon, and filling the balloon with a fluid.

In some applications, expanding the balloon includes expanding a balloon that covers a distal tip of the catheter.

In some applications, expanding the balloon that covers the distal tip of the catheter includes expanding a balloon an inner surface of which is attached to the distal tip of the catheter.

In some applications, the method further includes using the puncturing element to puncture the balloon immediately prior to puncturing the fossa ovalis.

In some applications, deploying the balloon includes deploying the balloon at an internal pressure of 10-70 mmHg.

In some applications, deploying the balloon includes deploying the balloon at an internal pressure of 30-50 mmHg.

In some applications, deploying the balloon includes deploying a balloon that contains a contrast agent, and the method further includes using imaging to view the contrast agent during and following the deployment of the balloon.

In some applications, deploying the balloon includes deploying the balloon such that a volume thereof is between 0.5 and 4 mL.

In some applications, deploying the balloon includes deploying the balloon such that a volume thereof is between 2 and 4 mL.

In some applications, deploying the balloon includes deploying the balloon such that a surface area thereof that is not in contact with the catheter is between 300 and 1250 mm2.

In some applications, deploying the balloon includes deploying the balloon such that a surface area thereof that is not in contact with the catheter is between 1500 and 2250 mm2.

There is further provided, in accordance with some applications of the present invention, a method for puncturing a fossa ovalis of a heart, the method including:

inserting a catheter into a right atrium of the heart;

advancing a distal portion of the catheter toward an interatrial septum of the heart;

deploying a probing element from the distal portion of the catheter;

probing (a) tissue near the fossa ovalis, the probing element having a first configuration thereof upon probing the tissue near the fossa ovalis, and (b) tissue of the fossa ovalis;

identifying a puncture site for puncturing the fossa ovalis, in response to the probing element automatically adopting a second configuration thereof that is different from the first configuration, upon probing the tissue of the fossa ovalis; and using a puncturing element, puncturing the fossa ovalis at the puncture site.

In some applications, the method further includes, following the identifying of the puncture site and before the puncturing of the fossa ovalis, by pushing against the fossa ovalis with the probing element, steering the distal portion of the catheter toward the puncture site, and puncturing the fossa ovalis includes sliding the puncturing element from the distal portion of the catheter.

In some applications, the method further includes, following the identifying of the puncture site and before the puncturing of the fossa ovalis, adjusting an orientation of the distal portion of the catheter, by using the probing element as a pivot, and puncturing the fossa ovalis includes sliding the puncturing element:
from the distal portion of the catheter, and
through the fossa ovalis, at an angle with respect to the fossa ovalis that is determined by the orientation of the distal portion of the catheter.

In some applications, deploying the probing element includes deploying a flexible sheet.

In some applications, the flexible sheet includes a radiopaque pattern, and the method further includes using fluoroscopic imaging to view the radiopaque pattern during and following the deployment of the probing element.

In some applications, deploying the probing element includes deploying a mesh.

In some applications, deploying the mesh includes deploying a mesh that includes (a) a first group of longitudinal elements, respective diameters of each of which being between 0.05 and 0.125 mm, and (b) a second group of longitudinal elements, respective diameters of each of which being between 0.1 and 0.5 mm.

In some applications, the method further includes stabilizing the catheter by pressing the second group of longitudinal elements against a perimeter of the fossa ovalis, prior to puncturing the fossa ovalis.

In some applications, the probing element includes a plurality of flexible longitudinal members, and probing the tissue near the fossa ovalis and tissue of the fossa ovalis includes contacting the tissue with distal tips of the flexible longitudinal members.

In some applications, identifying the puncture site includes identifying the puncture site in response to at least one of the flexible longitudinal members opposing movement of the probing element from the fossa ovalis, by pressing against a perimeter of the fossa ovalis.

In some applications, the probing element includes a spring, and identifying the puncture site includes identifying the puncture site in response to the spring elongating upon probing the tissue of the fossa ovalis.

In some applications, the method further includes:
following the identification of the puncture site, and before the puncturing of the fossa ovalis:
deploying one or more flexible longitudinal members from the distal portion of the catheter such that a deployed portion of each of the one or more flexible longitudinal members is shaped as a loop; and
contacting the fossa ovalis with at least one of the flexible longitudinal members.

In some applications, the method further includes, while the at least one of the flexible longitudinal members is contacting the fossa ovalis, and before the puncturing of the fossa ovalis:
by pushing against the fossa ovalis with the at least one of the flexible longitudinal members, steering the distal portion of the catheter toward the puncture site,
and puncturing the fossa ovalis includes sliding the puncturing element (a) from the distal portion of the catheter, and (b) through the fossa ovalis, at the puncture site.

In some applications, steering the distal portion of the catheter includes adjusting a length of the deployed portion of the at least one of the flexible longitudinal members.

In some applications, the method further includes, while the at least one of the flexible longitudinal members is contacting the fossa ovalis, and before the puncturing of the fossa ovalis, adjusting an orientation of the distal portion of the catheter, by using the at least one of the flexible longitudinal members as a pivot, and puncturing the fossa ovalis includes sliding the puncturing element:
from the distal portion of the catheter, and
through the fossa ovalis, at an angle with respect to the fossa ovalis that is determined by the orientation of the distal portion of the catheter.

In some applications, using the at least one of the flexible longitudinal members as a pivot includes adjusting a length of the deployed portion of the at least one of the flexible longitudinal members.

In some applications, deploying the one or more flexible longitudinal members from the distal portion of the catheter includes slidably passing each of the one or more flexible longitudinal members through one or more openings at the distal portion of the catheter.

In some applications, deploying the one or more flexible longitudinal members includes deploying each of the flexible longitudinal members such that a deployment angle of the flexible longitudinal member is between 10 and 80 degrees,
the deployment angle being an angle between (a) a vector that is (i) tangent to the flexible longitudinal member at an exit point of the flexible longitudinal member from the catheter, and (ii) directed away from the catheter, and (b) a distally-directed vector that is parallel to a longitudinal axis of the catheter at the exit point.

In some applications, deploying the one or more flexible longitudinal members includes deploying each of the flexible longitudinal members such that the deployment angle is between 30 and 60 degrees.

In some applications, deploying the probing element includes deploying a radiopaque probing element, and the method further includes using fluoroscopic imaging to view the probing element during and following deployment thereof.

In some applications, deploying the probing element includes deploying a probing element to which are coupled a plurality of radiopaque markers, and the method further includes using fluoroscopic imaging to view the radiopaque markers during and following the deployment of the probing element.

There is further provided, in accordance with some applications of the present invention, a method for puncturing a fossa ovalis of a heart, the method including:
inserting a catheter into a right atrium of the heart;
advancing a distal portion of the catheter toward an interatrial septum of the heart;
deploying a probing element from the distal portion of the catheter;
using the probing element, probing tissue by applying a pushing force to the tissue;
using a sensor, measuring the pushing force;
identifying a puncture site for puncturing the fossa ovalis, in response to the measuring of the pushing force; and
using a puncturing element, puncturing the fossa ovalis at the puncture site.

In some applications, using the sensor includes using a load-cell sensor.

In some applications, the sensor is further configured to measure a displacement of the probing element, and the identifying of the puncture site is further in response to the measuring of the displacement.

In some applications, the identifying of the puncture site includes identifying the puncture site in response to a ratio of the displacement to the pushing force being higher at a given region of tissue, relative to a second region of tissue.

In some applications, the probing element includes a spring, and using the sensor to measure the pushing force includes using the sensor to measure a compression of the spring.

There is further provided, in accordance with some applications of the present invention, a method for puncturing a fossa ovalis of a heart, the method including:

inserting apparatus into a right atrium of the heart, the apparatus including:
a shaft;
a first joint;
a second joint coupled to a distal portion of the shaft, the second joint being slidably disposed with respect to the first joint;
a first arm pivotably coupled, at a proximal portion thereof, to the first joint;
a second arm pivotably coupled:
at a proximal portion thereof, to the second joint, and
at a distal portion thereof, to a distal portion of the first arm,
an arm selected from the group consisting of: the first arm, and the second arm, being shaped to define a lumen thereof, and
a positioning-facilitating element;
by sliding the second joint toward the first joint, moving the coupled distal portions of the first and second arms toward the interatrial septum;
deploying the positioning-facilitating element from the lumen of the selected arm;
contacting the interatrial septum with the positioning-facilitating element;
identifying a puncture site, in response to the contacting; and
using a puncturing element, puncturing the fossa ovalis at the puncture site.

In some applications, the method further includes deploying the puncturing element from the lumen of the selected arm, prior to puncturing the fossa ovalis.

In some applications, the positioning-facilitating element is radiopaque, and the method further includes using fluoroscopic imaging to view the positioning-facilitating element during and after the deployment thereof.

In some applications, the apparatus further includes a plurality of radiopaque markers coupled to the positioning-facilitating element, and the method further includes using fluoroscopic imaging to view the radiopaque markers during and after the deployment of the positioning-facilitating element.

In some applications, the positioning-facilitating element includes a probing element, and:
deploying the positioning-facilitating element includes deploying the probing element,
contacting the interatrial septum with the positioning-facilitating element includes using the probing element to probe (a) tissue near the fossa ovalis, the probing element having a first configuration thereof, upon probing the tissue near the fossa ovalis, and (b) tissue of the fossa ovalis, and
identifying the puncture site includes identifying the puncture site in response to the probing element automatically adopting a second configuration thereof that is different from the first configuration, upon probing the tissue of the fossa ovalis.

In some applications, the probing element includes a plurality of flexible longitudinal members, and deploying the probing element includes deploying the plurality of flexible longitudinal members.

In some applications, the probing element includes a spring configured to elongate upon probing the tissue of the fossa ovalis, and deploying the probing element includes deploying the spring.

In some applications, the positioning-facilitating element includes a balloon, and deploying the positioning-facilitating element includes deploying the balloon.

In some applications, the balloon is a compliant balloon, and deploying the balloon includes deploying the compliant balloon.

In some applications, the second joint is coupled by a spring to the first joint, and sliding the second joint toward the first joint includes sliding the second joint toward the first joint by changing a length of the spring.

There is further provided, in accordance with some applications of the present invention, a method for identifying a puncture site for puncturing a fossa ovalis of a heart, the method including:

inserting a catheter into a right atrium of the heart;
advancing a distal portion of the catheter toward an interatrial septum of the heart;
deploying a probing element from the distal portion of the catheter, the probing element including:
a body, and
a blunt head pivotably coupled to the body, a radius of curvature of a distal portion of the blunt head being between 1 and 3 mm;
using the probing element, probing (a) tissue near the fossa ovalis, and (b) tissue of the fossa ovalis; and
identifying the puncture site, in response to the probing.

In some applications, the blunt head includes a radiopaque blunt head, and the method further includes using fluoroscopic imaging to view the radiopaque blunt head while the blunt head probes tissue near the fossa ovalis and tissue of the fossa ovalis.

In some applications, one or more radiopaque markers are coupled to the blunt head, and the method further includes using fluoroscopic imaging to view the radiopaque markers while the blunt head probes tissue near the fossa ovalis and tissue of the fossa ovalis.

There is further provided, in accordance with some applications of the present invention, a method for identifying a puncture site for puncturing a fossa ovalis of a heart, the method including:

inserting a catheter into a right atrium of the heart;
advancing a distal portion of the catheter toward an interatrial septum of the heart;
deploying a pushing element from the distal portion of the catheter, the pushing element including a blunt head, a radius of curvature of a distal portion of the blunt head being between 1 and 3 mm, a proximal portion of the pushing element being coupled to a spring;
probing tissue at a plurality of sites, the probing including:
pushing with the pushing element, by compressing the spring to a compressed position; and
retracting the pushing element, by releasing the spring from the compressed position; and
in response to the probing, identifying the puncture site.

There is further provided, in accordance with some applications of the present invention, a method for puncturing a fossa ovalis of a heart, the method including:

deploying a positioning-facilitating element from a catheter;
contacting an interatrial septum of the heart with the positioning-facilitating element;

while the positioning-facilitating element is contacting the interatrial septum, using imaging to view the positioning-facilitating element;

in response to viewing the positioning-facilitating element, ascertaining that the positioning-facilitating element is contacting the fossa ovalis;

in response to the ascertaining, using the positioning-facilitating element to perform a function selected from the group consisting of: stabilizing the catheter, steering the catheter, and adjusting an orientation of the catheter with respect to the fossa ovalis; and following the performing of the selected function, using a puncturing element to puncture the fossa ovalis.

In general, apparatus and methods described herein can also be used to penetrate other body orifices. (In this context, penetration of the body orifice might not include puncturing with a puncturing element, as is typically the case for the fossa ovalis.) For example, apparatus and methods described herein can be used to pass a catheter and/or a therapeutic device through the coronary sinus ostium and into the coronary sinus. Furthermore, apparatus and methods described herein can also be used to locate an opening, natural or manmade, in a portion of anatomy. For example, apparatus and methods described herein can be used to locate the coronary sinus ostium, a natural opening in the fossa ovalis, or a puncture in the fossa ovalis. In some applications, apparatus described herein may be further configured to deliver a plug (e.g., an Amplatzer™), or other such stopping device, to the opening.

The present invention will be more fully understood from the following detailed description of applications thereof, taken together with the drawings, in which:

BRIEF DESCRIPTION OF THE DRAWINGS

FIG. 1B is a schematic illustration of (a) cross sections of penetration apparatus, (b) advancement of a penetration apparatus, and (c) deployment of a flexible longitudinal member, in accordance with some applications of the present invention;

FIG. 1C is a schematic illustration of penetration of a fossa ovalis, in accordance with some applications of the present invention;

FIG. 1E is a schematic illustration of a catheter following penetration of a fossa ovalis, in accordance with some applications of the present invention;

FIG. 2 is a schematic illustration of four distinct regions of interest contained within a fossa ovalis, for use with some applications of the present invention;

FIGS. 3A-E, 4A-C, 5A-D, 6A-C, 7A-D, 8A-E, and 9-11 are schematic illustrations of apparatus for puncturing a fossa ovalis of a heart, in accordance with some applications of the present invention;

FIGS. 12A-H, 13, and 14A-B are schematic illustrations of apparatus for identifying a puncture site for puncturing a fossa ovalis of a heart, in accordance with some applications of the present invention.

DETAILED DESCRIPTION OF APPLICATIONS

Figure 1A:
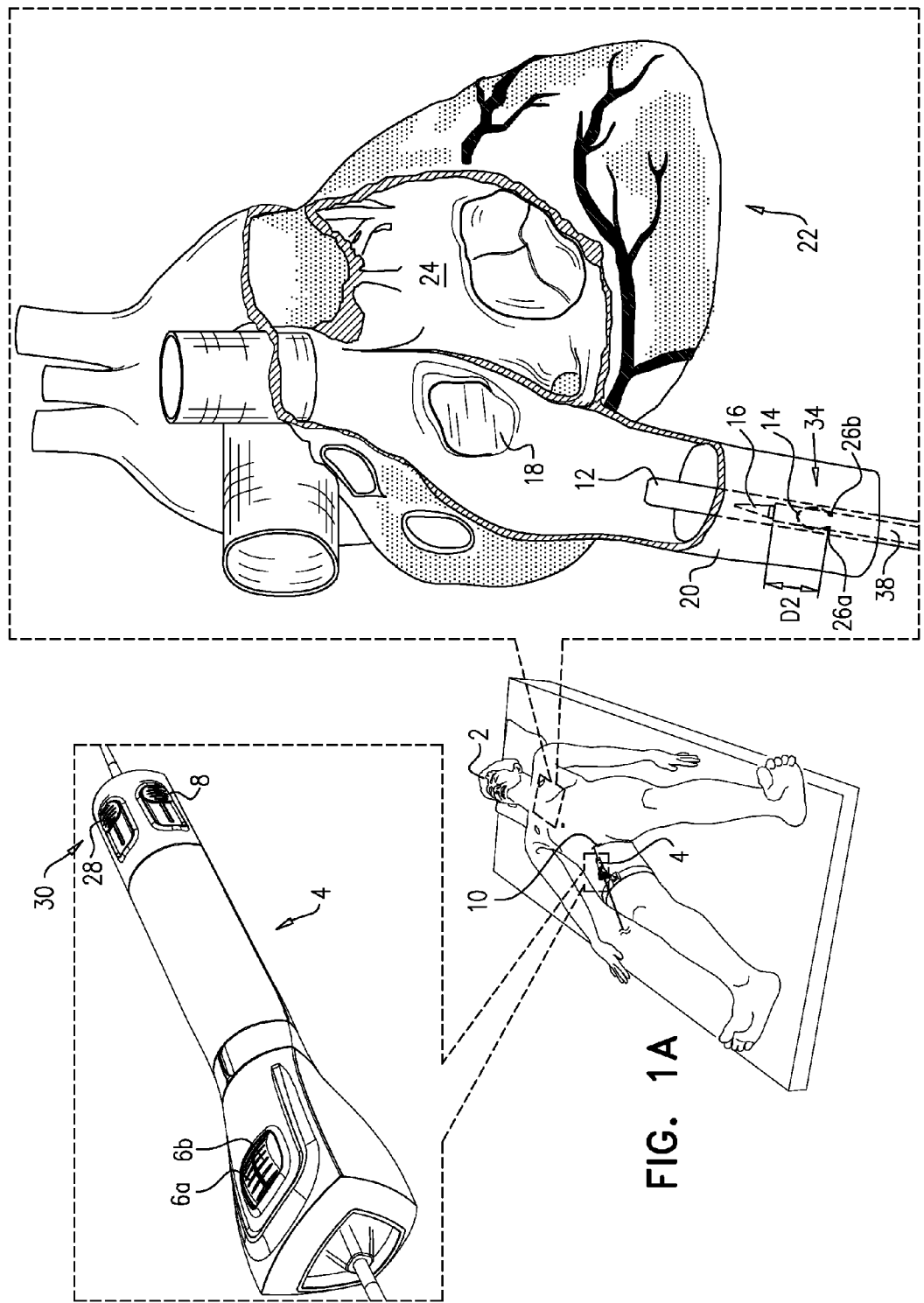
FIG. 1A is a schematic illustration of an operating handle and a distal portion of penetration apparatus, in accordance with some applications of the present invention.

Reference is now made to FIG. 1A, which is a schematic illustration of the operating handle 4 and distal portion of penetration apparatus 34, in accordance with some applications of the present invention. In some applications of the present invention, penetration apparatus 34 is inserted into a vein in the pelvic area of a patient 2 through opening 10 and is advanced toward heart 22 of the patient through inferior vena cava 20. Penetration apparatus 34 comprises a catheter 38, which has protruding from its distal tip a dilator tip 16. Penetration apparatus 34 also comprises a flexible longitudinal member 14, which passes through openings 26a and 26b disposed at a distal portion of catheter 38, typically into respective lumens 27a and 27b (FIG. 1B) in the wall of catheter 38. In accordance with some applications of the present invention, catheter 38 is contained within the lumen of a sheath 12 during parts of the insertion and/or withdrawal of penetration apparatus 34. Sheath 12 may, for example, prevent damage to surrounding tissue as penetration apparatus 34 is advanced and/or withdrawn.

Typically, openings 26a and 26b are separated by a distance D1 (FIG. 1B) that is greater than 1 mm and/or less than 12 mm (e.g., 1-5 mm, or 5-12 mm). Alternatively or additionally, openings 26a and 26b are separated by an arc theta (FIG. 1B) that is greater than 10 degrees and/or less than 350 degrees (e.g., 20-90 degrees, or 90-180 degrees), with respect to a longitudinal axis of catheter 38. For some applications, the openings are disposed at a distance D2 that is 1-5 cm from the distal tip of the catheter. Alternatively, the openings are disposed 0-1 cm from the distal tip (even, for example, protruding from the distal tip of the catheter). Typically, the distance of one opening from the distal tip differs by less than 1 cm from the distance of the other opening from the distal tip. For example, both openings may be the same distance D2 from the distal tip of the catheter.

The left exploded view of FIG. 1A shows an operating handle 4, in accordance with some applications of the present invention. Operating handle 4 comprises one or more adjustment mechanisms 6a and 6b (e.g., dials) for advancing and retracting the respective ends of longitudinal member 14.

Reference is now made to FIG. 1B, which is a schematic illustration of (a) cross sections of penetration apparatus 34, (b) advancement of penetration apparatus 34, and (c) deployment of flexible longitudinal member 14, in accordance with some applications of the present invention. The illustration of the heart on the left of FIG. 1B shows penetration apparatus 34 advanced through the distal end of sheath 12 toward fossa ovalis 18. The top-left exploded view shows a closer view of the advancement of penetration apparatus 34. Section A-A shows a cross-section of catheter 38 at the longitudinal position of openings 26a and 26b. Contained within the lumen of catheter 38 is dilator body 50, which, in turn, contains within its lumen a puncturing element 32. Section B-B shows a cross-section of catheter 38 at a position proximal to openings 26a and 26b. The wall of catheter 38 is shown being shaped to define lumens 27a and 27b for passage of flexible longitudinal member 14. The top-right exploded view shows penetration apparatus 34 further advanced toward fossa ovalis 18. Catheter 38 is typically a steerable catheter, allowing steering of the catheter toward the desired puncturing point of the fossa ovalis. In the bottom-left exploded view, flexible longitudinal member 14 is shown being passed through openings 26a and 26b and advanced toward fossa ovalis 18. In the bottom-right exploded view, flexible longitudinal member 14 is made to loop around the inside perimeter of fossa ovalis 18, thus typically fluoroscopically demarcating the perimeter of fossa ovalis 18, aligning and stabilizing catheter 38 with respect to fossa ovalis 18, and/or stretching the tissue of fossa ovalis 18 to facilitate penetration.

Reference is now made to FIG. 1C, which is a schematic illustration of a penetration of fossa ovalis 18, in accordance with some applications of the present invention. In the left illustration of FIG. 1C, penetration apparatus 34 is shown advanced toward fossa ovalis 18 following placement of flexible longitudinal member 14. The top-left and top-right exploded views depict catheter 38 as flexibly and rotatably steerable, in accordance with some applications of the present invention. Steerability of catheter 38 allows for better localization of a desired puncturing point. In the bottom-left exploded view, the distal end of dilator tip 16 is brought into contact with fossa ovalis 18 and puncturing element 32 is advanced through the opening at the distal end of dilator tip 16 and through fossa ovalis 18, thus puncturing a hole 40 in fossa ovalis 18. The bottom-right exploded view shows dilator body 50 advanced through punctured hole 40 and into left atrium 24.

Reference is again made to FIG. 1A. In accordance with some applications of the present invention, operating handle 4 comprises control element 30, which in turn may comprise a slider 28 and a slider 8 which control advancement and retraction of, respectively, puncturing element 32 and the dilator element. For some applications, control element 30 is detached from operating handle 4 following penetration of fossa ovalis 18, after which a different control element for a therapeutic device (not shown) may be attached. Operating handle 4 may be fastened to a leg of patient 2 or to some other stable surface, e.g., part of an operating table, so as to facilitate steady penetration of fossa ovalis 18 and execution of subsequent therapeutic procedures.

Figure 1D:
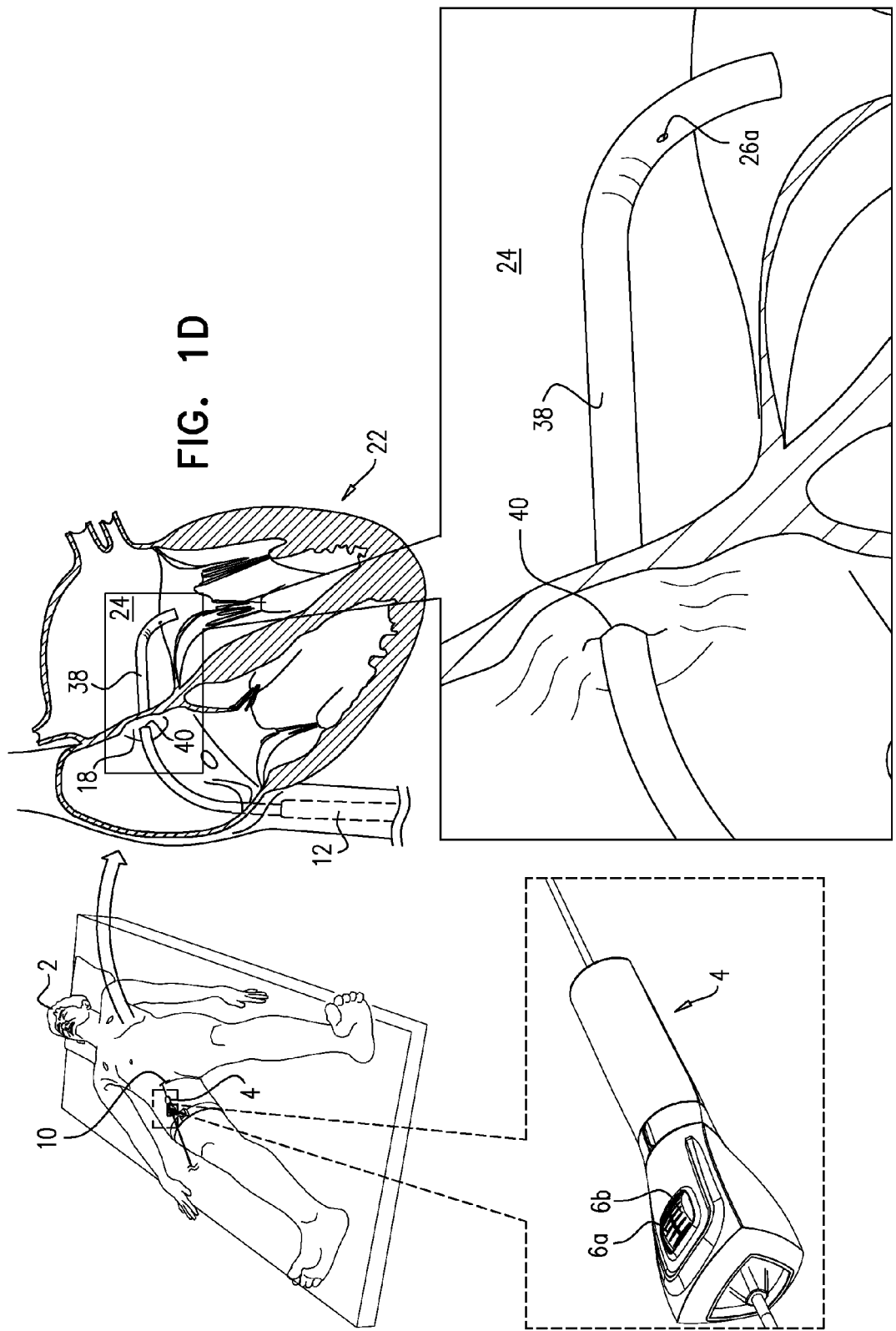
FIG. 1D is a schematic illustration of an operating handle and catheter following penetration of a fossa ovalis, in accordance with some applications of the present invention.

Reference is now made to FIG. 1D, which is a schematic illustration of operating handle 4 and catheter 38 following the penetration of fossa ovalis 18 and withdrawal of (a) the dilator element, (b) puncturing element 32, and (c) flexible longitudinal member 14, in accordance with some applications of the present invention. In the bottom-left exploded view, operating handle 4 is shown following removal of control element 30. The exploded view of heart 22 shows the position of catheter 38 following withdrawal of the dilator element, puncturing element 32, and flexible longitudinal member 14. In accordance with some applications of the present invention, the distal portion of catheter 38 remains in left atrium 24 following penetration to allow for subsequent advancement of therapeutic devices through the catheter.

Reference is now made to FIG. 1E, which is a schematic illustration of catheter 38 following the penetration of fossa ovalis 18, in accordance with another application of the present invention. This figure differs from FIG. 1D in that flexible longitudinal member 14 is shown retracted back into its preoperative position following penetration of fossa ovalis 18.

Reference is now made to FIG. 2, which is a schematic illustration of four distinct regions of interest 42, 44, 46, and 48 contained within fossa ovalis 18, for use with some applications of the present invention. As declared by some medical practitioners, each region of interest is a preferred puncture site for a different procedure. For example, region of interest 42 (superior and posterior) is a preferred puncture site for using the MitraClip™ to treat degenerative mitral regurgitation and performing mitral valve replacement. Region of interest 44 (superior and anterior) is a preferred puncture site for using the MitraClip™ for treating functional mitral regurgitation. Region of interest 46 (inferior and anterior) is a preferred puncture site for accessing the left atrium to perform pulmonary vein isolation. Region of interest 48 (inferior and posterior) is a preferred puncture site for facilitating left atrial appendage closure. Placement of flexible longitudinal member 14 around the inside perimeter of fossa ovalis 18 facilitates localization of the preferred puncture site by positioning and stabilizing catheter 38 over the preferred puncture site prior to puncturing fossa ovalis 18. In accordance with some applications of the present invention, flexible longitudinal member 14 and/or a ring at a distal portion of catheter 38 are radiopaque, thus allowing for use of fluoroscopic imaging techniques to further facilitate localization of the puncture site.

It is noted that flexible longitudinal member 14 is shown in the figures as slightly protruding away from the body of catheter 38 during advancement of the catheter toward fossa ovalis 18 (FIG. 1B) and through fossa ovalis 18 (FIG. 1E). Nevertheless, the scope of the present invention includes providing an indented region (not shown) in the outer wall of catheter 38, and disposing flexible longitudinal member 14 in the indented region during advancement of the catheter toward and/or through the fossa ovalis.

Reference is now made to FIGS. 3A-E and FIGS. 4A-C, which are schematic illustrations of apparatus 34 for puncturing a fossa ovalis of a heart, in accordance with some applications of the present invention. Apparatus 34 comprises catheter 38, shaped to define a catheter lumen 52. Apparatus 34 further comprises puncturing element 32, which is slidably disposed within catheter lumen 52, and is configured to be deployed from a distal portion 54 of catheter 38 and to puncture fossa ovalis 18. Apparatus 34 further comprises one or more flexible longitudinal members 14 slidably disposed within catheter lumen 52. Flexible longitudinal members 14 are generally disposed in and deployed from catheter 38 as described above, with reference to FIGS. 1 and 2. For example, FIGS. 3 and 4 show catheter 38 shaped to define one or more openings 26 at distal portion 54 of the catheter, flexible longitudinal members 14 being configured to be deployed from distal portion 54 by being slidably passed through openings 26.

As shown in FIGS. 1B-C, FIGS. 3B-C, and FIGS. 4B-C, flexible longitudinal members 14 are typically configured to be deployed such that respective deployed portions 58 of the flexible longitudinal members are shaped as loops. In some applications, flexible longitudinal members 14 are configured to contact the tissue at the perimeter of the fossa ovalis such that puncturing element 32 passes through at least one of the loops, before puncturing the fossa ovalis. In some applications, as shown in FIG. 1C, the one or more flexible longitudinal members 14 consist of a single flexible longitudinal member, and puncturing element 32 passes through the single looped-shaped deployed portion of the single flexible longitudinal member before puncturing the fossa ovalis.

Figure 3C:
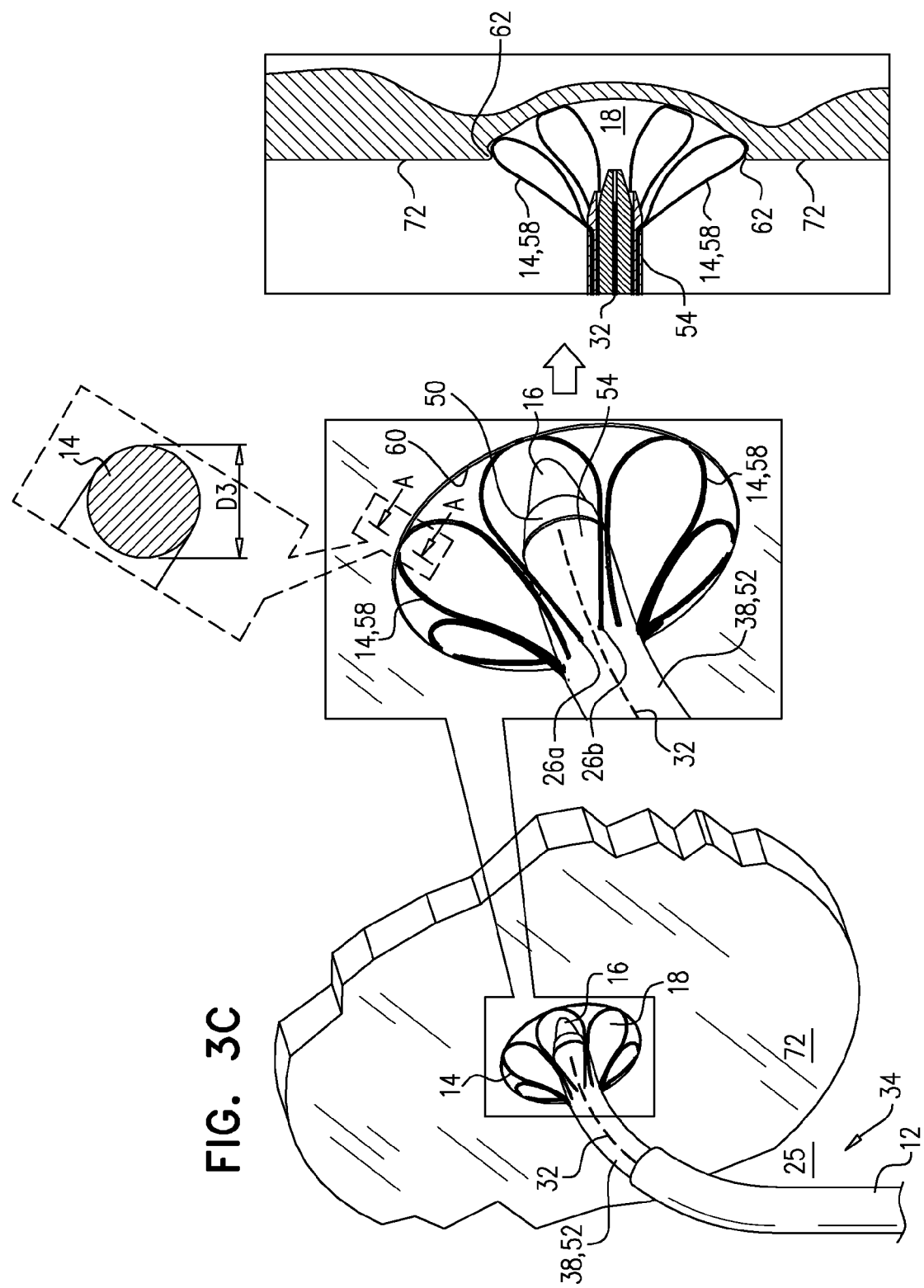

In some applications, flexible longitudinal members 14 are mechanically resilient, i.e., they do not readily buckle upon being subjected to force, as would, for example, a string. As shown in FIG. 3C, respective diameters D3 of flexible longitudinal members 14 are typically between 0.1 and 0.5 mm. Typically, flexible longitudinal members 14 comprise one or more wires, and are typically made of nitinol, stainless steel, and/or chromium cobalt. The scope of the present invention allows for any number of flexible longitudinal members 14, e.g., one, two (as in FIG. 4), three, four to six (as in FIG. 3), or more than six.

Upon being deployed, flexible longitudinal members 14 facilitate the puncturing of fossa ovalis 18 by puncturing element 32. The manner in which this facilitation occurs is similar to, although different from, the manner described above with reference to FIG. 1B. In FIG. 1B, flexible longitudinal member 14 is shown looping around an inside perimeter of fossa ovalis 18, such that, for example, a single member 14 loops around a large portion, e.g., most of or substantially all, of the perimeter. In FIGS. 3C and 4C, on the other hand, one or more flexible longitudinal members 14 contact tissue at perimeter 60 of fossa ovalis 18, typically by contacting a smaller portion of perimeter 60, relative to the application shown in FIG. 1B. The contacting of perimeter 60 typically facilitates the puncturing in at least two ways. First, the contacting typically helps position catheter 38 over the fossa ovalis. For example, by contacting rim 62 of the fossa ovalis (FIGS. 3B-C and 4B), which is typically present at perimeter 60, the flexible longitudinal members keep the catheter from moving away from the fossa ovalis. Second, the contacting typically helps stabilize the catheter over the puncture site.

In some applications, as shown in FIGS. 3B and 4B, each of flexible longitudinal members 14 is configured to be deployed from catheter 38 such that, in an absence of any force applied to the deployed portion of the flexible longitudinal member by an element that is not part of the apparatus, a deployment angle theta of the flexible longitudinal member is between 10 and 100 degrees. The deployment angle is defined as the angle between (a) a vector 64 that is tangent to the flexible longitudinal member at an exit point 68 of the flexible longitudinal member, and is directed away from the catheter, and (b) a distally-directed vector 66 that is parallel to the longitudinal axis 70 of the catheter at exit point 68. As shown in FIGS. 3B and 4B, exit point 68 is the point at which the flexible longitudinal member is deployed from the catheter, e.g., it may be identical to opening 26.

FIG. 3B shows a deployment angle theta that is between 10 and 80 degrees, e.g., 30-60 degrees. For deployment angles within this range, each of the flexible longitudinal members is typically deployed such as to have a flower-petal shape, the distal end of the petal being configured to contact tissue of the fossa ovalis. (A plurality of flexible longitudinal members deployed in this manner thus may take on a flower-shaped configuration, such as the configuration shown in FIG. 3.) FIG. 4B, on the other hand, shows a deployment angle of 85-95 degrees. For deployment angles within this range, there are typically two loop-shaped flexible longitudinal members, each of the flexible longitudinal members being deployed from two opposing lateral openings 26a and 26b.

In general, the scope of the present invention allows for combining various features of FIG. 3 with those of FIG. 4. For example, apparatus 34 may comprise one or more flexible longitudinal members 14 as shown in FIG. 3, along with one or more flexible longitudinal members 14 as shown in FIG. 4.

In some applications, flexible longitudinal members 14 are radiopaque. The radiopacity of the flexible longitudinal members facilitates fluoroscopic imaging of the flexible longitudinal members, thus helping the physician find the desired puncture site on the fossa ovalis. In some applications, apparatus 34 comprises a plurality of radiopaque markers (not shown) coupled to the flexible longitudinal members, the radiopaque markers facilitating fluoroscopic imaging, as described above. In some applications, ultrasound imaging of flexible longitudinal members 14 is used instead of or in addition to fluoroscopic imaging, during and/or following deployment of the flexible longitudinal members.

With respect to the above-described imaging of flexible longitudinal members 14, in addition to all other references to imaging in the present description, it is noted that the scope of the present invention allows for one or more displays to be used to display the imaged element(s). The one or more displays may include a standalone display unit, e.g., a monitor, and/or may include a display element of operating handle 4. It is further noted that the use of fluoroscopic imaging, as described in various contexts throughout the present application, is generally advantageous, in that an imaging device need not be placed inside patient 2 in order to perform the imaging. (In some applications, however, intracardiac echocardiography, for example, in which an imaging device is inserted into the heart, may be used in addition to or instead of fluoroscopic imaging.)

As described above with reference to FIG. 1, apparatus 34 typically comprises a dilator element 49, which comprises (a) dilator body 50, shaped to define a dilator lumen 51, and (b) dilator tip 16, disposed at a distal end of the dilator element. Dilator element 49 is slidably disposed within catheter lumen 52. As described above, dilator tip 16 is configured to dilate an opening created by the puncture of the fossa ovalis. Typically, puncturing element 32 is slidably disposed within dilator lumen 51.

FIGS. 3 and 4 also show a method for puncturing fossa ovalis 18. The method begins (FIGS. 3A and 4A) with catheter 38 being inserted into right atrium 25 of the heart, and with distal portion 54 of the catheter being advanced toward the interatrial septum 72 of the heart. Subsequently (FIGS. 3B and 4B), a first set of one or more (e.g., one (as in FIG. 4B), two, three (as in FIG. 3B), or more than three) flexible longitudinal members 14 is deployed from distal portion 54 of the catheter. As shown in FIGS. 3B and 4B, deployed portion 58 of each of the flexible longitudinal members of the first set is shaped as a loop. At least one of the flexible longitudinal members of the first set is moved along a surface of interatrial septum 72, until the flexible longitudinal member contacts the fossa ovalis (FIGS. 3B and 4B). It is noted that the scope of the present invention includes moving the flexible longitudinal member(s) along the surface of septum 72 in either an upward direction, i.e., toward the fossa ovalis from below the fossa ovalis, or a downward direction, as shown in FIGS. 3B and 4B.

Figure 3D:
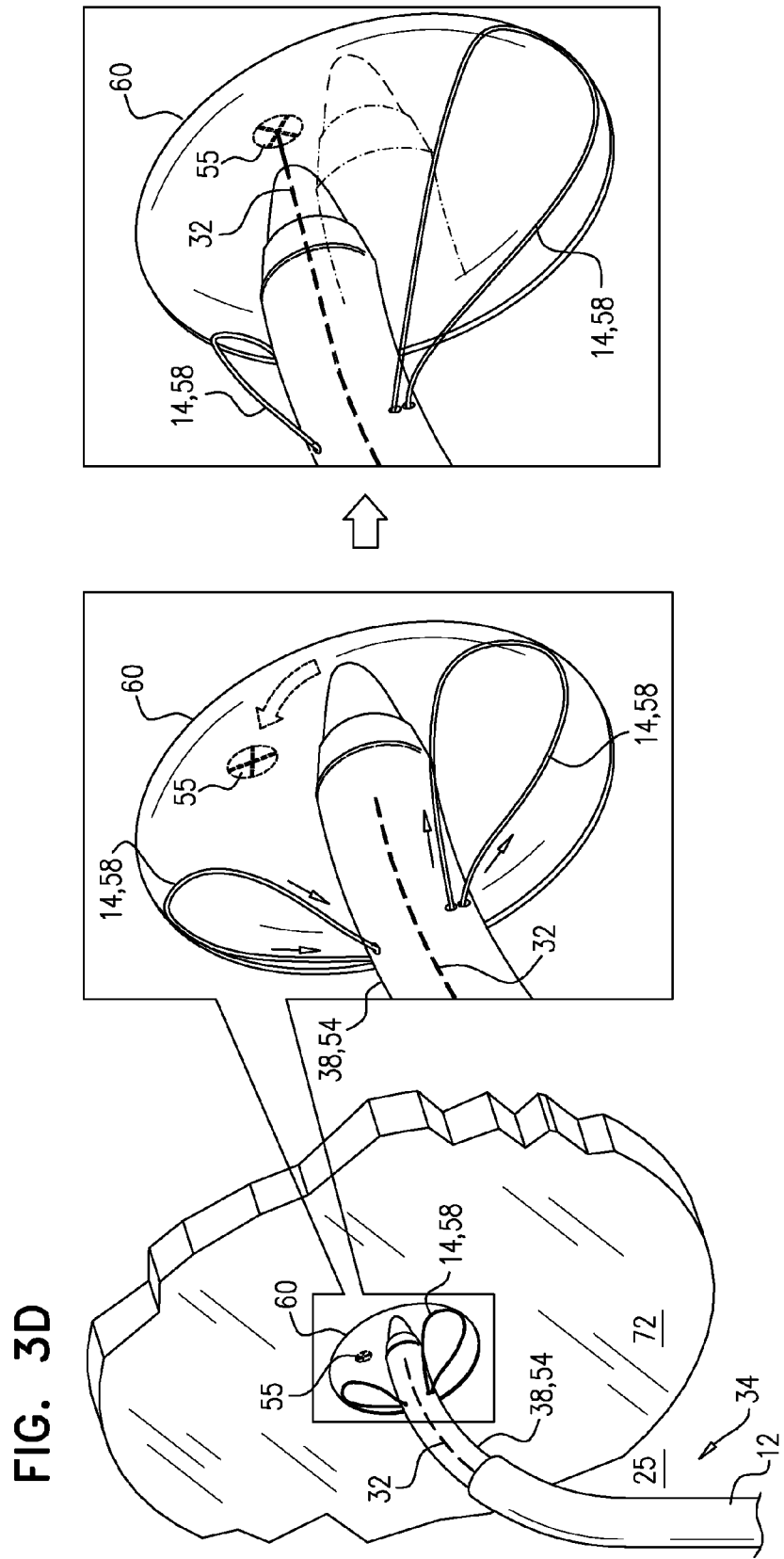
Figure 3E:
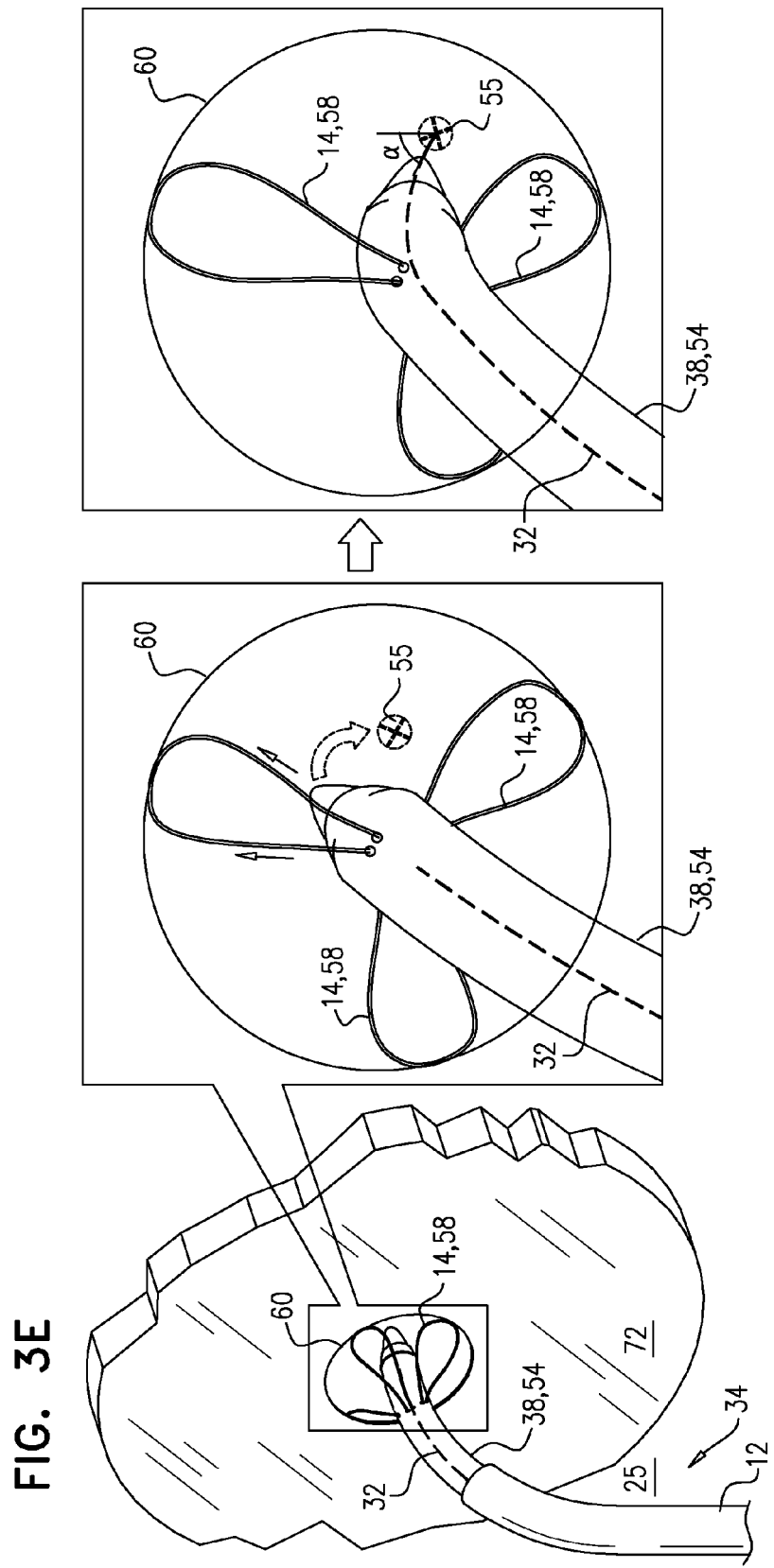

While the at least one flexible longitudinal member is contacting the fossa ovalis, puncturing element 32 may be used to puncture the fossa ovalis, as shown in FIGS. 3D-E, described in more detail hereinbelow. In some applications, as shown in FIG. 3C, at least two or three flexible longitudinal members of the first set may contact the fossa ovalis prior to the puncturing. Typically, by pressing the flexible longitudinal member(s) against perimeter 60, the catheter is stabilized prior to the puncturing.

In some applications, as shown in FIGS. 3C and 4C, a second set of one or more (e.g., one, two, or three) flexible longitudinal members 14 is deployed from the distal portion of the catheter, prior to the puncturing. (The second set does not comprise any flexible longitudinal members of the first set.) The deployed portion of each of the flexible longitudinal members of the second set is also shaped as a loop. As shown in FIGS. 3C and 4C, at least one (e.g., at least two, or at least three) of the flexible longitudinal members of the second set contacts the fossa ovalis, and/or stabilizes the catheter by pressing against perimeter 60 of the fossa ovalis, prior to the puncturing. The flexible longitudinal members of both the first and second sets are typically deployed by being slidably passed through openings 26, and are typically deployed with deployment angles of 10-100 degrees (e.g., 10-80 degrees, 30-60 degrees, or 85-95 degrees), as described hereinabove. As further described hereinabove, fluoroscopic imaging may be used to view radiopaque flexible longitudinal members 14 and/or radiopaque markers attached to the flexible longitudinal members, during and/or after deployment of the first and/or second sets. (Ultrasound imaging may be used instead of or in addition to fluoroscopic imaging.)

In some applications, as shown in FIG. 3D, distal portion 54 of the catheter is steered toward a desired puncture site 55 before the puncturing of the fossa ovalis. The steering is effected by pushing against the fossa ovalis with at least one of the flexible longitudinal members of the first set that is in contact with the fossa ovalis, and/or at least one of the flexible longitudinal members of the second set that is in contact with the fossa ovalis. For example, as shown in FIG. 3D, to steer distal portion 54 to the left, a flexible longitudinal member 14 deployed to the right of the catheter can be made to push against perimeter 60 of the fossa ovalis. Puncturing element 32 is then slid from the distal portion of the catheter, and through the fossa ovalis, at puncture site 55. In some applications, steering distal portion 54 comprises adjusting a length of the deployed portion of at least one of the flexible longitudinal members of the first set and/or at least one of the flexible longitudinal members of the second set. For example, as shown in FIG. 3D, to facilitate steering to the left, deployed portion 58 of right flexible longitudinal member 14 can be made longer, as it pushes against perimeter 60. Alternatively or additionally, as shown in FIG. 3D, deployed portion 58 of left flexible longitudinal member 14 can be made shorter.

In some applications, as shown in FIG. 3E, it is desired to control the angle at which puncturing element 32 punctures the fossa ovalis, and hence, it is desired to control the orientation of distal portion 54 of the catheter. In such applications, at least one of the flexible longitudinal members (belonging to the first set and/or the second set) that are contacting the fossa ovalis can be used as a pivot. For example, to orient distal portion 54 in a more downward orientation, distal portion 54 can be made to pivot relative to an upward-deployed flexible longitudinal member 14 that is contacting the fossa ovalis. Puncturing element 32 is then slid from distal portion 54 of the catheter, and through the fossa ovalis, at an angle alpha with respect to the fossa ovalis that is determined by the orientation of the distal portion of the catheter. In some applications, as shown in FIG. 3E, using flexible longitudinal member 14 as a pivot comprises adjusting a length of (e.g., lengthening) deployed portion 58 of the flexible longitudinal member.

In general, adjusting the orientation of distal portion 54, as shown in FIG. 3E, may be practiced in combination with steering distal portion 54, as shown in FIG. 3D. Furthermore, although FIGS. 3D-E show flexible longitudinal members 14 of the type shown in FIGS. 3A-C, the techniques described hereinabove with reference to FIGS. 3D-E may be practiced in combination with other apparatus described herein, mutatis mutandis. For example, the techniques may also be practiced in combination with flexible longitudinal members 14 of the type shown in FIGS. 4A-C, and/or with apparatus described below with reference to FIGS. 5-7 or FIGS. 8-10.

Expressed in a different way, the method for puncturing the fossa ovalis shown in FIG. 3 may be described as follows. First, a positioning-facilitating element, such as one or more flexible longitudinal members 14, is deployed from catheter 38 and contacts interatrial septum 72 (FIGS. 3A-B). While the positioning-facilitating element is contacting the interatrial septum, imaging is used to view the positioning-facilitating element. (For example, for applications in which flexible longitudinal members 14 are radiopaque, fluoroscopic imaging may be used to view the flexible longitudinal members.) In response to viewing the positioning-facilitating element, a physician ascertains that the positioning-facilitating element is contacting the fossa ovalis (FIG. 3B). In response to the ascertaining, the positioning-facilitating element is used to stabilize catheter 38, steer catheter 38, and/or adjust an orientation of catheter 38 with respect to the fossa ovalis (FIGS. 3C-E). Following the stabilizing, steering, and/or orientation-adjustment, puncturing element 32 is used to puncture the fossa ovalis (FIGS. 3D-E).

Figure 9:
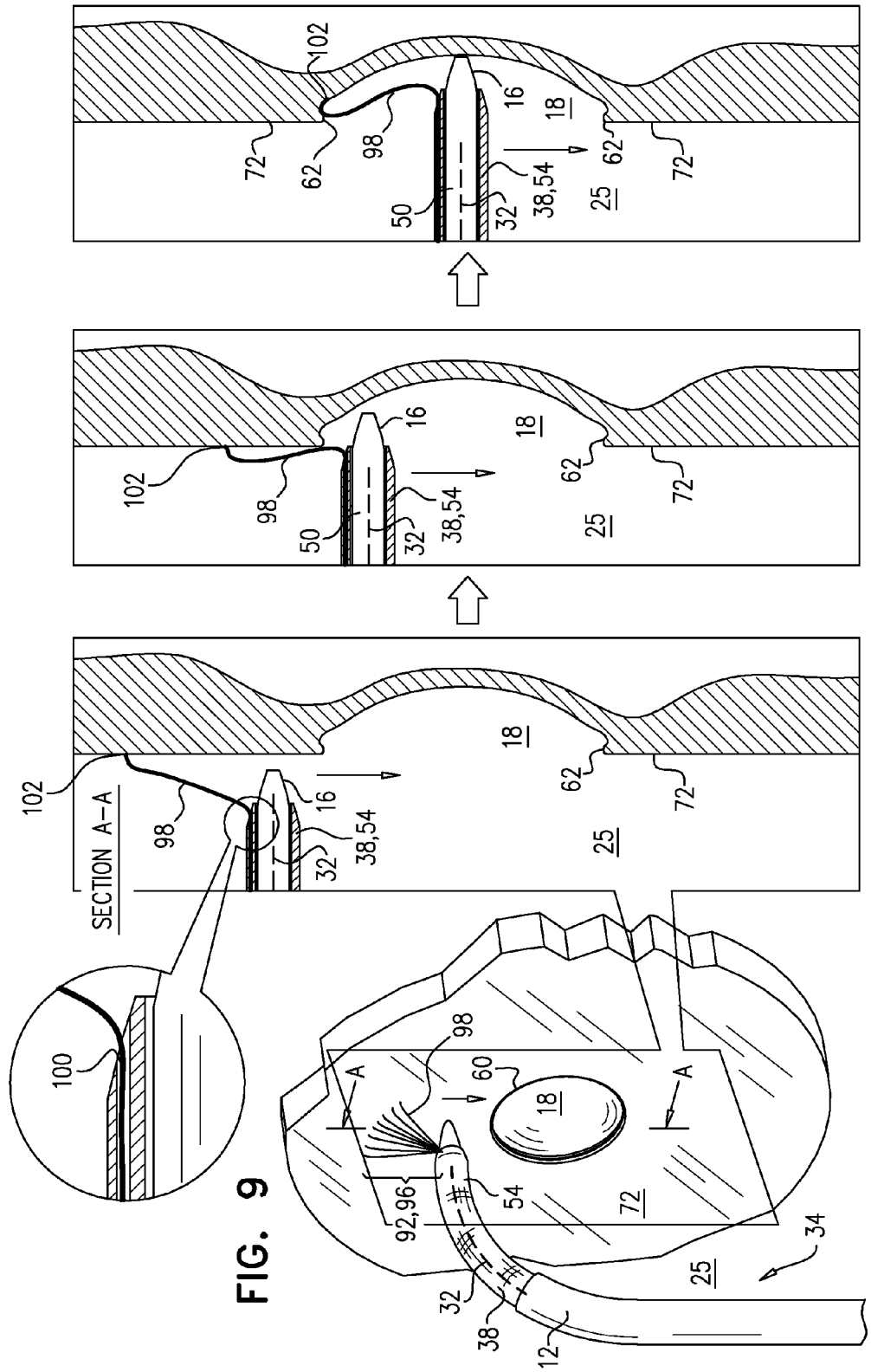
Figure 10:
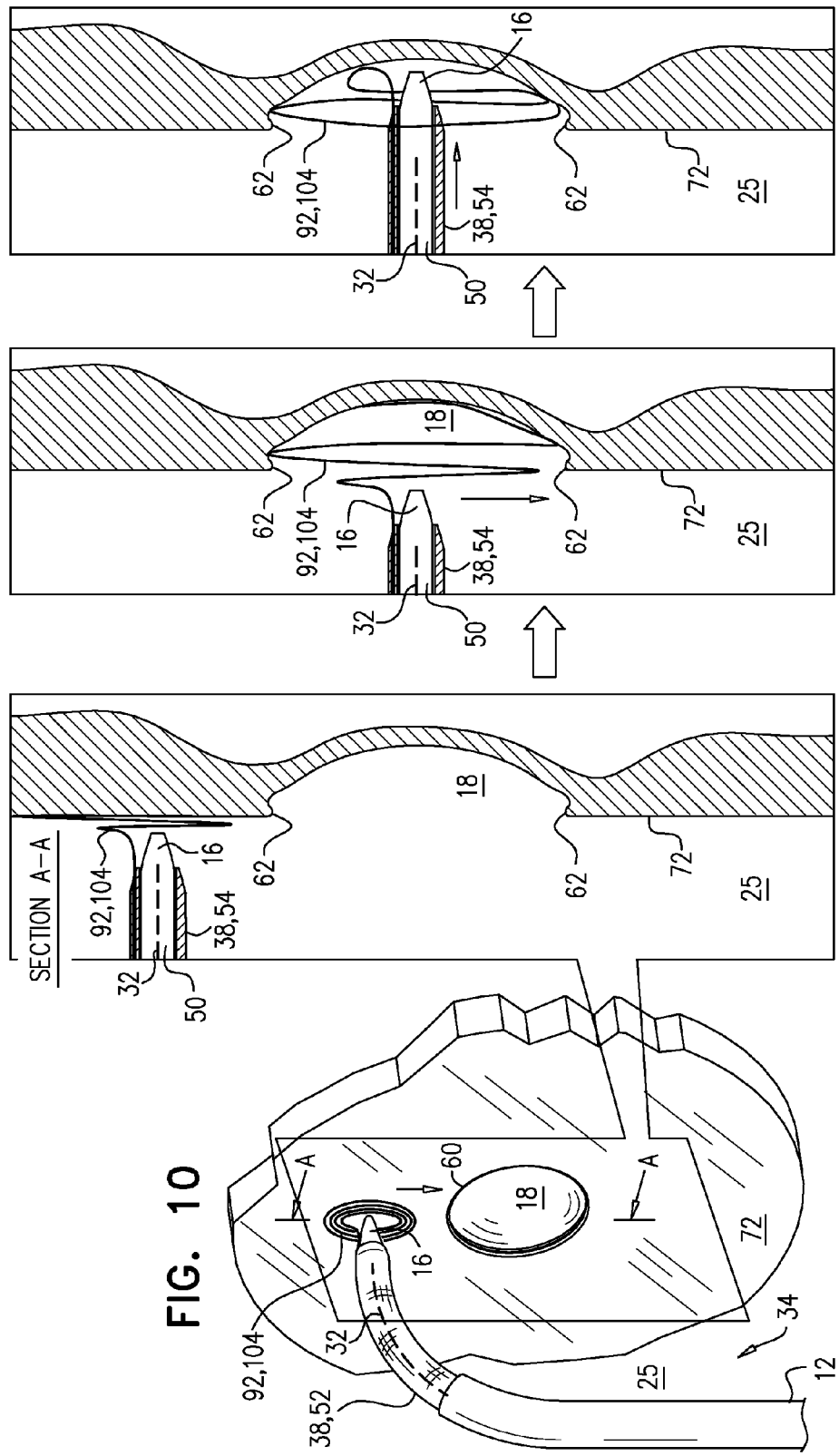

It is noted that the method described immediately above may be practiced with other types of positioning-facilitating elements described herein, in addition to the flexible longitudinal members of FIG. 3. For example, flexible longitudinal members 14 of the type shown in FIG. 4, the radially-expandable elements 74 of FIGS. 5-7, and the probing elements 92 of FIGS. 8-10 are all positioning-facilitating elements with which the method may be practiced.

Figure 7B:
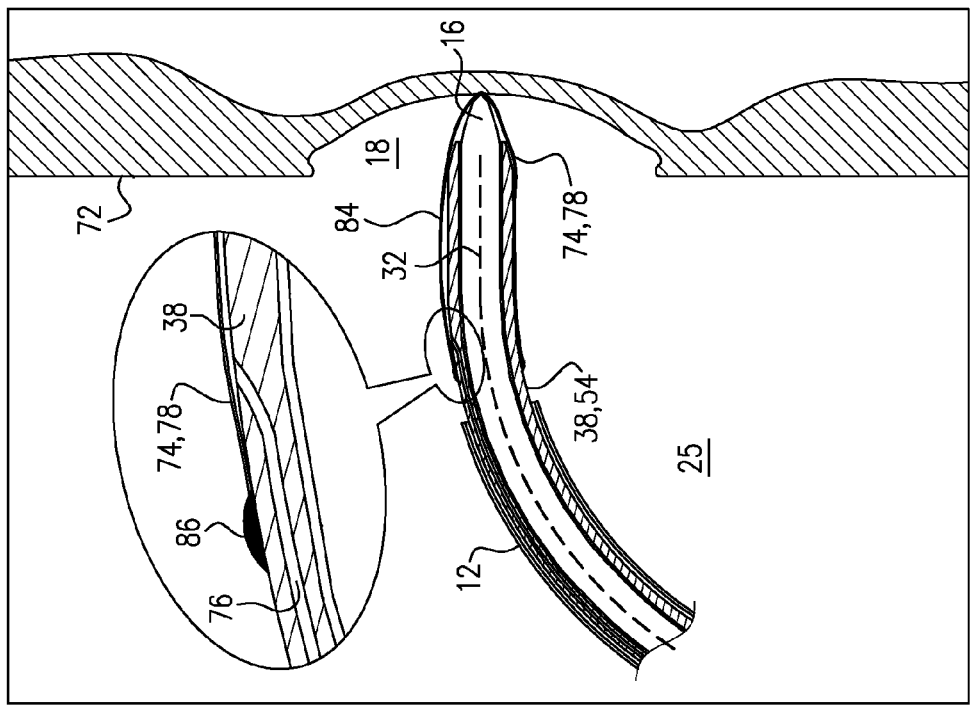
Figure 7A:
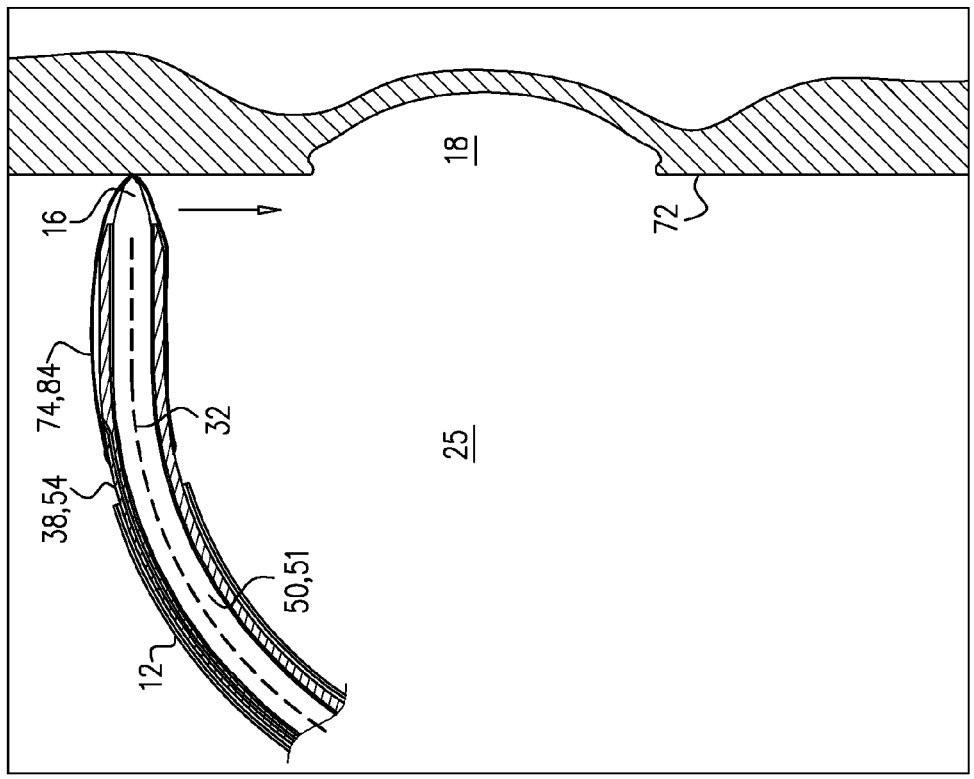

Reference is now made to FIGS. 5-7, which are schematic illustrations of apparatus 34 for puncturing a fossa ovalis 18 of a heart, in accordance with some applications of the present invention. As in applications described hereinabove, apparatus 34 comprises catheter 38, shaped to define catheter lumen 52, and also comprises puncturing element 32. Apparatus 34 further comprises a radially-expandable element 74. As further described hereinbelow, radially-expandable element 74 is configured to be deployed from distal portion 54 of the catheter, radially expanded, and, upon being deployed and expanded, facilitate positioning of puncturing element 32, by contacting at least a portion of the fossa ovalis, e.g., by filling a majority of the fossa ovalis. The radially-expandable element is typically radially expanded by being filled with a fluid, e.g., saline water, via one or more filling tubes 76 running through catheter 38. As described hereinabove, apparatus 34 typically comprises dilator element 49, and puncturing element 32 is typically slidably disposed within dilator lumen 51 of the dilator element.

In some applications, as shown in FIG. 5, radially-expandable element 74 comprises a compliant balloon 80. In the context of the present application and in the claims, a material which is "compliant" is able to stretch at least 20% without undergoing plastic deformation. Typically, balloon 80 is configured to not be fully expanded when an internal pressure of the balloon is 30 mmHg. That is, balloon 80 is typically configured to not undergo plastic deformation when an internal pressure of the balloon is raised to 30 mmHg; alternatively or additionally, at an internal pressure of 30 mmHg, the volume of the balloon is less than 75% of the volume of the balloon at which the balloon begins to undergo plastic deformation. In some applications, balloon 80 is configured to not be fully expanded even when an internal pressure of the balloon is 50 mmHg. That is, balloon 80 is configured to not undergo plastic deformation, even when an internal pressure of the balloon is raised to 50 mmHg. In some applications, balloon 80 has a maximum volume of between 1 and 8 mL, e.g., between 1 and 5 mL, e.g., 3 mL, the maximum volume being the volume at which the balloon begins to undergo plastic deformation. Alternatively or additionally, in some applications, the balloon has a maximum surface area not in contact with any other element of the apparatus of between 450 and 2000 mm2, e.g., between 500 and 1000 mm2, e.g., 750 mm2, whereby plastic deformation begins to occur beyond the maximum surface area. Typically, balloon 80 has a wall thickness (when not deployed/inflated) of 25-100 microns. The properties of balloon 80 described above generally facilitate effective deployment and expansion of the balloon, along with effective contacting of the fossa ovalis.

In some applications, radially-expandable element 74 comprises an at least partially radiopaque surface 78. Alternatively or additionally, apparatus 34 further comprises a contrast agent (not shown), and radially-expandable element 74 (e.g., compliant balloon 80 or non-compliant balloon 84, which is described below) is configured to contain the contrast agent, upon being deployed and expanded. For example, deploying radially-expandable element 74 from the distal portion of the catheter may comprise passing a contrast agent through filling tube(s) 76 and into the radially-expandable element. Using imaging (e.g., fluoroscopic imaging), surface 78 and/or the contrast agent may be viewed during and/or following the deployment of the radially-expandable element, in order to facilitate identification of the puncture site, as further described hereinbelow.

In some applications, as shown in FIGS. 6-7, radially-expandable element 74 comprises a non-compliant balloon 84. In such applications, apparatus 34 typically further comprises at least one slider 86 disposed along an outer surface of the catheter, in addition to a plurality of ribs 88 coupled to slider 86 and to a surface of the balloon (e.g., as shown in FIGS. 6B-C and 7C-D). Upon the catheter reaching the fossa ovalis (FIGS. 6B and 7B), slider 86 is distally slid from its initial position to a second position (FIGS. 6B and 7C), thus opening ribs 88. (By way of analogy, in some applications, the opening of ribs 88 may be similar to the opening of the ribs of an umbrella.) During and/or following the opening of ribs 88, the balloon is filled with a fluid, e.g., saline water. The slider then remains in the second position (FIGS. 6C and 7D), thus maintaining the expansion of the balloon.

In some applications, as shown in FIG. 7, balloon 84 covers a distal tip of catheter 38. (FIG. 7 shows the balloon covering dilator tip 16, which protrudes from the distal tip of the catheter.) In such applications, puncturing element 32 is typically configured to puncture balloon 84 immediately before puncturing the fossa ovalis; that is, the puncturing element is typically driven forward a single time, such that it punctures both balloon 84 and fossa ovalis 18 at effectively the same time. In some applications, the distal tip of the catheter is attached to an inner surface of the balloon.

In some applications, the maximum volume of balloon 84 is between 1 and 5 mL, and/or the maximum surface area of the balloon not in contact with any other element of the apparatus is between 450 and 1400 mm2, e.g., between 500 and 1000 mm2. These properties of balloon 84 generally facilitate effective deployment and expansion of the balloon, along with effective contacting of the fossa ovalis.

In some applications, e.g., as shown in FIGS. 5C-D and 6B-C, balloon 80 or balloon 84 is an annular balloon 82 (e.g., a generally torus-shaped balloon), shaped to define a hole, a distal portion of the catheter passing through the hole. (FIGS. 5C-D and 6B-C show cross-sections of the annulus.)

FIGS. 5-7 also show a method for puncturing fossa ovalis 18. The method begins with catheter 38 being inserted into right atrium 25 of the heart, and with distal portion 54 of the catheter being advanced toward the interatrial septum 72 of the heart, as described above with reference to FIGS. 3-4. Subsequently, the catheter is typically moved along the interatrial septum, for example, while contacting the interatrial septum with dilator tip 16. Upon the physician receiving an indication that the fossa ovalis may have been reached, e.g., upon sensing that the catheter has "fallen into a pit" (FIGS. 5B, 6B, and 7B), radially-expandable element 74 is deployed from the distal portion of the catheter (FIGS. 5C, 6B, and 7C). The manner in which radially-expandable element 74 contacts the septum is then used to identify a puncture site. For example, if radially-expandable element 74 comprises a radiopaque surface 78 (as described hereinabove), the radiopaque surface 78 may be viewed, using fluoroscopic imaging. If surface 78 appears relatively constrained, i.e., "squashed", the physician may conclude that the fossa ovalis has not been reached. If, on the other hand, the shape is relatively expansive, the physician may determine that a puncture site within the fossa ovalis has been reached, since the expansive shape may indicate that the radially-expandable element has expanded into the fossa ovalis. Subsequently, the fossa ovalis is punctured at the puncture site, using puncturing element 32.

In some applications, as shown in FIGS. 5D, 6C, and 7D, the radially-expandable element facilitates stabilization of catheter 38, by being in contact with the septum (e.g., with the fossa ovalis). The stabilization of the catheter, in turn, facilitates the steering of distal portion 54 of the catheter toward the puncture site, as shown, for example, in FIGS. 5D and 7D. Puncturing element 32 is then slid from the distal portion of the catheter and through the fossa ovalis, at the puncture site, as shown in FIG. 3D. The stabilization of the catheter may also facilitate adjusting an orientation of the distal portion of the catheter. Puncturing element 32 is then slid from the distal portion of the catheter and through the fossa ovalis, at an angle with respect to the fossa ovalis that is determined by the orientation of the distal portion of the catheter, as shown in FIG. 3E.

In some applications, as described hereinabove, the radially-expandable element comprises compliant balloon 80. In such applications, balloon 80 is typically deployed at an internal pressure of 10-70 mmHg, e.g., 30-50 mmHg. The volume of the balloon upon deployment (i.e., expansion) thereof is typically between 2 and 8 mL and/or between 0.5 and 4 mL, while a surface area of the balloon that is not in contact with the catheter is typically between 1500 and 3000 mm2 or between 300 and 1250 mm2. For non-compliant balloon 84, the deployment internal pressure is also typically 10-70 mmHg, e.g., 30-50 mmHg. The volume of the balloon upon deployment (i.e., expansion) thereof is also typically between 0.5 and 4 mL, e.g., between 2 and 4 mL, while a surface area of the balloon that is not in contact with the catheter is typically between 1500 and 2250 mm2 or between 300 and 1250 mm2.

Figure 8D:
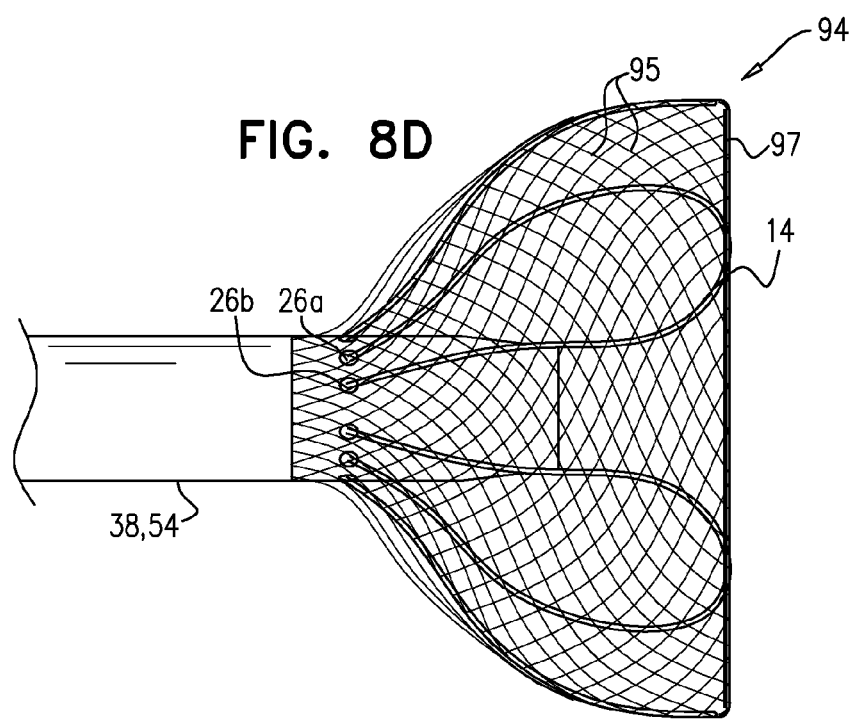

Reference is now made to FIGS. 8A-E, which are schematic illustrations of apparatus 34 for puncturing a fossa ovalis of a heart, in accordance with some applications of the present invention. As described hereinabove, apparatus 34 comprises catheter 38, along with puncturing element 32. Typically, as described hereinabove, apparatus 34 also comprises dilator element 49. Apparatus 34 also comprises a probing element 92, e.g., a mesh 94 disposed around distal portion 54 of catheter 38. During insertion of catheter 38 into the right atrium, mesh 94 is typically held in a constrained state by a tube or sheath, e.g., sheath 12 (FIG. 8A). Distal portion 54 of catheter 38 is advanced toward septum 72. Upon approaching septum 72, mesh 94 is deployed from distal portion 54 of the catheter, typically by the constraining tube or sheath being moved in a proximal direction, such that mesh 94 expands from its constrained state. Following mesh 94 being deployed, catheter 38 is moved along septum 72, and mesh 94 probes tissue near the fossa ovalis. While this probing takes place, mesh 94 has a first configuration, which is typically a relatively "squashed" configuration, as shown in FIG. 8B. Upon the catheter reaching fossa ovalis 18, the mesh probes tissue of the fossa ovalis, and automatically adopts a second configuration that is typically more expansive (i.e., less "squashed") than the first configuration (FIG. 8C). This change in configuration facilitates positioning of puncturing element 32. For example, a puncture site within the fossa ovalis may be identified in response to the mesh adopting the second configuration. Using puncturing element 32, the fossa ovalis is punctured at the puncture site.

In some applications, as shown in FIGS. 8C-D, apparatus 34 further comprises one or more flexible longitudinal members 14 slidably disposed within catheter lumen 52. Typically, flexible longitudinal members 14 are deployed and used as described above with reference to FIG. 3, and furthermore, typically have one or more of the properties described above with reference to FIG. 3. (For example, flexible longitudinal members 14 typically have loop-shaped deployed portions, are mechanically resilient, are deployed from openings 26, etc.) In some applications, as shown in FIGS. 8C-D, the mesh encloses all of the flexible longitudinal members. Alternatively, some or all of the flexible longitudinal members may be disposed outside of the mesh. Typically, flexible longitudinal members 14 are deployed after the fossa ovalis has been reached, and/or following the identification of the puncture site. As described hereinabove with reference to FIG. 3, by contacting the fossa ovalis, and/or by pushing against perimeter 60 of the fossa ovalis, the flexible longitudinal members may help stabilize the catheter, and/or facilitate steering of the catheter, and/or facilitate adjusting the orientation of the catheter, prior to the puncturing of the fossa ovalis. (As described above with reference to FIGS. 3D-E, a length of the deployed portion of at least one of the flexible longitudinal members may be adjusted, in order to facilitate the steering and/or orientation adjustment.)

Although the figures show flexible longitudinal members 14 specifically in combination with mesh 94, it is noted that the scope of the present invention includes combinations of longitudinal members 14 with other types of probing elements 92, such as with spring 104, described hereinbelow with reference to FIG. 10.

Figure 8E:
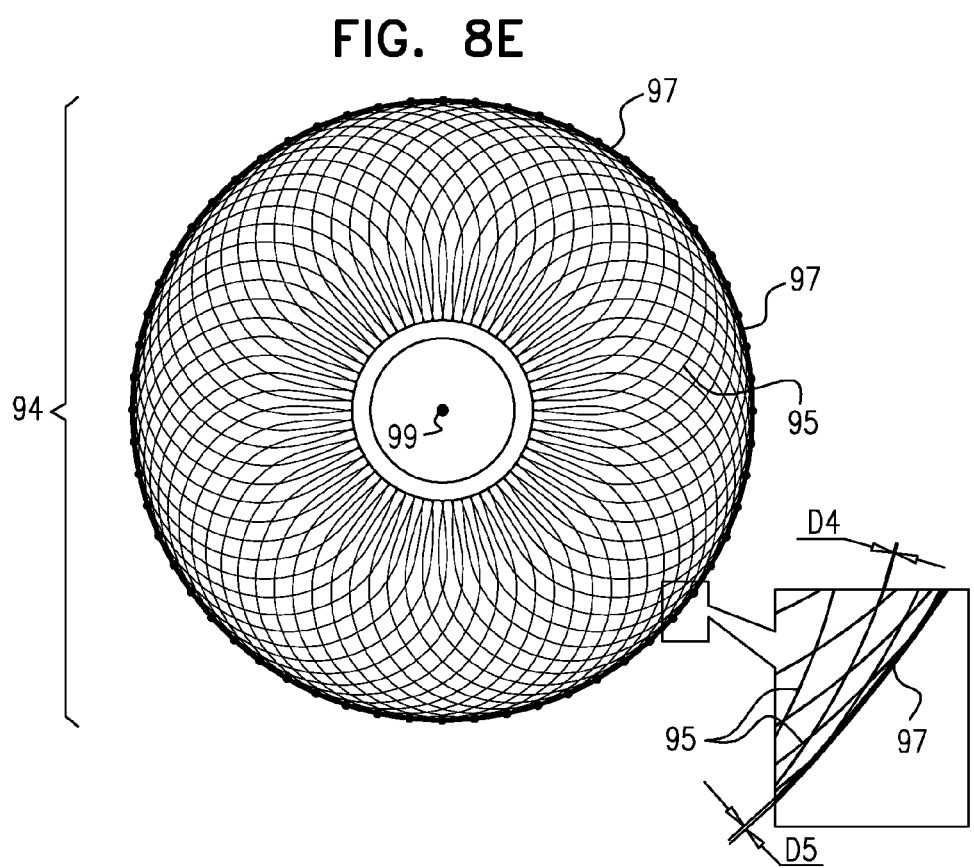

In some applications, as shown in FIGS. 8D-E, mesh 94 comprises two groups of longitudinal elements. The first group comprises relatively thin longitudinal elements 95, respective diameters D4 of each of which being between 0.05 and 0.125 mm. The second group comprises thicker longitudinal elements 97, respective diameters D5 of each of which being between 0.1 and 0.5 mm. Generally, thicker longitudinal elements 97 fulfill at least some of the function of flexible longitudinal members 14; for example, they typically facilitate stabilization of the catheter, prior to the puncturing, by pressing against perimeter 60 of the fossa ovalis. At least in order to facilitate this stabilization, the second group of longitudinal elements 97 is typically closer to the region of the mesh that contacts the fossa ovalis, relative to the first group of longitudinal elements 95. For example, if the mesh adopts the "cup" shape shown in FIG. 8D, longitudinal elements 97 may be closer to the "brim" of the cup. Alternatively or additionally, in some applications, an average distance of the second group of longitudinal elements from the center of mass 99 of the mesh is at least 20% greater than an average distance of the first group of longitudinal elements from center of mass 99, the center of mass being determined when the mesh is maximally flattened, as shown in FIG. 8E.

Reference is now made to FIG. 9, which is a schematic illustration of apparatus 34 for puncturing a fossa ovalis of a heart, in accordance with some applications of the present invention. As described hereinabove, apparatus 34 comprises catheter 38, along with puncturing element 32. Typically, as described hereinabove, apparatus 34 also comprises dilator element 49. As in FIG. 8, apparatus 34 also comprises a probing element 92, which, in the case of FIG. 9, comprises a plurality 96 of flexible longitudinal members 98. Typically, upon insertion of catheter 38 into the right atrium, flexible longitudinal members 98 are contained inside catheter 38, e.g., inside a lumen 100 within the wall of the catheter. Distal portion 54 of catheter 38 is advanced toward septum 72, and upon approaching septum 72, plurality 96 of flexible longitudinal members 98 is deployed. Following deployment, catheter 38 is moved along septum 72, and the flexible longitudinal members probe tissue near the fossa ovalis, typically by contacting the tissue with the distal tips 102 thereof. Plurality 96 may comprise any number of flexible longitudinal members. In some applications, only some of the flexible longitudinal members belonging to plurality 96 are in contact with the tissue at any given time.

While the probing of tissue near the fossa ovalis takes place, plurality 96 of flexible longitudinal members 98 has a first configuration, e.g., the rake-like configuration shown in FIG. 9. Upon the catheter reaching fossa ovalis 18, plurality 96 probes tissue of the fossa ovalis, and automatically adopts a second configuration that is different from the first configuration. For example, as shown in FIG. 9, a probing of perimeter 60 (e.g., a pressing against rim 62 of perimeter 60) of the fossa ovalis may cause at least one of the flexible longitudinal members to automatically adopt a buckled configuration. This change in configuration facilitates positioning of puncturing element 32, by indicating, for example, that a puncture site within the fossa ovalis has been reached. The pressing against rim 62 of perimeter 60 by at least one of the flexible longitudinal members further facilitates identification of the puncture site and/or the positioning of puncturing element 32, by opposing movement of probing element 92 from the fossa ovalis. Following the identification of the puncture site, the fossa ovalis is punctured, using the puncturing element.

Typically, distal tip 102 of at least one of the flexible longitudinal members is curved (e.g., J-shaped), in the absence of any force applied thereto. The curvedness of distal tip(s) 102 facilitates the configuration change, e.g., the buckling, described hereinabove.

Reference is now made to FIG. 10, which is a schematic illustration of apparatus 34 for puncturing a fossa ovalis of a heart, in accordance with some applications of the present invention. As described hereinabove, apparatus 34 comprises catheter 38, along with puncturing element 32. Typically, as described hereinabove, apparatus 34 also comprises dilator element 49. As in FIGS. 8 and 9, apparatus 34 also comprises a probing element 92, which, in the case of FIG. 10, comprises a spring 104. The deployment of spring 104 is generally as described above with respect to plurality 96 of flexible longitudinal members 98. Spring 104 is configured to probe tissue near the fossa ovalis, generally as described above with respect to mesh 94 and plurality 96 of flexible longitudinal members 98, with reference to FIGS. 8 and 9, respectively. While probing this tissue, spring 104 has a first configuration, which is typically a relatively compressed configuration. Upon probing tissue of the fossa ovalis, spring 104 automatically adopts a second configuration, which is typically a relatively expanded configuration, by elongating. As described hereinabove, this change in configuration typically facilitates identifying a puncture site, and/or positioning puncturing element 32.

Typically, probing element 92 (e.g., mesh 94, plurality 96 of flexible longitudinal members 98, or spring 104) is radiopaque, and/or apparatus 34 further comprises a plurality of radiopaque markers (not shown) coupled to the probing element. In such applications, fluoroscopic imaging may be used to view the probing element (e.g., such as to ascertain the configuration of the probing element) during and/or following deployment thereof. Upon viewing the change in configuration that occurs upon the probing of the fossa ovalis, the physician may determine that the desired puncture site has been reached. Further typically, probing element 92 comprises a shape-memory material configured to facilitate the deployment of the probing element. For example, spring 104, if comprising a shape-memory material, may immediately coil into a spring shape, upon being deployed from catheter 38.

In some applications, probing element 92 comprises a flexible sheet (not shown), which is functionally similar to mesh 94, at least in that it is deployed in a manner similar to the manner in which mesh 94 is deployed, and it undergoes a similar change in configuration upon probing the tissue of the fossa ovalis, i.e., it automatically adopts a second configuration that is typically more expansive than the first configuration (FIG. 8C). Typically, the shape of the flexible sheet is also similar to the shape of mesh 94 (e.g., it may have the "cup" shape shown in FIG. 8D), and the flexible sheet may also include a relatively thick, reinforced rim, which is analogous to thicker longitudinal elements 97 (FIGS. 8D-E). Typically, the flexible sheet includes a radiopaque pattern, e.g., an embedded or superimposed pattern of radiopaque material, such that fluoroscopic imaging may be used to view the flexible sheet (e.g., such as to ascertain the configuration of the flexible sheet) during and/or following deployment thereof.

In some applications, ultrasound imaging is used to view the probing element (e.g., such as to ascertain the configuration of the probing element), instead of or in addition to fluoroscopic imaging.

In some applications, before the puncturing of the fossa ovalis, the distal portion of the catheter is steered toward puncture site 55 (FIG. 3D), typically by pushing against the fossa ovalis with probing element 92 (e.g., plurality 96 of flexible longitudinal members 98 or spring 104). Following the steering of the distal portion of the catheter, the puncturing element is slid from the distal portion of the catheter and through the fossa ovalis at the puncture site (FIG. 3D). In some applications, before the puncturing of the fossa ovalis, an orientation of the distal portion of the catheter is adjusted, by using the probing element as a pivot. The puncturing element is then slid from the distal portion of the catheter and through the fossa ovalis, at an angle with respect to the fossa ovalis that is determined by the orientation of the distal portion of the catheter (FIG. 3E).

Figure 11:
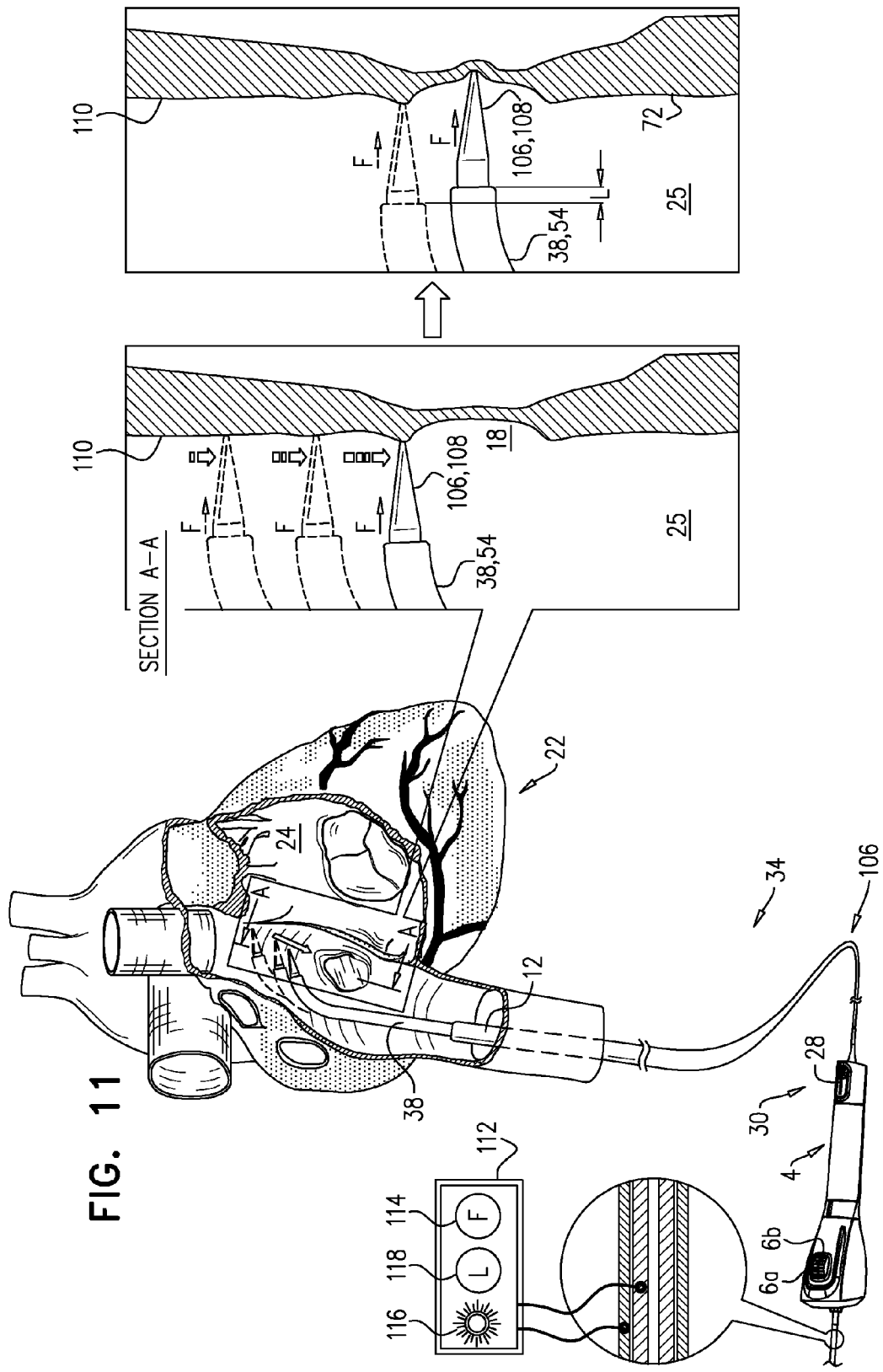

Reference is now made to FIG. 11, which is a schematic illustration of apparatus 34 for puncturing fossa ovalis 18 of a heart, in accordance with some applications of the present invention. Apparatus 34 comprises, as described hereinabove, catheter 38 and puncturing element 32, and also typically comprises dilator element 49. Apparatus 34 also comprises a sensor 106 comprising a probing element 108, which, as shown in FIG. 11, is slidably disposed within catheter lumen 52. As shown in FIG. 11, probing element 108 is configured to be deployed from distal portion 54 of the catheter, and, upon being deployed, probe tissue 110 (typically, tissue of septum 72) by applying a pushing force "F" to the tissue. As further described hereinbelow, sensor 106 is configured to facilitate identification of a puncture site and/or positioning of puncturing element 32, by measuring the pushing force.

Typically, sensor 106 comprises a load-cell sensor 112. The pushing force that is applied by the probing element to the tissue is also the pushing force that the tissue applies to the probing element; this force typically deforms a strain gauge (not shown) in load-cell sensor 112, and responsively to the deformation, an electric signal is generated. The electric signal, in turn, is indicative of the amount of pushing force. For example, a larger amount of current may indicate a larger pushing force. The measured force may be indicated, for example, by means of a force indicator 114. In some applications, probing element 108 comprises a spring (not shown), disposed, for example, between the proximal and distal ends of the probing element. When the probed tissue applies a pushing force to probing element 108, the spring is compressed, and sensor 106 measures the pushing force by measuring the compression of the spring.

In some applications, apparatus 34 further comprises an alert-generating mechanism 116. (As shown in FIG. 11, alert-generating mechanism 116 may, for example, be integrated with sensor 106, e.g., with load-cell sensor 112). The alert-generating mechanism is configured to generate an alert when the pushing force measured by sensor 106 at a given region of tissue is indicative of probing element 108 probing tissue of fossa ovalis 18. For example, tissue of fossa ovalis 18 is generally more compliant than other tissue of septum 72. Therefore, for a given displacement "L" of probing element 108, fossa ovalis 18 will typically push against probing element 108 with a lesser force, relative to other regions of septum 72. When this lesser force is measured, the alert-generating mechanism will generate an alert. The alert may comprise, for example, an audio or visual alert.

In some applications, sensor 106 (e.g., load-cell sensor 112) is further configured to facilitate identification of the puncture site and/or positioning of the puncturing element, by measuring the displacement "L" of the probing element. (The measured displacement may be indicated by means of a displacement indicator 118.) In such applications, alert-generating mechanism 116 is typically configured to generate an alert when the pushing force and the displacement measured by the sensor at a given region of tissue are indicative of the probing element probing tissue of the fossa ovalis. For example, the alert-generating mechanism may be responsive to a ratio of the displacement to the pushing force being higher at a given region of tissue, relative to another region of tissue. A higher ratio is indicative of a higher compliance, which in turn is indicative that the given region of tissue may lie in the fossa ovalis. Thus, the puncture site may be identified, and an alert may be generated.

Reference is now made to FIGS. 12A-H, which are schematic illustrations of apparatus 120 for identifying a puncture site for puncturing a fossa ovalis of a heart, in accordance with some applications of the present invention. Apparatus 120 comprises a shaft 122, a first joint 124, and a second joint 126 coupled to a distal portion 128 of shaft 122. Second joint 126 is slidably disposed with respect to first joint 124. Apparatus 120 further comprises a first arm 130 pivotably coupled, at a proximal portion thereof, to the first joint, and a second arm 132. Second arm 132 is pivotably coupled at a proximal portion thereof to the second joint, and at a distal portion thereof, to a distal portion of first arm 130. (In this context, the proximal portion of the first or second arm refers to the portion of the arm that is closer to shaft 122 when the arms are extended, as described hereinbelow. Similarly, the distal portion of the arm refers to the portion of the arm that is farther from shaft 122 when the arms are extended.) The first and second arms are typically coupled to one another at a joint 134.

As shown in FIG. 12, the first arm and/or the second arm is shaped to define a lumen 136 thereof (In FIG. 12, lumen 136 is shown only for first arm 130.) A positioning-facilitating element 138 is configured to be deployed from lumen 136. Typically, positioning-facilitating element 138 comprises probing element 92 (e.g., plurality 96 of flexible longitudinal elements 98, or spring 104) and/or radially-expandable element 74 (e.g., compliant balloon 80). As described above with reference to, for example, FIGS. 9 and 10, probing element 92 facilitates identification of a puncture site and/or positioning of the puncturing element, by undergoing a change in configuration (e.g., elongation of spring 104) upon probing tissue of the fossa ovalis. Similarly, as described above with reference to, for example, FIG. 5, radially-expandable element 74 facilitates identification of a puncture site and/or positioning of the puncturing element, by contacting at least a portion of the fossa ovalis, e.g., by filling a majority of the fossa ovalis. (In the application shown in FIG. 12, as opposed to the applications shown in FIGS. 5-7, radially-expandable element 74 is deployed from within a lumen, i.e., lumen 136.) Typically, positioning-facilitating element 138 is radiopaque, and/or has a plurality of radiopaque markers (not shown) coupled thereto, and fluoroscopic imaging is used to view the positioning-facilitating element during and/or following deployment thereof. Alternatively or additionally, ultrasound imaging is used to view the positioning-facilitating element during and/or following deployment thereof.

FIGS. 12A-F also show a method for identifying a puncture site and puncturing the fossa ovalis. Following insertion of apparatus 120 into the right atrium, and positioning of the apparatus opposite fossa ovalis 18 (FIG. 12A), second joint 126 is slid toward first joint 124, and the coupled distal portions of the first and second arms (e.g., joint 134) are moved toward interatrial septum 72 (FIG. 12B). Subsequently, positioning-facilitating element 138 is deployed from lumen 136, and the septum is contacted with the positioning-facilitating element (FIG. 12C). Positioning-facilitating element 138 facilitates identifying a puncture site, by contacting tissue near the fossa ovalis and tissue of the fossa ovalis. (For example, as described hereinabove, a change in configuration of probing element 92 upon contacting tissue of the fossa ovalis may help identify the puncture site.) If the physician decides that the fossa ovalis should be punctured at the identified puncture site, the fossa ovalis is subsequently punctured, using the puncturing element (FIGS. 12D-F). Alternatively, the physician may decide that a different puncture site is desired. In such an instance, positioning-facilitating element 138 is repositioned. Repositioning comprises, first, moving the positioning-facilitating element away from septum 72, by sliding the second joint away from the first joint. Subsequently, apparatus 120 is moved as appropriate, and the second joint is slid back toward the first joint. The positioning-facilitating element then facilitates the identification of a second puncture site, by contacting tissue of the fossa ovalis.

Typically, as shown in FIGS. 12D-F, the puncturing element is deployed from lumen 136, where lumen 136 typically includes two sub-lumens (not shown): one for the deployment of the positioning-facilitating element, and one for the deployment of the puncturing element.

In some applications, as shown in FIGS. 12A-F, second joint 126 is slid by means of a sliding of shaft 122. That is, second joint 126 typically does not move with respect to shaft 122, but rather, shaft 122 and second joint 126 slide together with respect to first joint 124. In other applications, as shown in FIGS. 12G-H, second joint 126 is configured to be slid with respect to the first joint by means of a change in a length of a spring 140. For example, as shown in FIGS. 12G-H, spring 140 may be disposed between the two joints, in which case second joint 126 is slid along shaft 122 toward first joint 124 by means of a compression of spring 140. Alternatively, spring 140 may be disposed in other locations, relative to the two joints. For example, spring 140 may be disposed on the far side of the second joint, in which case second joint 126 is slid toward first joint 124 by means of an elongation of the spring.

Reference is now made to FIG. 13, which is a schematic illustration of apparatus 142 for identifying a puncture site for puncturing a fossa ovalis of a heart, in accordance with some applications of the present invention. Apparatus 142 comprises a probing element 144 slidably disposed within the catheter lumen. Probing element 144 comprises a body 146 and a blunt head 148 pivotably coupled to body 146, e.g., via a hinge 150. Typically, a radius of curvature R of a distal portion of the blunt head is between 1 and 3 mm, e.g., between 1.3 and 1.6 mm. Further typically, blunt head 148 comprises a radiopaque blunt head 152, and/or has one or more radiopaque markers (not shown) attached thereto.

As shown in FIG. 13, catheter 38 is inserted into the right atrium, and distal portion 54 of the catheter is advanced toward septum 72. Probing element 144, or at least blunt head 148 of the probing element, is deployed from the distal portion of the catheter. The probing element probes tissue near the fossa ovalis and tissue of the fossa ovalis, typically moving in and out of the fossa ovalis, as shown in FIG. 13. Both the pivotability and the bluntness of the blunt head facilitate this movement. During the probing, fluoroscopic imaging and/or ultrasound imaging is typically used to view the blunt head (e.g., radiopaque blunt head 152). In response to the probing, a puncture site is identified.

Reference is now made to FIG. 14, which is a schematic illustration of apparatus 154 for identifying a puncture site for puncturing a fossa ovalis of a heart, in accordance with some applications of the present invention. Apparatus 154 comprises catheter 38 and a pushing element 156, which comprises a blunt head 158. As described above with respect to blunt head 148, a radius of curvature R of a distal portion of blunt head 158 is between 1 and 3 mm, e.g., between 1.3 and 1.6 mm. Pushing element 156 is slidably disposed within the catheter lumen, and a proximal portion 162 of the pushing element is coupled to a spring 160.

Catheter 38 is inserted into the right atrium, and distal portion 54 of the catheter is advanced toward septum 72. Subsequently, pushing element 156 is deployed from the distal portion of the catheter, and is used to probe tissue at a plurality of sites. The probing comprises (a) pushing with the pushing element, by compressing spring 160 to a compressed position (FIG. 14A), and (b) retracting the pushing element, by releasing the spring from the compressed position (FIG. 14B). (Typically, the spring is compressed and released by means of a cam 164.) In response to the probing, the puncture site is identified. For example, upon probing tissue of the fossa ovalis, it may be determined that the compression of spring 160 is greater, relative to the compression of the spring upon probing tissue that is outside the fossa ovalis. In response to the greater compression of the spring, the puncture site may be identified. Both the bluntness of blunt head 158 and the retractability of pushing element 156 facilitate the probing of tissue at the plurality of sites.

Figure 15A:
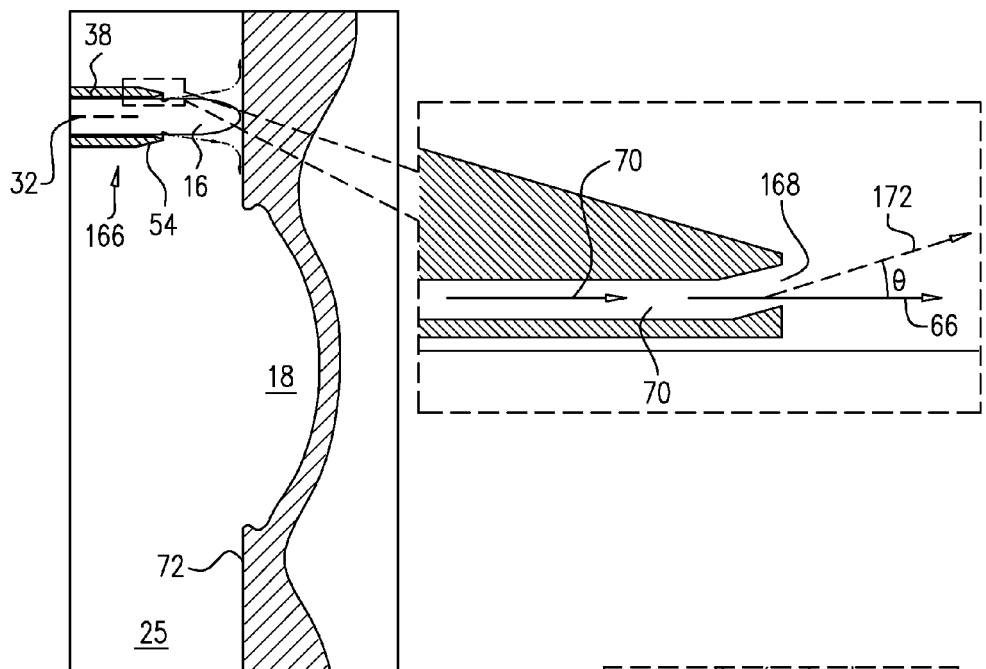
FIGS. 15A-B are schematic illustrations of apparatus for puncturing a fossa ovalis of a heart, in accordance with some applications of the present invention.
Figure 15B:
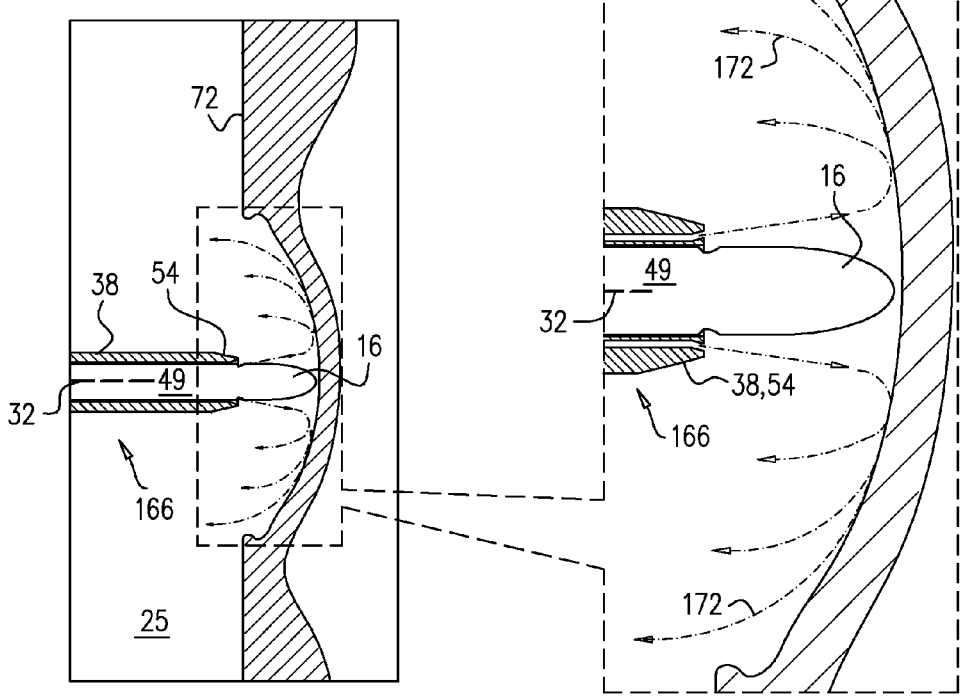

Reference is now made to FIGS. 15A-B, which are schematic illustrations of apparatus 166 for puncturing a fossa ovalis of a heart, in accordance with some applications of the present invention. Apparatus 166 comprising catheter 38 and puncturing element 32 slidably disposed within catheter lumen 52. As described above, the puncturing element is configured to be deployed from the distal portion of the catheter and to puncture the fossa ovalis. Apparatus 166 is shaped to define one or more orifices 168, which are typically at the distal portion of the catheter.

Catheter 38 is inserted into the right atrium, and the distal portion of the catheter is advanced toward septum 72 and is positioned near a potential puncture site. (As shown in FIGS. 15A-B, the potential puncture site may be contacted with dilator tip 16, which protrudes from the distal portion of the catheter.) Subsequently, one or more streams 172 of a contrast agent are released from the catheter, e.g., by orifices 168 directing the flow of streams 172. The flow of each stream is at an angle theta of at least 10 degrees with respect to a distally-pointing vector 66 that is parallel to longitudinal axis 70 of the catheter at the point of release of the stream, e.g., at the orifice from which the stream is released. Imaging (e.g., fluoroscopic imaging, MRI, etc.) is then used to view a pattern of flow of the contrast agent. In response to the viewing, the potential puncture site may be identified as the desired puncture site. For example, FIG. 15A shows a first pattern of flow that is indicative of the catheter not being positioned at the fossa ovalis, while FIG. 15B shows a second pattern of flow that is indicative of the catheter being positioned at the fossa ovalis. In response to viewing the second pattern of flow, the desired puncture site may be identified, and the puncturing element may be positioned accordingly. Subsequently, the fossa ovalis is punctured at the desired puncture site. As shown in FIG. 15, apparatus 166 typically comprises dilator element 49, and puncturing element 32 is typically slidably disposed within the dilator lumen.

In general, it is noted that any of the apparatus and methods described hereinabove may be used to facilitate the delivery of therapeutic devices to the left side of the heart, by identifying a puncture site, and/or by puncturing the fossa ovalis at the puncture site. Typically, following the puncturing of the fossa ovalis, puncturing element 32 is withdrawn while dilator element 49 is maintained in place against the septum, and a guidewire is deployed from catheter 38, through dilator element 49, and through the puncture. Dilator element 49 may then dilate the puncture by being deployed along the path established by the guidewire. Following the dilation of the puncture, a therapeutic device (e.g., a prosthetic valve or valve repair device) and/or catheter 38 may be passed through the puncture, along the path established by the guidewire.

A fossa-ovalis-puncturing experiment was conducted on a pig, using apparatus and techniques described hereinabove. A physician inserted the catheter through the femoral vein of the pig and into the right atrium, and deployed a flexible longitudinal member 14 as described hereinabove with reference to FIGS. 1A-E. As described hereinabove with reference to FIGS. 3B and 4B, the fossa ovalis was reached by moving the flexible longitudinal member along septum 72. (In one trial, the flexible longitudinal member was moved in a downward direction, while in another trial, it was moved in an upward direction.) Finally, the fossa ovalis was punctured. The time from entry of the catheter into the femoral vein until completion of the puncture was approximately one minute, which is significantly less time than is typically required using techniques of the prior art. Furthermore, an individual who is not a physician and had never before done a catheterization or fossa ovalis puncture was able to perform the procedure.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for puncturing a fossa ovalis of a heart, the method comprising:
    inserting a catheter into a right atrium of the heart;
    advancing a distal portion of the catheter toward an interatrial septum of the heart;
    deploying a balloon from the distal portion of the catheter;
    identifying a puncture site for puncturing the fossa ovalis, in response to a manner in which the balloon contacts the septum; and
    using a puncturing element, puncturing the fossa ovalis at the puncture site,
    wherein deploying the balloon further comprises deploying a non-compliant balloon, and
    wherein deploying the balloon further comprises expanding the balloon by:
    distally sliding at least one slider disposed along an outer surface of the catheter, the slider being coupled to a plurality of ribs coupled to a surface of the balloon, and filling the balloon with fluid.

2. The method according to claim 1, wherein deploying the balloon from the distal portion of the catheter further comprises passing a contrast agent through a filling tube and into the balloon, and wherein the method further comprises using imaging to view the contrast agent during and following the deployment of the balloon.

3. The method according to claim 1, further comprising, while the balloon is in contact with the septum, and before the puncturing of the fossa ovalis, using a stabilization of the catheter provided by the balloon being in contact with the septum to steer the distal portion of the catheter toward the puncture site,
    wherein puncturing the fossa ovalis comprises sliding the puncturing element from the distal portion of the catheter.

4. The method according to claim 1, further comprising, while the balloon is in contact with the septum, and before the puncturing of the fossa ovalis, using a stabilization of the catheter provided by the balloon being in contact with the septum to adjust an orientation of the distal portion of the catheter,
    wherein puncturing the fossa ovalis comprises sliding the puncturing element:
    from the distal portion of the catheter, and
    through the fossa ovalis, at an angle with respect to the fossa ovalis that is determined by the orientation of the distal portion of the catheter.

5. The method according to claim 1, wherein the balloon includes an at least partially radiopaque surface thereof, and wherein the method further comprises using fluoroscopic imaging to view the at least partially radiopaque surface during and following the deployment of the balloon.

6. The method according to claim 1, wherein deploying the balloon further comprises deploying the balloon at an internal pressure of 10-70 mmHg.

7. The method according to claim 1, wherein deploying the balloon further comprises deploying the balloon such that a volume thereof is between 0.5 and 4 mL.

8. The method according to claim 1, wherein the balloon covers a distal tip of the catheter.

9. The method according to claim 8, wherein the balloon comprises an inner surface of which is attached to the distal tip of the catheter.

10. The method according to claim 8, further comprising using the puncturing element to puncture the balloon immediately prior to puncturing the fossa ovalis.

11. The method according to claim 1, wherein deploying the balloon further comprises deploying the balloon that contains a contrast agent, and wherein the method further comprises using imaging to view the contrast agent during and following the deployment of the balloon.

12. The method according to claim 1, wherein deploying the balloon further comprises deploying the balloon such that a surface area thereof that is not in contact with the catheter is between 300 and 1250 mm2.

13. The method according to claim 1 wherein deploying the balloon further comprises deploying an annular balloon, shaped to define a hole, the distal portion of the catheter passing through the hole.

* * * * *